(12) United States Patent
Semenza

(10) Patent No.: US 6,222,018 B1
(45) Date of Patent: Apr. 24, 2001

(54) HYPOXIA INDUCIBLE FACTOR-1 AND METHOD OF USE

(75) Inventor: Gregg L. Semenza, Towson, MD (US)

(73) Assignee: The Johns Hopkins University School of Medicine, Baltimore, MD (US)

( * ) Notice: Subject to any disclaimer, the term of this patent is extended or adjusted under 35 U.S.C. 154(b) by 0 days.

(21) Appl. No.: 09/235,217

(22) Filed: Jan. 22, 1999

Related U.S. Application Data

(62) Division of application No. 08/480,473, filed on Jun. 6, 1995, now Pat. No. 5,882,914.

(51) Int. Cl.[7] .................................................. C07K 16/18

(52) U.S. Cl. .......................................................... 530/387.1

(58) Field of Search ........................................... 530/387.1

(56) References Cited

PUBLICATIONS

Fijiwara et al., Expressed Sequence Tag (EST) GenBank Accession Numbers D56430, D53682, R71408, T32121, HS14513, T32145, T35966, M8743, R71117, T32012, and Q60265. GenBank. May 30, 1995 see sequence alignments.

Wang et al., Proceeding of the National Academy of Sciences USA, 92:5510–5514, 1995.

Benjamin et al., Proceeding of the National Academy of Sciences USA, 87:6263–6267, 1990.

*Primary Examiner*—John S. Brusca
(74) *Attorney, Agent, or Firm*—Gray Cary Ware & Freidenrich LLP; Lisa A. Haile

(57) ABSTRACT

The purified and characterization of hypoxia-inducible factor 1 (HIF-1) is described. HIF-1 is composed of subunits HIF-1α and HIF-1β. Purified HIF-1α polypeptide, its amino acid sequence and polynucleotide sequence are provided. A HIF-1α variant that dimerizes to HIF-1β producing a non-functional HIF-1 complex is described. Methods for the prevention and treatment of hypoxia-related disorders are provided.

3 Claims, 29 Drawing Sheets

FIG. 10A

```
   1
   1
  62  AAG ATA AGT TCT GAA CGT CGA AAA GAA AAG
  12  lys ile ser ser glu arg arg lys glu lys
 182  TCG CAT CTT GAT AAG GCC TCT GTG ATG AGG
  52  ser his leu asp lys ala ser val met arg
 302  TAT TTG AAA GCC TTG GAT GGT TTT GTT ATG
  92  tyr leu lys ala leu asp gly phe val met
 422  GTG TTT GAT TTT ACT CAT CCA TGT GAC CAT
 132  val phe asp phe thr his pro cys asp his
 542  AAG TGT ACC CTA ACT AGC CGA GGA AGA ACT
 172  lys cys thr leu thr ser arg gly arg thr
 662  TAT AAG AAA CCA CCT ATG ACC TGC TTG GTG
 212  tyr lys lys pro pro met thr cys leu val
 782  TTT TCT TAT TGT GAT GAA AGA ATT ACC GAA
 252  phe ser tyr cys asp glu arg ile thr glu
 902  CAT GAT ATG TTT ACT AAA GGA CAA GTC ACC
 292  his asp met phe thr lys gly gln val thr
1022  CCA CAG TGC ATT GTA TGT GTG AAT TAC GTT
 332  pro gln cys ile val cys val asn tyr val
1142  ACT CAG CTA TTC ACC AAA GTT GAA TCA GAA
 372  thr gln leu phe thr lys val glu ser glu
1262  GAT TTT GGC AGC AAC GAC ACA GAA ACT GAT
 412  asp phe gly ser asn asp thr glu thr asp
1382  CCA TTA CCC ACC GCT GAA ACG CCA AAG CCA
 452  pro leu pro thr ala glu thr pro lys pro
```

FIG. 10B

```
TCT CGA GAT GCA GCC AGA TCT CGG CGA AGT
ser arg asp ala ala arg ser arg arg ser
CTT ACC ATC AGC TAT TTG CGT GTG AGG AAA
leu thr ile ser tyr leu arg val arg lys
GTT CTC ACA GAT GAT GGT GAC ATG ATT TAC
val leu thr asp asp gly asp met ile tyr
GAG GAA ATG AGA GAA ATG CTT ACA CAC AGA
glu glu met arg glu met leu thr his arg
ATG AAC ATA AAG TCT GCA ACA TGG AAG GTA
met asn ile lys ser ala thr trp lys val
CTG ATT TGT GAA CCC ATT CCT CAC CCA TCA
leu ile cys glu pro ile pro his pro ser
TTG ATG GGA TAT GAG CCA GAA GAA CTT TTA
leu met gly tyr glu pro glu glu leu leu
ACA GGA CAG TAC AGG ATG CTT GCC AAA AGA
thr gly gln tyr arg met leu ala lys arg
GTG AGT GGT ATT ATT CAG CAC GAC TTG ATT
val ser gly ile ile gln his asp leu ile
GAT ACA AGT AGC CTC TTT GAC AAA CTT AAG
asp thr ser ser leu phe asp lys leu lys
GAC CAG CAA CTT GAG GAA GTA CCA TTA TAT
asp gln gln leu glu glu val pro leu tyr
CTT CGA AGT AGT GCT GAC CCT GCA CTC AAT
leu arg ser ser ala asp pro ala leu asn
```

FIG. 10C

GTGAAGACATCGCGGGACCGATTCACC ATG
                                                             met
AAA GAA TCT GAA GTT TTT TAT GAG CTT GCT
lys glu ser glu val phe tyr glu leu ala
CTT CTG GAT GCT GGT GAT TTG GAT ATT GAA
leu leu asp ala gly asp leu asp ile glu
ATT TCT GAT AAT GTG AAC AAA TAC ATG GGA
ile ser asp asn val asn lys tyr met gly
AAT GGC CTT GTG AAA AAG GGT AAA GAA CAA
asn gly leu val lys lys gly lys glu gln
TTG CAC TGC ACA GGC CAC ATT CAC GTA TAT
leu his cys thr gly his ile his val tyr
AAT ATT GAA ATT CCT TTA GAT AGC AAG ACT
asn ile glu ile pro leu asp ser lys thr
GGC CGC TCA ATT TAT GAA TAT TAT CAT GCT
<u>gly arg ser ile tyr glu tyr tyr his ala</u>
GGT GGA TAT GTC TGG GTT GAA ACT CAA GCA
gly gly tyr val trp val glu thr gln ala
TTC TCC CTT CAA CAA ACA GAA TGT GTC CTT
phe ser leu gln gln thr glu cys val leu
AAG GAA CCT GAT GCT TTA ACT TTG CTG GCC
lys glu pro asp ala leu thr leu leu ala
AAT GAT GTA ATG CTC CCC TCA CCC AAC GAA
asn asp val met leu pro ser pro asn glu
CAA GAA GTT GCA TTA AAA TTA GAA CCA AAT
gln glu val ala leu lys leu glu pro asn

FIG. 10D

```
GAG GGC GCC GGC GGC GCG AAC GAC AAG AAA
glu gly ala gly gly ala asn asp lys lys
CAT CAG TTG CCA CTT CCA CAT AAT GTG AGT
his gln leu pro leu pro his asn val ser
GAT GAC ATG AAA GCA CAG ATG AAT TGC TTT
asp asp met lys ala gln met asn cys phe
TTA ACT CAG TTT GAA CTA ACT GGA CAC AGT
leu thr gln phe glu leu thr gly his ser
AAC ACA CAG CGA AGC TTT TTT CTC AGA ATG
asn thr gln arg ser phe phe leu arg met
GAT ACC AAC AGT AAC CAA CCT CAG TGT GGG
asp thr asn ser asn gln pro gln cys gly
TTC CTC AGT CGA CAC AGC CTG GAT ATG AAA
phe leu ser arg his ser leu asp met lys
TTG GAC TCT GAT CAT CTG ACC AAA ACT CAT
leu asp ser asp his leu thr lys thr his
ACT GTC ATA TAT AAC ACC AAG AAT TCT CAA
thr val ile tyr asn thr lys asn ser gln
AAA CCG GTT GAA TCT TCA GAT ATG AAA ATG
lys pro val glu ser ser asp met lys met
CCA GCC GCT GGA GAC ACA ATC ATA TCT TTA
pro ala ala gly asp thr ile ile ser leu
AAA TTA CAG AAT ATA AAT TTG GCA ATG TCT
lys leu gln asn ile asn leu ala met ser
CCA GAG TCA CTG GAA CTT TCT TTT ACC ATG
pro glu ser leu glu leu ser phe thr met
```

1502 CCC CAG ATT CAG GAT CAG ACA CCT AGT CCT
492 pro gln ile gln asp gln thr pro ser pro
1622 AAG TTG GAA TTG GTA GAA AAA CTT TTT GCT
532 lys leu glu leu val glu lys leu phe ala
1742 TTC CAG TTA CGT TCC TTC GAT CAG TTG TCA
572 phe gln leu arg ser phe asp gln leu ser
1862 GCT AAT GCC ACC ACT ACC ACT GCC ACC ACT
612 ala asn ala thr thr thr thr ala thr thr
1982 ACT AGT GCC ACA TCA TCA CCA TAT AGA GAT
652 thr ser ala thr ser ser pro tyr arg asp
2102 TCT GTC GCT TTG AGT CAA AGA ACT ACA GTT
692 ser val ala leu ser gln arg thr thr val
2222 GTA GGA ATT GGA ACA TTA TTA CAG CAG CCA
732 val gly ile gly thr leu leu gln gln pro
2342 ATT TTA ATA CCC TCT GAT TTA GCA TGT AGA
772 ile leu ile pro ser asp leu ala cys arg
2462 CTA CTG CAG GGT GAA GAA TTA CTC AGA GCT
812 leu leu gln gly glu glu leu leu arg ala
2605 CTACAATACTGCACAAACTTGGTTAGTTCAATTTTTGAT
2764 TTAAAAAATGCACCTTTTTATTTATTTATTTTTGGCTAG
2923 TTTTACATAAATAATAATGCTTTGCCAGCAGTACGTGGT
3082 CTGGAACATGACATTGTTAATCATATAATAATGATTCTT
3241 TCTGATGTTTCTATAGTCACTTTGCCAGCTCAAAAGAAA
3400 AAAATCATGCATTCTTAGCAAAATTGCCTAGTATGTTAA
3559 CAGTAAATATCTTGTTTTTTCTATGTACATTGTACAAAT

FIG. 10E

```
TCC GAT GGA AGC ACT AGA CAA AGT TCA CCT
ser asp gly ser thr arg gln ser ser pro
GAA GAC ACA GAA GCA AAG AAC CCA TTT TCT
glu asp thr glu ala lys asn pro phe ser
CCA TTA GAA AGC AGT TCC GCA AGC CCT GAA
pro leu glu ser ser ser ala ser pro glu
GAT GAA TTA AAA ACA GTG ACA AAA GAC CGT
asp glu leu lys thr val thr lys asp arg
ACT CAA AGT CGG ACA GCC TCA CCA AAC AGA
thr gln ser arg thr ala ser pro asn arg
CCT GAG GAA GAA CTA AAT CCA AAG ATA CTA
pro glu glu glu leu asn pro lys ile leu
GAC GAT CAT GCA GCT ACT ACA TCA CTT TCT
asp asp his ala ala thr thr ser leu ser
CTG CTG GGG CAA TCA ATG GAT GAA AGT GGA
leu leu gly gln ser met asp glu ser gly
TTG GAT CAA GTT AAC TGA GCTTTTTCTTAATTT
leu asp gln val asn OPA
CCCCTTTCTACTTAATTTACATTAATGCTCTTTTTTAGTA
GGAGTTTATCCCTTTTTCGAATTATTTTTAAGAAGATGCC
AGCCACAATTGCACAATATATTTTCTTAAAAAATACCAGC
AAATGCTGTATGGTTTATTATTTAAATGGGTAAAGCCATT
ACAATACCCTATGTAGTTGTGGAAGTTTATGCTAATATTG
TTTGCTCAAAATACAATGTTTGATTTTATGCACTTTGTCG
TTTTCATTCCTTTTGCTCTTTGTGGTTGGATCTAACACTA
```

FIG. 10F

```
GAG CCT AAT AGT CCC AGT GAA TAT TGT TTT
glu pro asn ser pro ser glu tyr cys phe
ACT CAG GAC ACA GAT TTA GAC TTG GAG ATG
thr gln asp thr asp leu asp leu glu met
AGC GCA AGT CCT CAA AGC ACA GTT ACA GTA
ser ala ser pro gln ser thr val thr val
ATG GAA GAC ATT AAA ATA TTG ATT GCA TCT
met glu asp ile lys ile leu ile ala ser
GCA GGA AAA GGA GTC ATA GAA CAG ACA GAA
ala gly lys gly val ile glu gln thr glu
GCT TTG CAG AAT GCT CAG AGA AAG CGA AAA
ala leu gln asn ala gln arg lys arg lys
TGG AAA CGT GTA AAA GGA TGC AAA TCT AGT
trp lys arg val lys gly cys lys ser ser
TTA CCA CAG CTG ACC AGT TAT GAT TGT GAA
leu pro gln leu thr ser tyr asp cys glu
CATTCCTTTTTTTGGACACTGGTGGCTCACTACCTAAAGC TGTTCTTTAATGCTGGATCACAGACAGCTCATTTTTCTCAGT
AATATAATTTTTGTAAGAAGGCAGTAACCTTTCATCATGAT
AGTTACTCATGGAATATATTCTGCGTTTATAAAACTAGTTT
TACATAATATAGAAAGATATGCATATATCTAGAAGGTATGT
TGTAACTGATATTAAACCTAAATGTTCTGCCTACCCTGTTG
CTATTAACATCCTTTTTTTCATGTAGATTTCAATAATTGAG
ACTGTATTGTTTGTTACATCAAATAAACATCTTCTGTGGA
```

FIG. 10G

```
TAT GTG GAT AGT GAT ATG GTC AAT GAA TTC
tyr val asp ser asp met val asn glu phe
TTA GCT CCC TAT ATC CCA ATG GAT GAT GAC
leu ala pro tyr ile pro met asp asp asp
TTC CAG CAG ACT CAA ATA CAA GAA CCT ACT
phe gln gln thr gln ile gln glu pro thr
CCA TCT CCT ACC CAC ATA CAT AAA GAA ACT
pro ser pro thr his ile his lys glu thr
AAA TCT CAT CCA AGA AGC CCT AAC GTG TTA
lys ser his pro arg ser pro asn val leu
ATG GAA CAT GAT GGT TCA CTT TTT CAA GCA
met glu his asp gly ser leu phe gln ala
GAA CAG AAT GGA ATG GAG CAA AAG ACA ATT
glu gln asn gly met glu gln lys thr ile
GTT AAT GCT CCT ATA CAA GGC AGC AGA AAC
val asn ala pro ile gln gly ser arg asn
AGTCTATTTATATTTTCTACATCTAATTTTAGAAGCCTGG TTTTTGGTATTTAAACCATTGCATTGCAGTAGCATCATT
CATAGGCAGTTGAAAAATTTTTACACCTTTTTTTTCACA
TTAAGAAGAAATTTTTTTTGCCCTATGAAATTGTTAAAC
GGCATTTATTTGGATAAAATTCTCAATTCAGAGAAATCA
GTATAAAGATATTTTGAGCAGACTGTAAACAAGAAAAAA
TAATTTTAGAAGCATTATTTTAGGAATATATAGTTGTCA
AAAAAAAAAAAAAAAAAAAAAAAAAAAAAAAAAAAAAAAA
```

FIG. 10H

| | | BASIC | | HELIX | LOOP | HELIX | |
|---|---|---|---|---|---|---|---|
| HIF-1α: | (17) | RRKEKSRDAARSRR | SKESEVFYELAHQL | PLPHNVSSHLD | KASVMRLTISYLRVR | |
| ARNT: | (90) | ARENHSEI-ERRRR | NKMTAYTTELSDMV | PTCSALARKPD | KLTILRMAVSHMKSL | (24%) |
| SIM: | (1) | MKEKSKNAARTRR | EKENTEFCELAKLL | PLPAAITSQLD | KASVIRLTTSYLKMR | (62%) |
| AHR: | (27) | AEGIKSNPS-KRHR | DRLNTELDRLASLL | PFPQDVINKLD | KLSVRLSVTYLRAK | (35%) |
| CONSENSUS: | | ---KS----R-RR | -K1----1-ELA-1L | P1P--1---LD | K-SV1RL2-SYL4-4 | |
| ARNT: | (90) | ARENHSEIERRRR | -NKMTAYITELSDMV | PTCSALARKPD-- | KLTILRMAVSHMKSL | |
| MI: | (205) | KKDNHNLIIRRRR | -FNINDRIKELGTLI | PKSNDPDMRWN-- | KGTILKASVDYIRKL | (32%) |
| USF: | (200) | RRAQHNEVERRRR | -DKINNWIVQLSKII | PDCSMESTKSGQS | KGGILSKACDYIQEL | (38%) |
| L-MYC: | (286) | KRKNHNFLERRRR | -NDLRSRFLALRDQV | PTL-ASCSKAP-- | KVVILSKALEYLQAL | (39%) |
| CP-1: | (223) | RKDSHKEVERRRR | ENINTA-INVLSDLL | PVR--ESSKAA-- | ---ILARAAEYIQKL | (37%) |
| CONSENSUS: | | 433-HNE1ERRRR | ---1----1--LSD11 | P------K----- | K--IL-4A13YIQ-L | |

FIG. 11

| | | | |
|---|---|---|---|
| HIF-1α: | (106) | DGDMIYISDNVNKYMGLTQFELTGHSVFDFTHPCDHEEMREML---THRNGLVK | (29%) |
| ARNT: | (183) | TGRVVYVSDSVTPVLNQPQSEWFGSTLYDQVHPDDVDKLREQL---STSENALT | (23%) |
| AHR: | (130) | DALVFYASSTIQDYLGFQQSDVIHQSVYELIHTEDRAEFQRQLHWALNPSQCT | (37%) |
| SIM: | (97) | DGKIMYISETASVHLGLSQVELTGNSIFEYIHNYDQDEMNAIL---SLHPHINQ | (22%) |
| PER: | (286) | DGIVLYTTPSITDVLGYPRDMWLGRSFIDFVHLKDRATFASQI---TTGIPIAE | (26%) |
| kinA: | (24) | NGRIIYISANSKLHLGYLQGEMIGSFLKTFLHEEDQFLVESYFYNEHHLMPCT | |
| CONSENSUS: | | DG--11Y1S--21----LG----Q--E11G--S1--311H----D----1---L--2---- | |
| | | | |
| HIF-1α: | (249) | DMKFSYCDERITELMGYEPEELLGR--SIYEYYHALDSDHLTK--THHDMFTKGQ | (35%) |
| ARNT: | (370) | EGIFTFVDHRCVATVGYQPQELLGK--NIVEFCHPEDQQLLRDSFQQVVKLKGQ | (31%) |
| AHR: | (288) | DFTPIGCDAKGRIVLGYTEAELCTRGSGYQFIHAADMLYCAE--SHIRMIKTGE | (39%) |
| SIM: | (263) | DMKLIFFDARVSQLTGYEPQDLIEK--TLYQYIHAADIMAMRC--SHQILLYKGQ | (33%) |
| PER: | (336) | TGIISHVDSAAVSALGYLPQDLIGR--SIMDFYHHEDLSVMKE--TYETVMKKGQ | (19%) |
| kinA: | (288) | WVFMNESGISLFEAATYE---DLIGK--NIYDQLHPCDHEDVKERIQNIAEQKTE | |
| CONSENSUS: | | 31-1---D-4----1GY-P-3L1G4-2TY3--H--D---143-2---11-KGQ | |

FIG. 12

1% OXYGEN
α
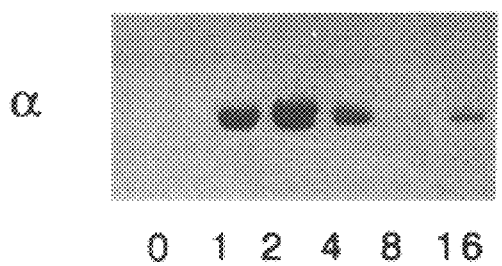
0  1  2  4  8  16
β
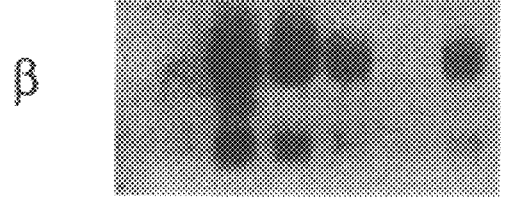
FIG. 13A
COBALT CHLORIDE
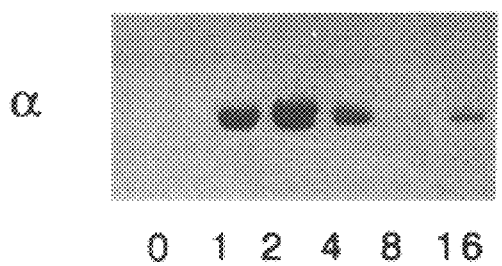
FIG. 13B
DESFERRIOXAMINE
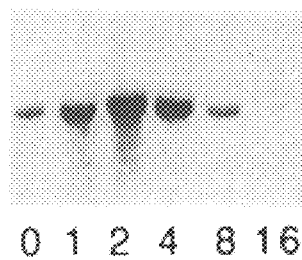
0  1  2  4  8  16
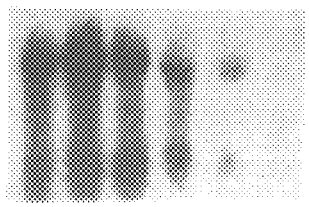
FIG. 13C
POST-HYPOXIA
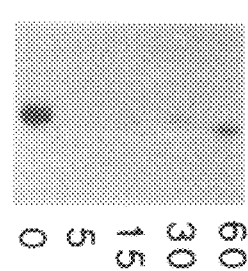
0  5  15  30  60
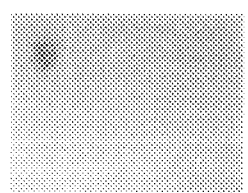
FIG. 13D

3'-UNTRANSLATED SEQUENCES

```
2568  CU  AUUUA  UA
2656  UA  AUUUA  CA
2731  GU  AUUUA  AA
2781  UU  AUUUA  UU
2785  UU  AUUUA  UU
3138  UU  AUUUA  AA
3156  CC  AUUUA  CA
3203  GC  AUUUA  UU
```

FIG. 13E

AMINO-TERMINAL AMINO-ACID SEQUENECE (ENCOMPASSING BASIC DOMAIN)
OF WILD-TYPE AND DOMINANT-NEGATIVE-MUTANT FORMS OF HIF-1α

HIF-1α :         1/MEGAGGANDKKKISSERRKEKSRDAARSRR/30

HIF-1αΔNB :      1/MEGIAG-----------------------SRR/30

HIF-1αΔNBΔAB :   1/MEGIAG-----------------------SRR/30

CARBOXY-TERMINAL AMINO-ACID SEQUENCE OF WILD-TYPE AND
DOMINANT-NEGATIVE-MUTATN FORMS OF HIF-1α

HIF-1α :         390/LKKEPDALT/400/820/RALDQVN/826

HIF-1αΔNB :      390/LKKEPDALT/400/820/RALDQVN/826

HIF-1αΔNBΔAB :   390/LKIQT----/395

FIG. 16

HYPOXIA INDUCIBLE FACTOR-1 AND METHOD OF USE

This is a divisional of U.S. application Ser. No. 08/480,473, filed Jun. 6, 1995, U.S. Pat. No. 5,882,914.

STATEMENT AS TO FEDERALLY SPONSORED RESEARCH

This invention was made in part with funds from the Federal government, PHS grant RO1-DK39869. The government therefore has certain rights in the invention.

FIELD OF THE INVENTION

This invention relates to hypoxia-related proteins, and specifically to novel DNA-binding proteins which are induced by hypoxia.

BACKGROUND OF THE INVENTION

Mammals require molecular oxygen ($O_2$) for essential metabolic processes including oxidative phosphorylation in which $O_2$ serves as electron acceptor during ATP formation. Systemic, local, and intracellular homeostatic responses elicited by hypoxia (the state in which $O_2$ demand exceeds supply) include erythropoiesis by individuals who are anemic or at high altitude (Jelkmann (1992) Physiol. Rev. 72:449–489), neovascularization in ischemic myocardium (White et al. (1992) Circ. Res. 71:1490–1500), and glycolysis in cells cultured at reduced $O_2$ tension (Wolfle et al. (1983) Eur. J. Biochem. 135:405–412). These adaptive responses either increase $O_2$ delivery or activate alternate metabolic pathways that do not require $O_2$. Hypoxia-inducible gene products that participate in these responses include erythropoietin (EPO) (reviewed in Semenza (1994) Hematol. Oncol. Clinics N. Amer. 8:863–884), vascular endothelial growth factor (Shweiki et al. (1992) Nature 359:843–845; Banai et al. (1994) Cardiovasc. Res. 28:1176–1179; Goldberg & Schneider (1994) J. Biol. Chem. 269:4355–4359), and glycolytic enzymes (Firth et al. (1994) Proc. Natl. Acad. Sci. USA 91:6496–6500; Semenza et al. (1994) J. Biol. Chem. 269:23757–23763).

The molecular mechanisms that mediate genetic responses to hypoxia have been extensively investigated for the EPO gene, which encodes a growth factor that regulates erythropoiesis and thus blood $O_2$-carrying capacity (Jelkmann (1992) supra; Semenza (1994) supra). Cis-acting DNA sequences required for transcriptional activation in response to hypoxia were identified in the EPO 3'-flanking region and a trans-acting factor that binds to the enhancer, hypoxia-inducible factor 1 (HIF-1), fulfilled criteria for a physiological regulator of EPO transcription: inducers of EPO expression (1% $O_2$, cobalt chloride [$CoCl_2$], and desferrioxamine [DFX]) also induced HIF-1 DNA binding activity with similar kinetics; inhibitors of EPO expression (actinomycin D, cycloheximide, and 2-aminopurine) blocked induction of HIF-1 activity; and mutations in the EPO 3'-flanking region that eliminated HIF-1 binding also eliminated enhancer function (Semenza (1994) supra). These results also support the hypothesis that $O_2$ tension is sensed by a hemoprotein (Goldberg et al. (1988) Science 242:1412–1415) and that a signal transduction pathway requiring ongoing transcription, translation, and protein phosphorylation participates in the induction of HIF-1 DNA-binding activity and EPO transcription in hypoxic cells (Semenza (1994) supra).

EPO expression is cell type specific, but induction of HIF-1 activity by 1% $O_2$, $CoCl_2$, or DFX was detected in many mammalian cell lines (Wang & Semenza (1993a) Proc. Natl. Acad. Sci. USA 90:4304–4308), and the EPO enhancer directed hypoxia-inducible transcription of reporter genes transfected into non-EPO-producing cells (Wang & Semenza (1993a) supra; Maxwell et al. (1993) Proc. Natl. Acad. Sci. USA 90:2423–2427). RNAs encoding several glycolytic enzymes were induced by 1% $O_2$, $CoCl_2$, or DFX in EPO-producing Hep3B or non-producing HeLa cells whereas cycloheximide blocked their induction and glycolytic gene sequences containing HIF-1 binding sites mediated hypoxia-inducible transcription in transfection assays (Firth et al. (1994) supra; Semenza et al. (1994) supra). These experiments support the role of HIF-1 in activating homeostatic responses to hypoxia.

SUMMARY OF THE INVENTION

The invention features a substantially purified DNA-binding protein, hypoxia-inducible factor-1 (HIF-1), characterized as activating structural gene expression where the promoter region of the structural gene contains an HIF-1 binding site. Examples of such structural genes include erythropoietin (EPO), vascular endothelial growth hormone (V-EGF), and glycolytic genes. HIF-1 is composed of two subunits, HIF-1α and an isoform of HIF-1β.

The invention features a substantially purified HIF-1α polypeptide, and a nucleotide sequence which encodes HIF-1α.

The invention provides methods for preventing and treating hypoxia-related disorders, including tissue damage resulting from hypoxia and reperfusion, by administering a therapeutically effective amount of HIF-1 protein. Also included in the invention is gene therapy by introducing into cells a nucleotide sequence encoding HIF-1. The invention also provides a pharmaceutical composition comprising a pharmaceutically acceptable carrier admixed with a therapeutically effective amount of HIF-1 or nucleotide sequence encoding HIF-1.

The invention further provides a novel HIF-1α variant polypeptide which functionally inactivates HIF-1 in vivo. The invention provides a method for treating an HIF-1-mediated disorder or condition by functional inactivation of HIF-1 by administration of an effective amount of the HIF-1α variant of the invention.

BRIEF DESCRIPTION OF THE DRAWINGS

FIG. 11 is the analysis of bHLH domains. Coordinate of first residue of each sequence and amino acid identity with HIF-1α (SEQ ID NO:36) or HIF-1β (ARNT) (SEQ ID NO:37) are given in parentheses at left and right margins, respectively. Hyphen indicates gap introduced into sequence to maximize alignment except in consensus where it indicates a lack of agreement. Consensus indicates at least 3 proteins with identical or similar residue at a given position. 1: F, I, L, M, or V; 2: S or T; 3: D or E; 4: K or R. Invariant residues are shown in bold (SEQ ID NOS:38–46).

FIG. 12 is the analysis of PAS domains. Alignments of PAS A (top) and B (bottom) subdomains are shown. Consensus indicates at least 4 proteins with identical or similar residue at a given position. GenBank accession numbers: ARNT, M69238; AHR, L19872; SIM, Ml9020; MI, Z23066; USF, X55666; L-MYC, X13945; CP-1, M34070; PER, M30114; KinA, M31067 (SEQ ID NOS:47–53).

FIG. 13A is an autoradiograph showing HIF-1α and HIF-1β RNA expression after exposure of Hep3B cells to 1% $O_2$ for 0, 1, 2, 4, 8, and 16 h.

FIG. 13B is an autoradiograph showing HIF-1α and HIF-1β RNA expression after exposure of Hep3B cells to 75 uM $CoCl_2$ for 0, 1, 2, 4, 8, and 16 h.

FIG. 13C is an autoradiograph showing HIF-1α and HIF-1β RNA expression after exposure of Hep3B cells to 130 uM desferrioxamine (DFX) for 0, 1, 2, 4, 8, and 16 h.

FIG. 13D is an autoradiograph showing HIF-1α and HIF-1β RNA expression after exposing Hep3B cells to 1% O₂ for 4 h, then returning the cells to 20% O₂ for 0, 5, 15, 30, or 60 min prior to RNA isolation.

FIG. 13E is a table of the AUUUA-containing elements from the HIF-1α 3'-UTR. The first nucleotide is numbered according to the composite cDNA sequence.

FIG. 16 is the amino-terminal (top) and carboxy-terminal (bottom) amino acid sequence of the wild-type and dominant-negative variant forms of HIF-1α (SEQ ID NOS:54–56).

DETAILED DESCRIPTION OF THE INVENTION

The invention provides a substantially pure hypoxia-inducible factor-1 (HIF-1) characterized as a DNA-binding protein which binds to a region in the regulatory, preferably in the enhancer region, of a structural gene having the HIF-1 binding motif. Included among the structural genes which can be activated by HIF-1 are erythropoietin (EPO), vascular endothelial growth factor (VEGF), and glycolytic gene transcription in cells subjected to hypoxia. Analysis of purified HIF-1 shows that it is composed of subunits HIF-1α and an isoform of HIF-1β. In addition to having domains which allow for their mutual association in forming HIF-1, the α and β subunits of HIF-1 both contain DNA-binding domains. The alpha subunit is uniquely present in HIF-1, whereas the beta subunit (ARNT) is a component of at least two other transcription factors.

The invention provides a substantially pure hypoxia-inducible factor-1α (HIF-1α) polypeptide characterized as having a molecular weight of 120 kDa as determined by SDS-PAGE and having essentially the amino acid sequence of SEQ ID NO:2 (FIG. 10) and dimerizing to HIF-1β to form HIF-1. The term "substantially pure" as used herein refers to HIF-1α which is substantially free of other proteins, lipids, carbohydrates or other materials with which it is naturally associated. One skilled in the art can purify HIF-1α using standard techniques for protein purification. The substantially pure polypeptide will yield a single band on a non-reducing polyacrylamide gel. The purity of the HIF-1α polypeptide can also be determined by amino-terminal amino acid sequence analysis. HIF-1α protein includes functional fragments of the polypeptide, as long as the activity of HIF-1α, such as the ability to bind with HIF-1β, remains. Smaller peptides containing the biological activity of HIF-1α are included in the invention.

Figure 10:
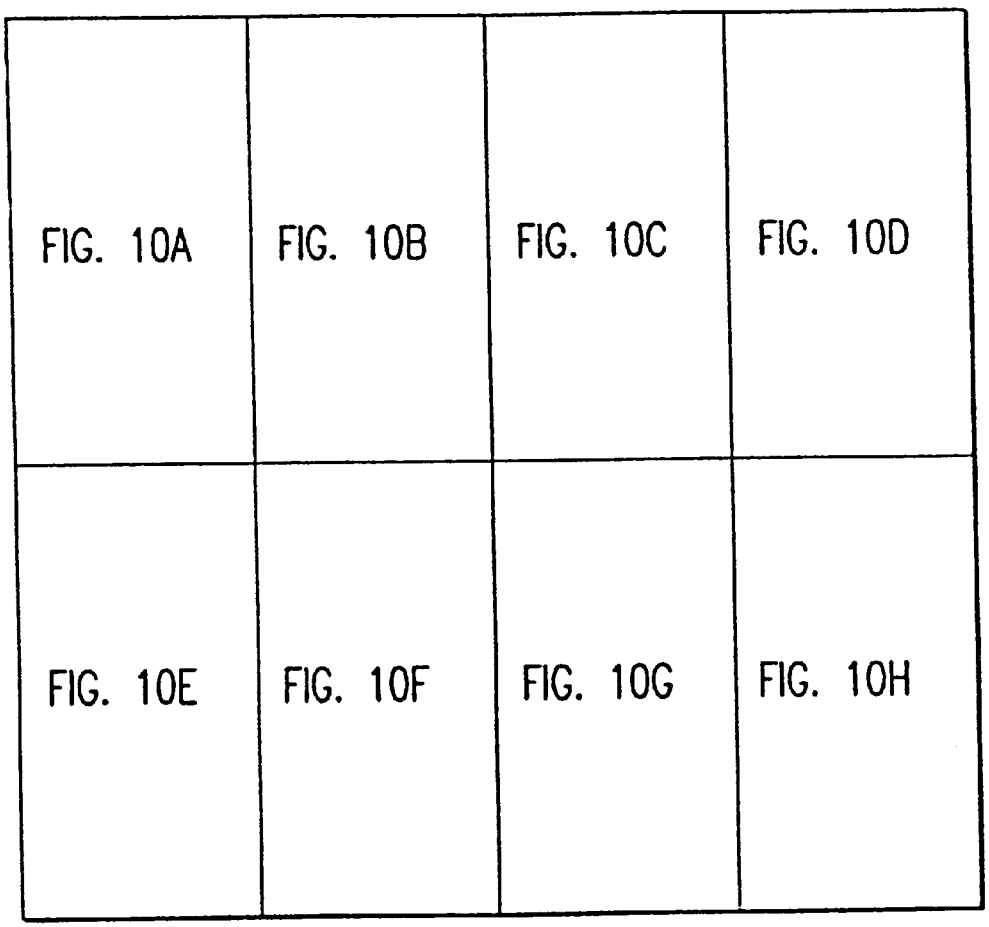
FIGS. 10A–10H is the nucleotide and derived amino acid sequence of HIF-1α (SEQ ID NOS:1 and 2). A composite sequence was derived from the complete nucleotide sequences determined for clones 3.2–3 (nt 1-3389), hbc025 (nt 135-3691), and hbc120 (nt 1739-3720). Sequences of four tryptic peptides obtained from the purified HIF-1α 120 kDa polypeptide are underscored (two peptides are contiguous).

The invention provides nucleotide sequences encoding the HIF-1α polypeptide (SEQ ID NO:1) (FIG. 10). These nucleotides include DNA, cDNA, and RNA sequences which encode HIF-1α. It is also understood that all nucleotide sequences encoding all or a portion of HIF-1α are also included herein, as long as they encode a polypeptide with HIF-1α activity. Such nucleotide sequences include naturally occurring, synthetic, and intentionally manipulated nucleotide sequences. For example, HIF-1α nucleotide sequences may be subjected to site-directed mutagenesis. The nucleotide sequence for HIF-1α also includes antisense sequences. The nucleotide sequences of the invention include sequences that are degenerate as a result of the genetic code. All degenerate nucleotide sequences are included in the invention as long as the amino acid sequence of HIF-1α polypeptide which is encoded by the nucleotide sequence is functionally unchanged.

Specifically disclosed herein is a DNA sequence encoding the human HIF-1α gene. The sequence contains an open reading frame encoding a polypeptide 826 amino acids in length. The human HIF-1α initiation methionine codon shown in FIG. 10 at nucleotide position 29–31 is the first ATG codon following the in-frame stop codon at nucleotides 2–4. Preferably, the human HIF-1α amino acid sequence is SEQ ID NO:2.

The nucleotide sequence encoding HIF-1α includes SEQ ID NO:1 as well as nucleic acid sequences complementary to SEQ ID NO:1. A complementary sequence may include an antisense nucleotide. When the sequence is RNA, the deoxynucleotides A, G, C, and T of SEQ ID NO:2 are replaced by ribonucleotides A, G, C, and U, respectively. Also included in the invention are fragments of the above-identified nucleic acid sequences that are at least 15 bases in length, which is sufficient to permit the fragment to selectively hybridize to DNA or RNA that encodes the polypeptide of SEQ ID NO:2 under physiological conditions.

Specifically, the fragments should hybridize to DNA or RNA encoding HIF-1α protein under stringent conditions.

Minor modifications of the HIF-1α primary amino acid sequence may result in proteins which have substantially equivalent activity as compared to the HIF-1α polypeptide described herein. Such proteins include those as defined by the term "having essentially the amino acid sequence of SEQ ID NO:2". Such modifications may be deliberate, as by site-directed mutagenesis, or may be spontaneous. All of the polypeptides produced by these modifications are included herein as long as the biological activity of HIF-1α still exists. Further, deletions of one or more amino acids can also result in modification of the structure of the resultant molecule without significantly altering its biological activity. This can lead to the development of a smaller active molecule which would have broader utility. For example, one can remove amino or carboxy terminal amino acids which are not required for HIF-1α biological activity.

The HIF-1α polypeptide of the invention encoded by the nucleotide sequence of the invention includes the disclosed sequence (SEQ ID NO:2) and conservative variations thereof. The term "conservative variation" as used herein denotes the replacement of an amino acid residue by another, biologically similar residue. Examples of conservative variations include the substitution of one hydrophobic residue such as isoleucine, valine, leucine, or methionine for another, or the substitution of one polar residue for another, such as the substitution of arginine for lysine, glutamic acid for aspartic acid, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

The DNA sequences of the invention can be obtained by several methods. For example, the DNA can be isolated using hybridization techniques which are well known in the art. These include, but are not limited to: 1) hybridization of genomic or CDNA libraries with probes to detect homologous nucleotide sequences, 2) polymerase chain reaction (PCR) on genomic DNA or cDNA using primers capable of annealing to the DNA sequence of interest, and 3) antibody screening of expression libraries to detect cloned DNA fragments with shared structural features.

Preferably the HIF-1α nucleotide sequence of the invention is derived from a mammalian organism, and most preferably from human. Screening procedures which rely on nucleic acid hybridization make it possible to isolate any gene sequence from any organism, provided the appropriate probe is available. Oligonucleotide probes, which correspond to a part of the sequence encoding the protein in question, can be synthesized chemically. This requires that short, oligopeptide stretches of amino acid sequences must be known. The DNA sequence encoding the protein can be deduced from the genetic code, however, the degeneracy of the code must be taken into account. It is possible to perform a mixed addition reaction when the sequence is degenerate. This includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA clone by the hybridization of the target DNA to that single probe in the mixture which is its complete complement (Sambrook et al. (1989) Molecular Cloning: A Laboratory Manual, 2nd Ed.; Cold Spring Harbor Laboratory Press, Plainview, N.Y.).

The development of specific DNA sequences encoding HIF-1α can also be obtained by: 1) isolation of double-stranded DNA sequences from the genomic DNA; 2) chemical manufacture of a DNA sequence to provide the necessary codons for the polypeptide of interest; and 3) in vitro synthesis of a double-stranded DNA sequence by reverse transcription of mRNA isolated from a eukaryotic donor cell. In the latter case, a double-stranded DNA complement of mRNA is eventually formed which is generally referred to as cDNA. of the three above-noted methods for developing specific DNA sequences for use in recombinant procedures, the isolation of genomic DNA isolates is the least common. This is especially true when it is desirable to obtain the microbial expression of mammalian polypeptides due to the presence of introns.

The synthesis of DNA sequences is frequently the method of choice when the entire sequence of amino acid residues of the desired polypeptide product is known. When the entire sequence of amino acid residues of the desired polypeptide is not known, the direct synthesis of DNA sequences is not possible and the method of choice is the synthesis of cDNA sequences. Among the standard procedures for isolating cDNA sequences of interest is the formation of plasmid- or phage-carrying cDNA libraries which are derived from reverse transcription of mRNA which is abundant in donor cells that express the gene of interest at a high level. When used in combination with polymerase chain reaction technology, even rare expression products can be cloned. In those cases where significant portions of the amino acid sequence of the polypeptide are known, the production of labeled single or double-stranded DNA or RNA probe sequences duplicating a sequence putatively present in the target cDNA may be employed in DNA/DNA hybridization procedures which are carried out on cloned copies of the cDNA which have been denatured into a single-stranded form (Jay et al. (1983) Nucl. Acid Res., 11:2325).

A cDNA expression library, such as lambda gt11, can be screened indirectly for HIF-1α peptides having at least one epitope, using antibodies specific for HIF-1α. Such antibodies can be either polyclonally or monoclonally derived and used to detect expression product indicative of the presence of HIF-1α cDNA.

DNA sequences encoding HIF-1α can be expressed in vitro by DNA transfer into a suitable host cell. "Host cells" are cells in which a vector can be propagated and its DNA expressed. The term also includes any progeny of the subject host cell. It is understood that all progeny may not be identical to the parental cell since there may be mutations that occur during replication. However, such progeny are included when the term "host cell"is used. Methods of stable transfer, meaning that the foreign DNA is continuously maintained in the host, are known in the art.

In the present invention, the HIF-1α nucleotide sequences may be inserted into a recombinant expression vector. The term "recombinant expression vector" refers to a plasmid, virus or other vehicle known in the art that has been manipulated by insertion or incorporation of the HIF-1α genetic sequences. Such expression vectors contain a promoter sequence which facilitates the efficient transcription in the host of the inserted genetic sequence. The expression vector typically contains an origin of replication, a promoter, as well as specific genes which allow phenotypic selection of the transformed cells. Vectors suitable for use in the present invention include, but are not limited to the T7-based expression vector for expression in bacteria (Rosenberg et al. (1987) Gene 56:125), the pMSXND expression vector for expression in mammalian cells (Lee and Nathans (1988) J. Biol. Chem. 263:3521) and baculovirus-derived vectors for expression in insect cells. The DNA segment can be present in the vector operably linked to regulatory elements, for example, a promoter (e.g., T7, metallothionein I, or polyhedron promoters).

Nucleotide sequences encoding HIF-1α can be expressed in either prokaryotes or eukaryotes. Hosts can include microbial, yeast, insect and mammalian organisms. Methods of expressing DNA sequences having eukaryotic or viral sequences in prokaryotes are well known in the art. Biologically functional viral and plasmid DNA vectors capable of expression and replication in a host are known in the art. Such vectors are used to incorporate DNA sequences of the invention.

Transformation of a host cell with recombinant DNA may be carried out by conventional techniques as are well known to those skilled in the art. Where the host is prokaryotic, such as E. coli, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be cotransformed with DNA sequences encoding the HIF-1α of the invention, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see, for example, Eukaryotic Viral Vectors, Cold Spring Harbor Laboratory, Gluzman ed., 1982).

Isolation and purification of microbial expressed polypeptide, or fragments thereof, provided by the invention, may be carried out by conventional means including preparative chromatography and immunological separations involving monoclonal or polyclonal antibodies.

The HIF-1α polypeptides of the invention can also be used to produce antibodies which are immunoreactive or bind to epitopes of the HIF-1α polypeptides. Such antibodies can be used, for example, in standard affinity purification techniques to isolate HIF-1α or HIF-1. Antibody which consists essentially of pooled monoclonal antibodies with different epitopic specificities, as well as distinct monoclonal antibody preparations are provided. Monoclonal antibodies are made from antigen containing fragments of the protein by methods well known in the art (Kohler et al. (1975) Nature 256:495; Current Protocols in Molecular Biology, Ausubel et al., ed., 1989).

For purposes of the invention, an antibody or nucleic acid probe specific for HIF-1α may be used to detect HIF-1α polypeptide (using antibody) or nucleotide sequences (using nucleic acid probe) in biological fluids or tissues. The antibody reactive with HIF-1α or the nucleic acid probe is preferably labeled with a compound which allows detection of binding to HIF-1α. Any specimen containing a detectable amount of antigen or polynucleotide can be used. Various detectable labels and assay formats are well known to those of ordinary skill in the art and can be utilized without resort to undue experimentation.

When the cell component is nucleic acid, it may be necessary to amplify the nucleic acid prior to binding with an HIF-1α specific probe. Preferably, polymerase chain reaction (PCR) is used, however, other nucleic acid amplification procedures such as ligase chain reaction (LCR), ligated activated transcription (LAT) and nucleic acid sequence-based amplification (NASBA) may be used.

The present invention provides a HIF-1α variant polypeptide characterized as dimerizing with HIF-1β to form a functionally inactive HIF-1 complex in that the complex is not able to sufficiently bind to the HIF-1 binding motif in the regulatory region to allow efficient expression of the structural gene under control of the regulatory region. The invention further provides nucleotide sequences encoding HIF-1α variants. In one specific embodiment, the polynucleotide encoding HIF-1α variant is provided having the polynucleotide sequence of SEQ ID NO:3. The HIF-1α variant polypeptide SEQ ID NO:4 is generated by substitution of wild-type amino acids with different amino acids and by deleting a portion of the wild-type sequence. Modifications of the HIF-1α variant amino acid sequence are encompassed by the invention so long as the resulting polypeptide dimerizes to HIF-1β to form a functionally inactive HIF-1 complex in the sense that the HIF-1 complex or dimer no longer sufficiently binds DNA. In a preferred embodiment of the invention, specific HIF-1α variants are provided wherein one or more the amino acids that participate in the binding of HIF-1 to DNA are replaced using techniques of genetic engineering.

The specific dominant-negative variant forms of HIF-1α are HIF-1αΔNB (SEQ ID NO:4) and HIF-1αΔNBΔAB (SEQ ID NO:3) (see Example 10). These two forms have in common a deletion of the amino acids that comprise the basic domain required for DNA binding (HIF-1α amino acid residues 17–30; FIG. 10). Any variant form of HIF-1α in which modification of the basic domain eliminates DNA binding activity while maintaining the ability of HIF-1α to dimerize with HIF-1β should function as a dominant negative variant. Such alterations of the nucleotide sequence encoding the basic domain include deletions or substitutions of critical basic amino acid residues within the domain that are required for DNA binding. Additional modifications of the protein may enhance the dominant negative effect in vivo. For example, the HIF-1αΔNBΔAB variant contains the same mutation in the basic domain as HIF-1αΔNB (FIG. 16) but, in addition, HIF-1αΔNBΔAB is also truncated at the carboxy terminus to improve its protein stability in vivo.

The nucleotide sequences encoding HIF-1α variant molecules of the invention can be inserted into an appropriate expression vector and expressed in cells. Modified versions of the specific HIF-1α variant of SEQ ID NO:4 can be engineered to enhance stability, production, purification, or yield of the expressed product. For example, the expression of a fusion protein or a cleavable fusion protein comprising the HIF-1α variant and a heterologous protein can be engineered. Such a fusion protein can be readily isolated by affinity chromatography, e.g., by immobilization on a column specific for the heterologous protein. Where a cleavage site is engineered between the HIF-1α moiety and the heterologous protein, the HIF-1α polypeptide can be released from the chromatographic column by treatment with an appropriate enzyme or agent that disrupts the cleavage site (Booth et al. (1988) Immunol. Lett. 19:65–708; Gardella et al. (1990) J. Biol. Chem. 265:15854–15859).

The invention provides methods for treatment of HIF-1-mediated disorders, including hypoxia-mediated tissue damage, which are improved or ameliorated by modulation of HIF-1 gene expression or activity. The term "modulate" envisions the inhibition of expression of HIF-1 when desirable, or enhancement of HIF-1 expression when appropriate. Where expression or enhancement of expression of HIF-1 is desirable, the method of the treatment includes direct (protein) or indirect (nucleotide) administration of HIF-1.

According to the method of the invention, substantially purified HIF-1 or the nucleotide sequence encoding HIF-1 is introduced into a human patient for the treatment or prevention of HIF-1-mediated disorders. The appropriate human patient is a subject suffering from a HIF-1-mediated disorder or a hypoxia-related disorder, such as atherosclerotic coronary or cerebral artery disease. When a patient is treated with nucleotide, the nucleotide can be a sequence which encodes HIF-1α or a nucleotide sequence which encodes HIF-1α and a nucleotide sequence which encodes HIF-1β (see, for example, Rayes, et al., *Sience,* 256:1193–1195, 1992; and Hoffman, et al., *Science,* 252:954–958, 1991).

Where inhibition of HIF-1α expression is desirable, such as the inhibition of tumor proliferation mediated by VEGF-induced angiogenesis, inhibitory nucleic acid sequences that interfere with HIF-1 expression at the translational level can be used. This approach utilizes, for example, antisense nucleic acid, ribozymes, or triplex agents to block transcription or translation of a specific HIF-1α mRNA or DNA, either by masking that mRNA with an antisense nucleic acid or DNA with a triplex agent, or by cleaving the nucleotide sequence with a ribozyme.

Antisense nucleic acids are DNA or RNA molecules that are complementary to at least a portion of a specific mRNA molecule (Weintraub (1990) Scientific American 262:40). In the cell, the antisense nucleic acids hybridize to the corresponding mRNA, forming a double-stranded molecule. The antisense nucleic acids interfere with the translation of the mRNA, since the cell will not translate a mRNA that is double-stranded. Antisense oligomers of about 15 nucleotides are preferred, since they are easily synthesized and are less likely to cause problems than larger molecules when introduced into the target HIF-1α-producing cell.

Use of an oligonucleotide to stall transcription is known as the triplex strategy since the oligomer winds around double-helical DNA, forming a three-strand helix. Therefore, these triplex compounds can be designed to recognize a unique site on a chosen gene (Maher et al. (1991) Antisense Res. and Dev. 1:227; Helene (1991) Anticancer Drug Design, 6:569).

Ribozymes are RNA molecules possessing the ability to specifically cleave other single stranded RNA in a manner analogous to DNA restriction endonucleases. Through the modification of nucleotide sequences which encode these RNAs, it is possible to engineer molecules that recognize specific nucleotide sequences in an RNA molecule and cleave it (Cech (1988) J. Amer. Med. Assn. 260:3030). A major advantage of this approach is that, because they are sequence-specific, only mRNAs with particular sequences are inactivated.

There are two basic types of ribozymes namely, tetrahymena-type (Hasselhoff (1988) Nature 334:585) and "hammerhead"-type. Tetrahymena-type ribozymes recognize sequences which are four bases in length, while "hammerhead"-type ribozymes recognize base sequences 11–18 bases in length. The longer the recognition sequence, the greater the likelihood that the sequence will occur exclusively in the target mRNA species. Consequently, hammerhead-type ribozymes are preferable to tetrahymena-type ribozymes for inactivating a specific mRNA species and 18-based recognition sequences are preferable to shorter recognition sequences.

Suppression of HIF-1 function can also be achieved through administration of HIF-1α variant polypeptide (dominant negative variant form), or a nucleotide sequence encoding HIF-1α variant polypeptide. For example, in the case of disorders enhanced by expression of HIF-1α, such as tumor proliferation secondary to VEGF-mediated angiogenesis, it would be desirable to "starve" the tumor by inhibiting neovascularization necessary to supply sufficient nutrients to the tumor. By administering HIF-1α variant polypeptide or a nucleotide sequence encoding such polypeptide, the variant will compete with wild-type HIF-1α for binding to HIF-1β in forming HIF-1 dimer thereby lowering the concentration of HIF-1 dimer in the cell which can efficiently bind to the HIF-1 DNA binding motif.

The present invention also provides gene therapy for the treatment of hypoxia-related disorders, which are improved or ameliorated by the HIF-1 polypeptide. Such therapy would achieve its therapeutic effect by introduction of the HIF-1α nucleotide, alone or in combination with HIF-1β nucleotide, into cells exposed to hypoxic conditions. Delivery of HIF-1α nucleotide, alone or in combination with HIF-β nucleotide, can be achieved using a recombinant expression vector such as a chimeric virus or a colloidal dispersion system. Especially preferred for therapeutic delivery of sequences is the use of targeted liposomes.

Various viral vectors which can be utilized for gene therapy as taught herein include adenovirus, adeno-associated virus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). Preferably, when the subject is a human, a vector such as the gibbon ape leukemia virus (GaLV) is utilized. A number of additional retroviral vectors can incorporate multiple genes. All of these vectors can transfer or incorporate a gene for a selectable marker so that transduced cells can be identified and generated. By inserting a HIF-1α sequence of interest into the viral vector, along with another gene which encodes the ligand for a receptor on a specific target cell, for example, the vector is now target specific. Retroviral vectors can be made target specific by attaching, for example, a sugar, a glycolipid, or a protein. Preferred targeting is accomplished by using an antibody to target the retroviral vector. Those of skill in the art will know of, or can readily ascertain without undue experimentation, specific polynucleotide sequences which can be inserted into the retroviral genome or attached to a viral envelope to allow target specific delivery of the retroviral vector containing the HIF-1α nucleotide sequence.

Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence which enables the packaging mechanism to recognize an RNA transcript for encapsidation. Helper cell lines which have deletions of the packaging signal include, but are not limited to Ψ2, PA317 and PA12, for example. These cell lines produce empty virions, since no genome is packaged. If a retroviral vector is introduced into such cells in which the packaging signal is intact, but the structural genes are replaced by other genes of interest, the vector can be packaged and vector virion produced.

Alternatively, NIH 3T3 or other tissue culture cells can be directly transfected with plasmids encoding the retroviral structural genes gag, pol and env, by conventional calcium phosphate transfection. These cells are then transfected with the vector plasmid containing the genes of interest. The resulting cells release the retroviral vector into the culture medium.

Another targeted delivery system for HIF-1α nucleotides is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. It has been shown that large unilamellar vesicles (LW), which range in size from 0.2–4.0 um can encapsulate a substantial percentage of an aqueous buffer containing large macromolecules. RNA, DNA and intact virions can be encapsulated within the aqueous interior and be delivered to cells in a biologically active form (Fraley, et al. (1981) Trends Biochem. Sci. 6:77). In addition to mammalian cells, liposomes have been used for delivery of polynucleotides in plant, yeast and bacterial cells. In order for a liposome to be an efficient gene transfer vehicle, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino et al. (1988) Biotechniques 6:682).

The composition of the liposome is usually a combination of phospholipids, particularly high-phase-transition-temperature phospholipids, usually in combination with sterols, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14–18 carbon atoms, particularly from 16–18 carbon atoms, and is saturated. Illustrative phospholipids include egg phosphatidylcholine, dipalmitoylphosphatidylcholine and distearoylphosphatidylcholine.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticuloendothelial system (RES) in organs which contain sinusoidal capillaries. Active targeting, on the other hand, involves alteration of the liposome by coupling the liposome to a specific ligand such as a monoclonal, antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand.

Due to the biological activity of HIF-1 in enhancing synthesis of VEGF, EPO, and glycolytic enzymes, there are a variety of applications using the polypeptide or nucleotide of the invention. Such applications include treatment of hypoxia-related tissue damage and HIF-1-mediated disorders, In addition, HIF-1 may be useful in various gene therapy procedures. HIF-1 can be used to prevent or repair hypoxia-mediated tissue damage. Important applications include the treatment of cerebral and coronary artery disease.

Conversely, blocking HIF-1 action either with anti-HIF-1 antibodies, anti-HIF-1α antibodies, or with an HIF-1α antisense nucleotide might slow or ameliorate diseases dependent on HIF-1 action, e.g., V-EGF-promoted tumor vascularization. The above described method for delivering an HIF-1α nucleotide are fully applicable to delivery of an HIF-1 antagonist for specific blocking of HIF-1 expression and/or activity when desirable. An HIF-1 antagonist can be an HIF-1 antibody, an HIF-1α antibody, an HIF-1α antisense nucleotide sequence, or the polypeptide or nucleotide of an HIF-1α variant.

The isolation and purification of HIF-1 from EPO-producing Hep3B cells and non-EPO-producing HeLa S3 cells is described in Examples 1–3. HIF-1 protein was purified 11,250-fold by DEAE ion-exchange and DNA affinity chromatography. Analysis of HIF-1 revealed 4 polypeptides having molecular weights of 91, 93, 94 (HIF-1β) and 120 kDa (HIF-1α). Glycerol gradient sedimentation analysis indicates that HIF-1 exists predominantly as a heterodimer and to a lesser extent as a heterotetramer.

The HIF-1α polypeptide was isolated and sequenced. Its cDNA was generated by PCR and its sequence determined. The HIF-1α polypeptide is characterized as a basic-helix-loop-helix (bHLH) polypeptide containing a PAS domain whose expression is regulated by cellular $O_2$ tension (Examples 4–7).

Induction of the transcription of genes encoding the glycolytic enzymes by HIF-1 was investigated (Example 9). The studies revealed that the glycolytic enzymes aldolase A (ALDA), phosphoglycerate kinase 1 (PGK1), and pyruvate kinase M (PKM) are induced by exposure of cells to HIF-1 inducers (1% $O_2$, $CoCl_2$, DFX). These genes have HIF-1 binding sites which were shown to specifically bind HIF-1. These results support the role of HIF-1 as a mediator of adaptive responses to hypoxia that underlie cellular and systemic oxygen homeostasis.

A dominant-negative variant of HIF-1α was generated lacking the basic domain (amino acid 17–30) of the protein which is required for the binding of HIF-1 to DNA (Example 10). The variant HIF-1α subunit can dimerize with HIF-1β, but the resulting heterodimer cannot bind DNA. In cells overexpressing the variant HIF-1α subunit, the majority of the HIF-1β subunits were engaged in non-functional heterodimers, resulting in functional inactivation of HIF-1. These results show that the HIF-1α variant is useful in vivo for blocking HIF-1 activity.

The following examples are intended to illustrate but not limit the invention. While they are typical of those that might be used, other procedures known to those skilled in the art may alternatively be used.

EXAMPLE 1

Experimental Methods

Human HIF-1 was purified, and its DNA binding activity characterized as follows.

Cell Culture and Nuclear Extract Preparation

Human Hep3B ant HeLa cells were maintained and treated with 1% $O_2$ and $COCl_2$ (Wang & Semenza (1993a) Proc. Natl. Acad. Sci. USA 90:4304–4308), and nuclear extracts were prepared as described previously (Semenza & Wang (1992) Mol. Cell. Biol. 12:5447–5454; Dignam et al. (1983) Nucleic Acids Res. 11:1474–1489). HeLa S3 cells, obtained from American Type Culture Collection were adapted to suspension growth in Spinner's minimum essential medium supplemented with 5% (v/v) horse serum (Quality Biological, Gaithersburg, Md.). The cells were grown to a density of $8 \times 10^5$ cells/ml and maintained by dilution to $2 \times 10^5$ cells/ml with fresh complete medium every 2 days. For induction of HIF-1 DNA binding activity, HeLa S3 cells were treated with 125 uM $CoCl_2$ for 4 h at 37° C. before harvesting by centrifugation for 10 min at 2,500× g. Cell pellets were washed twice with ice cold phosphate-buffered saline and resuspended in 5 packed cell volumes of buffer A (10 mM Tris-HCl (pH 7.6), 1.5 mM $MgCl_2$, 10 mM KCl) supplemented with 2 mM dithiothreitol (DTT), 0.4 mM phenylmethylsulfonyl fluoride and 1 mM $Na_3VO_4$. After incubation on ice for 10 min, cells were pelleted at 2,500×g for 5 min, resuspended in 2 packed cell volumes of buffer A, and lysed by 20 strokes in a glass Dounce homogenizer with type B pestle. Nuclei were pelleted at 10,000×g for 10 min and resuspended in 3.5 packed nuclear volumes of buffer C (0.42 M KCl, 20 mM Tris-HCl (pH 7.6), 20% glycerol, 1.5 MM $MgCl_2$) supplemented with 2 mM DTT, 0.4 mM phenylmethylsulfonyl fluoride, and 1 mM $Na_3VO_4$. Nuclear proteins were extracted by stirring at 4° C. for 30 min. After centrifugation at 15,000×g for 30 min, the supernatant was dialyzed against buffer Z-100 (25 mM Tris-HCl (pH 7.6), 0.2 mM EDTA, 20% glycerol, 2 mM DTT, 0.4 mM phenylmethylsulfonyl fluoride, 1 mM $Na_3VO_4$, and 100 mM KCl) at 4° C. The dialysate was clarified by ultracentrifugation at 100,000×g for 60 min at 4° C., and designated as crude nuclear extract. The nuclear extracts were aliquoted, frozen in liquid $N_2$, and stored at −80° C. Protein concentration was determined by the method of Bradford (1976) Anal. Biochem. 72:248–254, with a commercial kit (Bio-Rad) using bovine serum albumin (BSA) as a standard.

Gel Shift Assays

Gel shift assays were performed as described (Semenza & Wang (1992) Mol. Cell. Biol. 12:5447–5454, herein specifically incorporated by reference) except that the binding reaction was in buffer Z-100. For gel shift assays with partially purified and affinity-purified HIF-1 preparations, 0.25 mg/ml of BSA and 0.05% Nonidet P-40 were included in the binding reaction. Nonspecific competitor calf thymus DNA (Sigma) was used in reduced amounts for partially purified fractions, and no calf thymus DNA was used for affinity-purified HIF-1 fractions. For competition experiments, unlabeled oligonucleotide DNA was incubated with DEAE-Sepharose column fractions for 5 min on ice before probe DNA was added.

Nuclear extracts prepared from HeLa cells cultured in the presence of 0, 5, 10, 25, 50, 75, 100, 250, 500 or 1000 uM $CoCl_2$ for 4 h at 37° C., were incubated with W18 probe.

Methylation Interference Analysis

Methylation interference analysis was performed as described (Wang & Semenza (1993b) J. Biol. Chem. 268:21513–21518, herein specifically incorporated by reference), except 100 ug of nuclear extract prepared from $CoCl_2$-treated HeLa cells were used in the binding reactions.

Results

Figure 1:
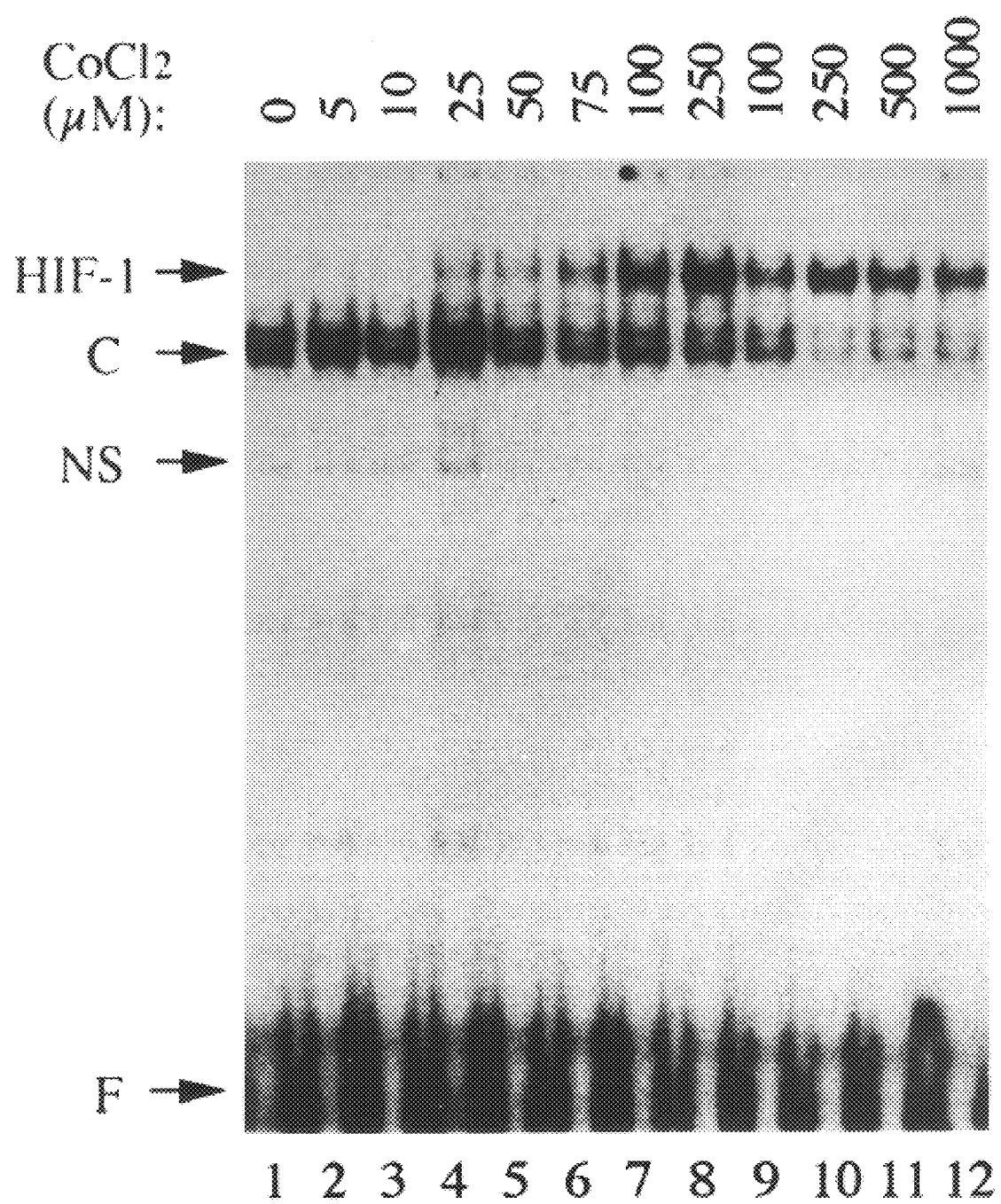
FIG. 1 is a autoradiograph showing dose-dependent induction of HIF-1 DNA binding activity by $CoCl_2$ treatment. Nuclear extracts, prepared from HeLa cells cultured in the presence of the 0, 5, 10, 25, 50, 75, 100, 250, 500, or 1000 uM of $CoCl_2$ for 4 h at 37° C., were incubated with W18 probe and analyzed by gel shift assay. Lanes 1–8 and 9–12 represent extracts prepared in two separate experiments. Arrows indicate HIF-1, constitutive DNA binding activity (C), nonspecific activity (NS), and free probe (F).

To determine the optimal concentration of $CoCl_2$ for induction of HIF-1 DNA binding activity, HeLa cells were treated with $CoCl_2$. Nuclear extracts were prepared and analyzed by gel shift assay with the wild-type oligonucleotide W18 (Example 2) as probe. Results are shown in FIG. 1. Induction of HIF-1 DNA binding activity by $CoCl_2$ was dose-dependent. HIF-1 activity in nuclear extracts was detected at 25 uM $CoCl_2$ and reached a peak activity at 250 uM. Significant cell death, however, was observed at $CoCl_2$ concentrations greater than 250 uM, resulting-in decreased yield of nuclear proteins. For this reason 125 uM $CoCl_2$ was chosen for subsequent large scale nuclear extract preparation. Constitutive DNA binding activities, which also bind W18 probe sequence specifically remained relatively unchanged in cells treated with 0–100 uM $CoCl_2$, and decreased at $CoCl_2$ concentration greater than 250 uM, suggesting an adverse effect of high $CoCl_2$ concentration on the cells. Nonspecific DNA binding activities were barely detectable in this particular gel shift assay and vary with cell type and the relative amount of nonspecific competitor DNA used.

Figure 2:
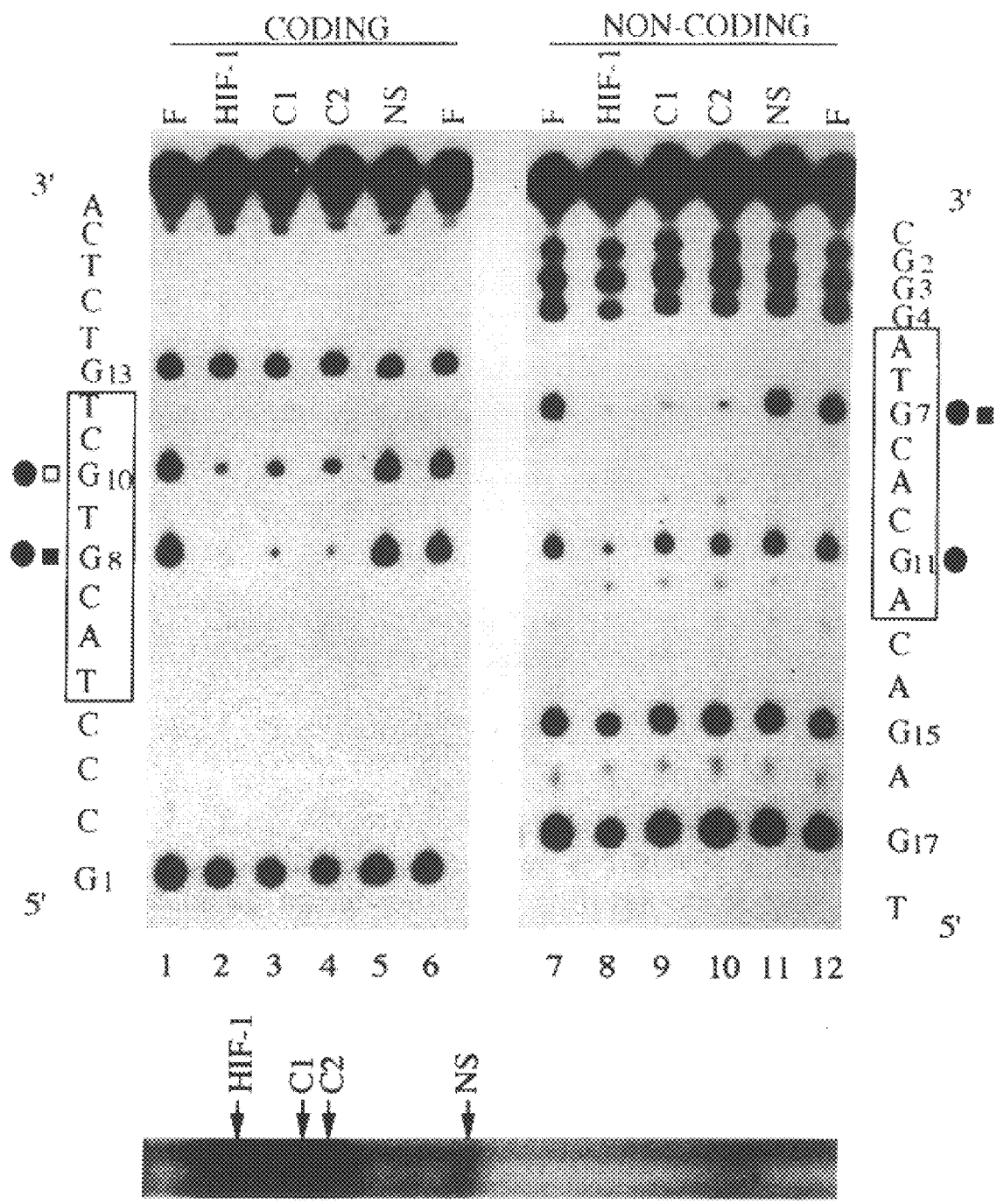
FIG. 2 is an autoradiograph showing the results of methylation interference analysis with nuclear extracts from $CoCl_2$-treated HeLa cells. W18 (SEQ ID NO:5) was 5'-end labeled on the coding or noncoding strand, partially methylated, and incubated with nuclear extracts. DNA-protein complexes corresponding to HIF-1, constitutive DNA binding activities (C1 and C2), and nonspecific binding activity (NS) were isolated from a preparative gel shift assay (lower) in addition to free probe (F) (not shown). DNA was purified, cleaved with piperidine, and analyzed on a 15% denaturing polyacrylamide gel (upper). Results are summarized at left for coding strand and at right for noncoding strand. The guanine residues are numbered according to their locations on the W18 probe. The HIF-1 binding site is boxed. Complete methylation interference with HIF-1 binding is indicated in closed circles; partial and complete methylation interference with constitutive DNA binding activity are indicated by open and closed squares, respectively.

Methylation interference analysis was performed to determine if HIF-1 from hypoxic Hep3B cells and $CoCl_2$-treated HeLa cells has the same DNA binding properties. As shown in FIG. 2, methylation of $G_8$ or $G_{10}$ on the coding strand eliminated or greatly reduced HIF-1 binding, respectively (FIG. 2, left, lane 2). Methylation of $G_{10}$ only partially interfered with the binding of constitutive factors (FIG. 2, left, lanes 3 and 4). On the noncoding strand, methylation of $G_7$ or $G_{11}$ blocked HIF-1 binding to the probe (FIG. 2B, right, lane 2). Only the methylation of $G_7$ interfered with binding of constitutive factors (FIG. 2B, right, lanes 3 and 4). The nonspecific binding activity was unaffected by DNA methylation on either strand (FIG. 2A, left, lane 5 and FIG. 2B, right, lane 5). The results indicate that (i) HIF-1 closely contacts $G_8$ and $G_{10}$ on the coding strand and $G_7$ and $G_{11}$ on the noncoding strand through the major groove of the DNA helix, and (ii) HIF-1 and the constitutive DNA binding factors can be distinguished by the nature of their DNA binding site contacts.

EXAMPLE 2

Biochemical Purification of HIF-1

Preparation of DNA Affinity Columns

DNA affinity columns were prepared by coupling multimerized double-stranded oligonucleotides to CNBr-activated Sepharose (Kadonaga & Tijan (1986) Proc. Natl. Acad. Sci. USA 83:5889–5893). The wild-type and the mutant column contained multimerized oligonucleotide W18 (SEQ ID NO:5) and M18 (SEQ ID NO:6) (mutation underlined), respectively.

W18: 5'-gatcGCCCTACGTGCTGTCTCA-3'     (SEQ ID NO:5)
3'-CGGGATGCACGACAGAGTctag-5'

M18: 5'-gatcGCCCTA<u>AAA</u>GCTGTCTCA-3'     (SEQ ID NO:6)
3'-CGGGATTTTCGACAGAGTctag-5'

Equal amounts of complementary oligonucleotides were annealed, phosphorylated, and ligated. Ligated oligonucleotides (60–500 bp) were extracted with phenol/chloroform, ethanol precipitated, resuspended in deionized water, and coupled to CNBr-activated Sepharose 4B as instructed by the manufacturer (Pharmacia Biotech Inc.). Approximately 50 ug of ligated double-stranded oligonucleotides were coupled per ml of Sepharose.

Purification of HIF-1

Crude nuclear extracts from 120 liters of $CoCl_2$-treated HeLa S3 cells (435 ml, 3,040 mg) were thawed on ice and clarified by centrifugation at 15,000×g for 10 min. Extracts were fractionated as three batches over a 36 ml DEAE-Sepharose CL-6B column (Pharmacia) in buffer Z-100 with a step gradient of increasing KCl. Fractions containing peak activity were pooled and dialyzed against buffer Z-100. The dialysate from DEAE-Sepharose columns was incubated with calf thymus DNA (Sigma) at a concentration of 4.4 ug/ml for 15 min on ice. After centrifugation at 15,000×g for 10 min, the supernatant (240 ml; 2.3 mg/ml) was applied to a 6 ml DNA affinity column prepared with concatenated W18 oligonucleotide. The fractions containing HIF-1 activity were pooled and dialyzed against buffer Z-100. The dialysate from the first DNA-affinity column was mixed with calf thymus DNA at a concentration of 2.5 ug/ml and incubated on ice for 15 min. After centrifugation (as described above), the supernatant was applied to a 1.5 ml M18 DNA-Sepharose column. The flowthrough from the M18 column was collected and reapplied to a second 2 ml W18 column. All buffers used for DNA affinity chromatography were supplemented with 0.05% Nonidet P-40 and 5 mM DTT. The amount of protein in affinity column fractions was quantitated by silver staining of SDS-polycrylamide gels or by Amido Black (Sigma) staining of nitrocellulose membranes (Schleicher & Schuell) spotted with protein samples and compared against known amounts of proteins standards (Bio-Rad).

For purification of HIF-1 from hypoxia-treated Hep3B cells, nuclear extracts (95 mg) were fractionated by the use of a 4 ml DEAE-Sepharose CL-6B column as described above. 0.25 M KCl elute fractions were dialyzed against buffer Z-100 and applied onto a Sephacryl S-300 gel filtration column (50 ml, 1.5×30 cm). The fractions containing HIF-1 activity were pooled an applied to a 2 ml calf thymus DNA column (0.8 mg of calf thymus DNA/ml of Sepharose) prepared by coupling single-stranded calf thymus DNA to CNBr-activated Sepharose 4B. The flowthrough was collected and applied to a 0.4 ml W18 column as described above after incubation with calf thymus DNA (2.2 ug/ml) for 10 min followed by another 0.2 ml W18 column after dialysis against buffer Z-100.

SDS-PAGE and Silver Staining

SDS-PAGE was carried out as described by Laemmli (1970) Nature 227:680–685. The gels were calibrated with high range molecular weight standards or prestained molecular weight markers (Bio-Rad). Electrophoresis was performed at 30 mA. Silver staining was performed with silver nitrate as described (Switzer et al. (1979) Anal. Biochem. 98:231–237). Molecular weight estimation for HIF-1 polypeptides was based on SDS-polyacrylamide gels with 3.2% cross-linking (acrylamide/bisacrylamide ration of 30:1).

Results

Figure 3A:
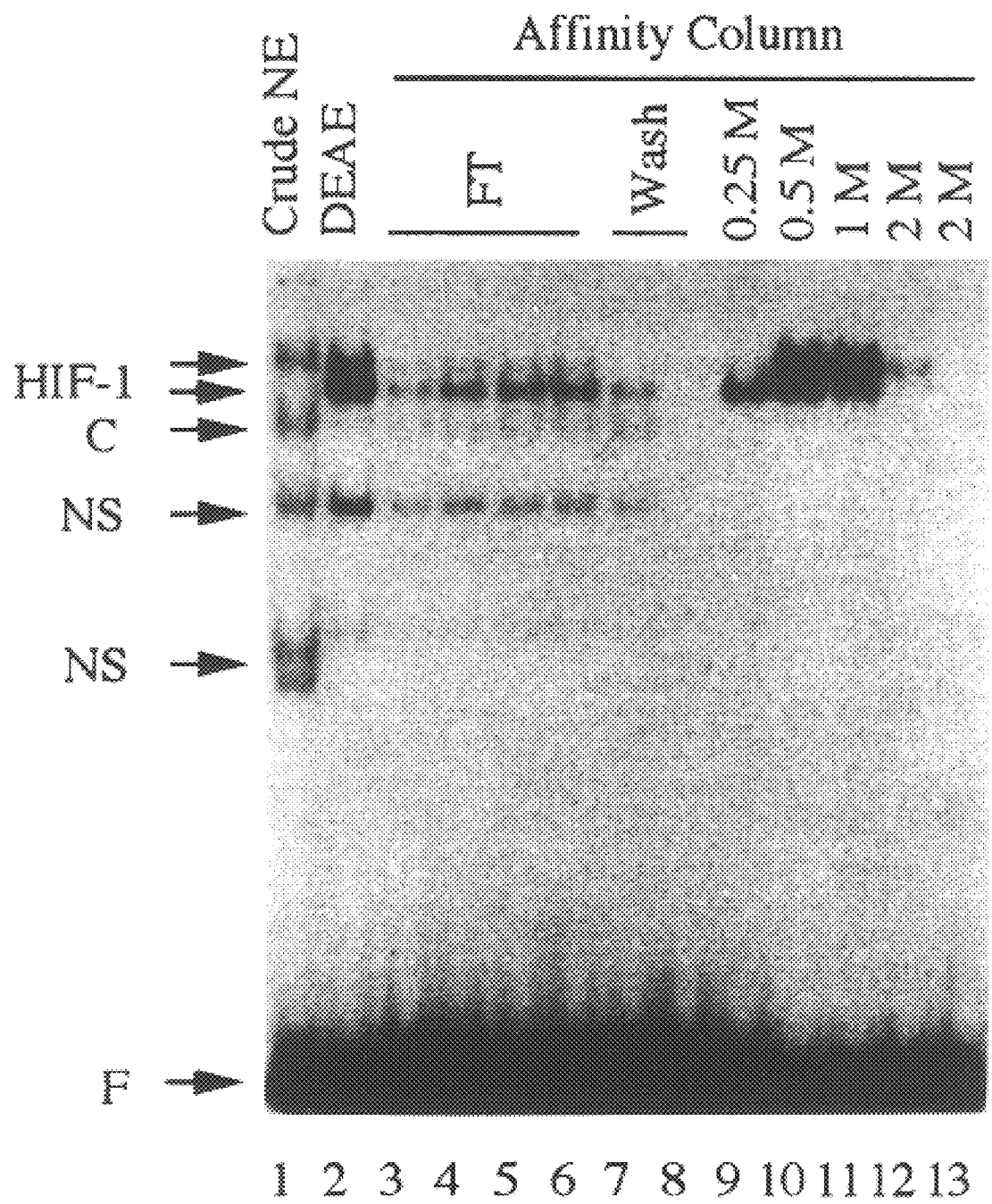
FIG. 3A is an autoradiograph showing gel shift assay analysis of column fractions for HIF-1 DNA binding activity. Nuclear extracts were fractionated by DEAE-Sepharose chromatography, and fractions containing HIF-1 activity were applied to a W18 DNA affinity column. 5 ug of protein were incubated with 0.1 ug of calf thymus DNA for gel shift analysis of crude nuclear extract (Crude NE, lane 1) and HIF-1 active fractions from DEAE-Sepharose columns (DEAE, lane 2). For fractions from the W18 column (lanes 3–13), 1 ul aliquots were incubated with 5 ng of calf thymus DNA. The positions of the two HIF-1 bands, constitutive activity (C), nonspecific activity (NS), and free probe (F) are indicated. FT, flowthrough, 0.25M, 0.5M, 1M, and 2M are fractions eluted with indicated concentration of KCl in buffer Z.
Figure 3B:
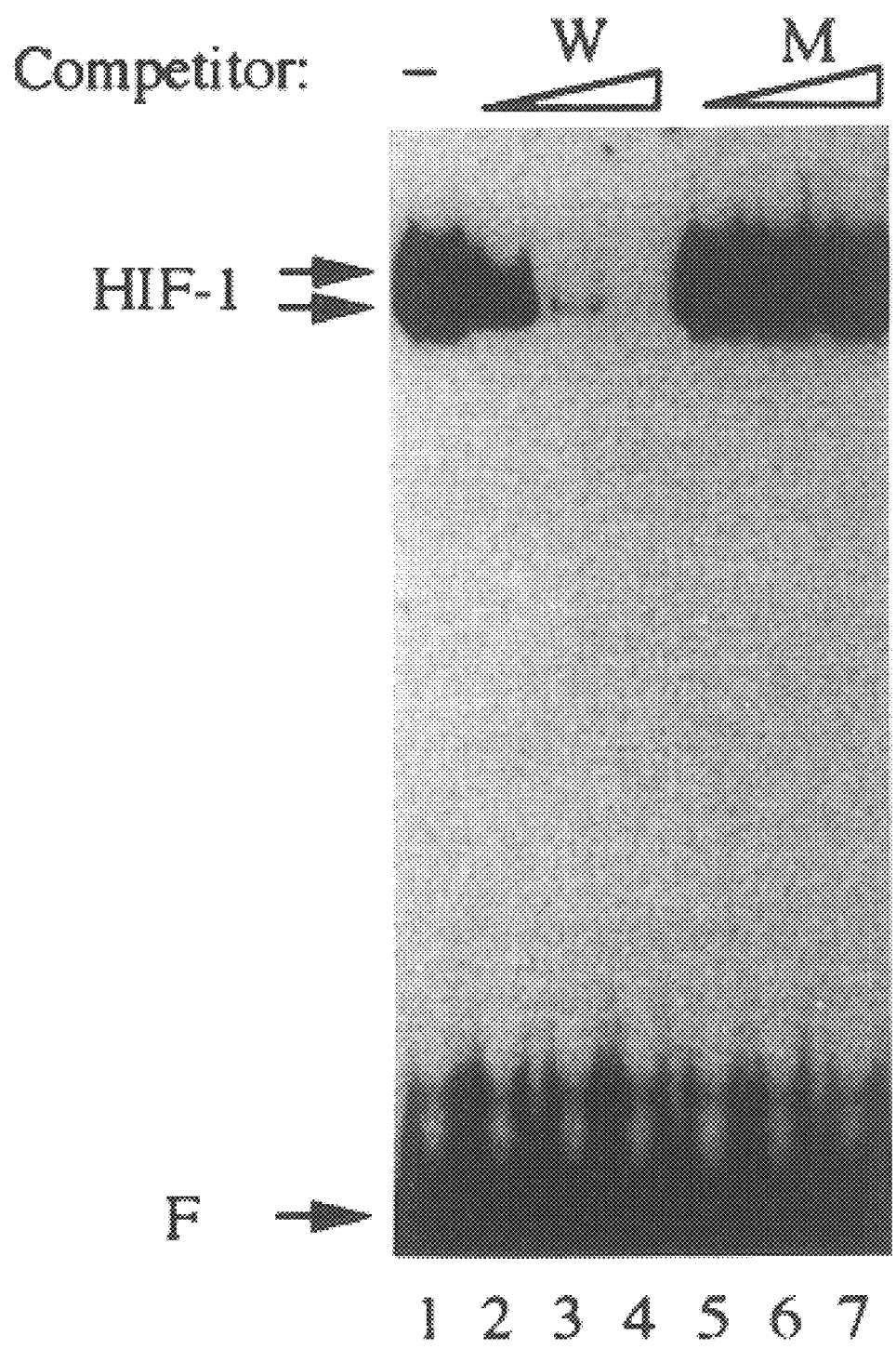
FIG. 3B is an autoradiograph showing sequence-specific DNA binding of the partially purified fractions described in the legend to FIG. 3A. 5 ug aliquots of fractions from the DEAE-Sepharose column were incubated with W18 probe in the presence of no competitor (lane 1), 10-fold (lanes 2 and 5), 50-fold (lanes 3 and 6), or 250-fold (lanes 4 and 7) molar excess of unlabeled W18 (W, lanes 2–4) or M18 (M, lanes 5–7) oligonucleotide.

Since HIF-1 DNA binding activity from hypoxic Hep3B cells and $CoCl_2$-treated HeLa cells are indistinguishable (Example 1), HeLa S3 cells treated with 125 uM $CoCl_2$ were used as starting material for the large scale purification of HIF-1. To purify HIF-1 by DNA affinity chromatography, the constitutive DNA binding activity had to first be separated from HIF-1 since both bind specifically to the W18 DNA sequence. Various ion-exchange resins and gel filtration matrices were examined. HIF-1 was retained on DEAE anion-change resins in buffer Z-100, whereas constitutive DNA binding activity was found in the flowthrough. HIF-1 DNA binding activity was eluted with 250 mM KCl in buffer Z. DEAE-Sepharose chromatography effectively removed constitutive DNA binding activity and resulted in a 4-fold purification of HIF-1 (FIG. 3A, lanes 1 and 2). This step, however, appeared to destabilize the HIF-1 protein complex and resulted in a faster migrating form of HIF-1 (FIG. 3A, lane 2, second arrow), which was also occasionally seen in crude nuclear extract preparations. This faster migrating form could be converted to the slower migrating HIF-1 band at higher salt concentrations, and HIF-1 appeared predominantly as the slower migrating form again after the first round of DNA affinity column chromatography (FIG. 3A, lanes 10–12), suggesting that no HIF-1 component was lost during the DEAE-Sepharose chromatography step. Probe binding of both HIF-1 forms could be competed by unlabeled W18 (FIG. 3B, lanes 2–4) but not M18 oligonucleotide (FIG. 3B, lanes 5–7), which contained a three-base pair substitution that abolished the ability of the EPO enhancer to mediate hypoxia-inducible transcription.

Partially purified HIF-1 fractions were then incubated with nonspecific competitor calf thymus DNA at concentrations that allowed optimal detection of HIF-1 DNA binding activity by gel shift assays and applied to a W18 DNA affinity column. Eluted fractions containing HIF-1 (0.5M KCl, FIG. 3A, lane 10; 1M KCl, FIG. 3A, lane 11) were pooled and dialyzed against buffer Z-100. To eliminate nonspecific DNA-binding proteins that were not removed by calf thymus DNA competitor, the dialysate was applied to an M18 DNA column. HIF-1 DNA binding activity was detected in the flowthrough, which was then applied directly onto second W18 column. HIF-1 activity was detected exclusively in 0.5M KCl fractions. Two rounds of W18 and one round of M18 column chromatography resulted in a purification of approximately 2,800-fold.

Figure 4A:
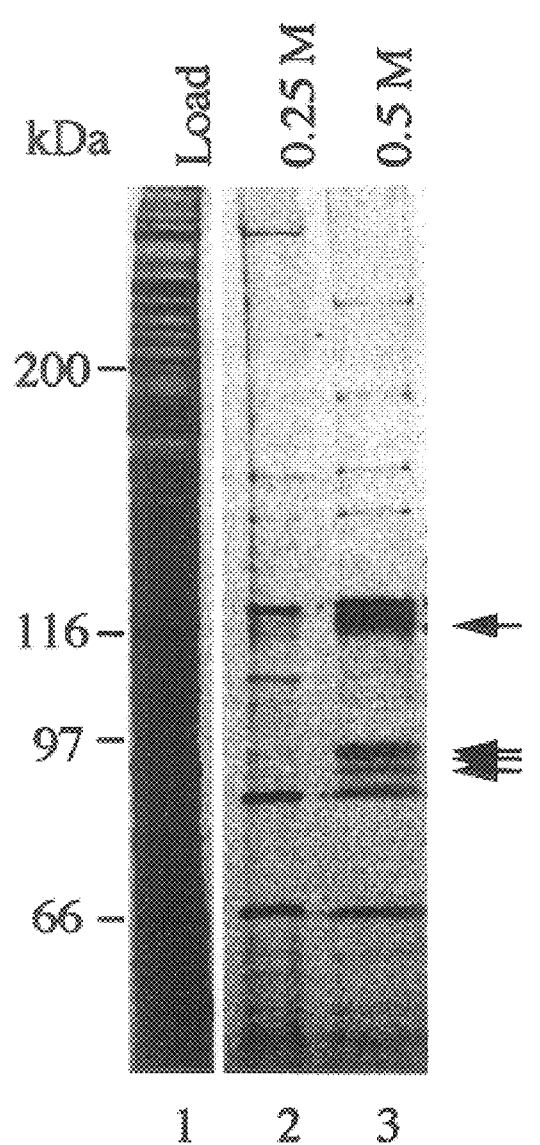
FIG. 4A is an autoradiograph showing purification of HIF-1 from $CoCl_2$-treated HeLa S3 cells. Flowthrough fraction from the M18 DNA column (Load, lane 1) and 0.25M KCl and 0.5M KCl fractions from the second W18 DNA affinity column (lanes 2 and 3) were analyzed. An aliquot of each fraction (5 ug of load or 1 ug of affinity column fractions) were resolved by 6% SDS-PAGE and silver stained. HIF-1 polypeptides in lanes 2 and 3 are indicated by arrows at the right of the figure.

The results of the final large scale purification are summarized in Table 1. From 120 liters of HeLa cells, approximately 60 u g of highly purified HIF-1 were obtained. The total purification was 11,250-fold and yielded approximately 22% of the starting of HIF-1 DNA binding activity. Our objective was to identify HIF-1 subunits and isolate HIF-1 components for the purpose of peptide mapping and protein microsequencing analysis. Since additional steps of purification resulted in markedly lower yield, we did not purify HIF-1 further to homogeneity. Aliquots from flowthrough of the M18 column (FIG. 4A, Load) as well as the 0.25M KCl wash and 0.5M KCl elute fractions of the second W18 column were analyzed by 6% SDS-PAGE and silver staining. Four polypeptides of 90–120 kDa were highly enriched in the 0.5M KCl fraction, which had high HIF-1 DNA binding activity compared with the 0.25M KCl fraction, which had very little HIF-1 activity. The 0.5M KCl fraction, however, still had many of the contaminant proteins found in the 0.25M KCl fraction.

Figure 4B:
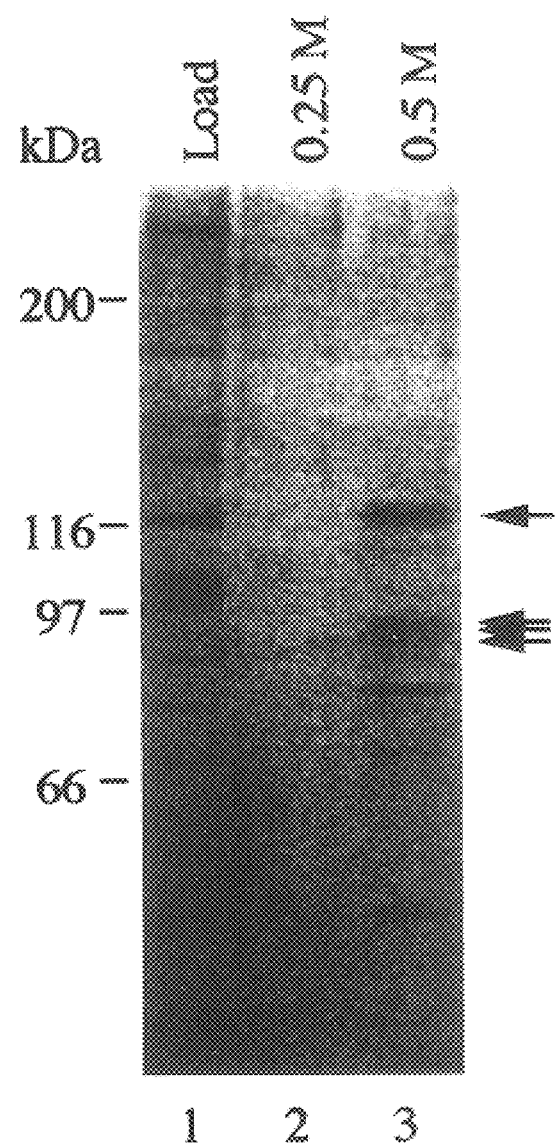
FIG. 4B is an autoradiograph showing HIF-1 purification from hypoxic Hep3B cells. HIF-1 fractions from the first W18 column (Load, lane 1) and 0.25M KCl and 0.5M KCl fractions from the second W18 column (lanes 2 and 3) were analyzed. An aliquot of each fraction (50 ul) was resolved by 7% SDS-PAGE and silver stained. Molecular mass markers are myosin (200 kDa), β-galactosidase (116 kDa), phosphorylase (97 kDa), BSA (66 kDa), and ovalbumin (45 kDa). HIF-1 polypeptides in lanes 2 and 3 are indicated by arrows at the right of the figure.

In an initial pilot purification of HIF-1 from hypoxia-induced Hep3B cells, a different purification protocol was used. Gel filtration over a Sephacryl S-300 column was also found to be effective in separating HIF-1 from constitutive DNA binding activity. In addition, a calf thymus DNA column was used to remove nonspecific DNA-binding proteins prior to two rounds of W18 DNA affinity chromatography. HIF-1 activity was detected in 0.5 M KCl fractions from both DNA affinity columns. An aliquot from the 0.5M KCl elute fraction of the first W18 column (FIG. 4B, Load) as well as the 0.25M KCl wash and 0.5M KCl elute fractions of the second W18 column were analyzed by 7% SDS-PAGE and silver staining. Four polypeptides of similar molecular mass to those that co-purified with HIF-1 DNA binding activity in $CoCl_2$-treated HeLa cells were present in the affinity-purified preparation from hypoxic Hep3B cells (FIG. 4B, lane 3, arrows), indicating that HIF-1 from the two different cell types is composed of the same polypeptide subunits. Affinity-purified HIF-1 from both $CoCl_2$-treated HeLa cells and hypoxic Hep3B cells bound specifically to the W18 probe in gel shift assays.

EXAMPLE 3

Analysis of HIF-1 Subunits

The following experiments were conducted to identify polypeptides that are part of the HIF-1 DNA binding complex.

Preparative gel shift assays were performed with 30 ul of affinity-purified HIF-1 and probe W18. Gel slices containing HIF-1 and surrounding areas were isolated after autoradiography with wet gel. Gel slices were placed on the stacking gel of a 6% SDS-polyacrylamide gel and incubated with Laemmli buffer in situ for 15 min, and electrophoresis was performed in parallel with 30 ul of affinity-purified HIF-1 and molecular weight markers. For two-dimensional denaturing gel electrophoresis, two aliquots of affinity-purified HIF-1 were resolved on a 6% SDS-polyacrylamide gel with 5% cross-linking (acrylamide/bisacrylamide ratio of 19:1). One lane was stained with silver nitrate. The gel slices corresponding to regions of interest were isolated from the unstained lane. The isolated gel slices were placed directly on the stacking gel of the second dimension 6% SDS-polyacrylamide gel with 3.2% cross-linking, and electrophoresis was performed in parallel with 30 ul of affinity purified HIF-1.

Peptide Mapping of HIF-1 Subunits 2 ml of the affinity-purified HIF-1 were dialyzed against 10 mM ammonium bicarbonate, 0.05% SDS and lyophilized. After resuspension in a solubilizing solution (100 mM sucrose, 3% SDS, 21.25 mM Tris-HCl (pH 6.9), 1 mM EDTA, 5% β-mercaptoethanol, 0.005% bromphenol blue), the protein samples were heated to 37° C. for 15 min and resolved on a 6% polyacrylamide gel containing 0.2% SDS. Polypeptides were transferred electrophoretically at 4° C. to a polyvinylidene difluoride membrane (Bio-Rad) in 0.5× Towbin buffer (Towbin et al. 91979) Proc. Natl. Acad. Sci. USA 76:4350–5354) (96 mM glycine, 12.5 mM Tris-HCl (pH 8.3)) with 10% acetic acid, destained with 5% acetic acid and rinsed with Milli-Q water. Membrane slices containing the HIF-1 polypeptides of 120, 94/93, and 91 kDa were excised and subjected to peptide mapping (Best et al. (1994) in Techniques in Protein Chemistry V (Crabb, J. W., ed.), pp. 205–213, Academic Press, San Diego, Calif.). In situ tryptic digestion and reverse phase HPLC were performed by the Wistar Protein Microchemistry Laboratory.

UV Cross-Linking Analysis

UV cross-linking was carried out as described (Wang & Semenza (1993) Proc. Natl. Acad. Sci. USA 90:4304–4308) except that 30 ul of affinity-purified HIF-1 were used in the binding reaction. Affinity-purified HIF-1 was incubated with W18 probe in the absence or presence of unlabeled W18 or M18 oligonucleotide. After incubation for 15 min at 4° C., the reaction mixtures were irradiated with UV light (312 nm; Fisher Scientific) for 30 min and resolved by 6% SDS-PAGE with pre-stained molecular weight markers and visualized by autoradiography.

Glycerol Gradient Sedimentation

Linear gradients of 12 ml, 10–30% glycerol in a buffer containing 100 mM KCl, 25 mM Tris-HCl (pH 7.6), 0.2 mM EDTA, 5 mM DTT, and 0.4 mM phenylmethylsulfonyl fluoride, were prepared for centrifugation in a Beckman SW40 rotor for 48 h at 4° C. Nuclear extract prepared from hypoxic Hep3B cells (100 ul, 5 mg/ml) was mixed with an equal volume of glycerol gradient buffer containing 10% glycerol and layered on the top of the gradient. A marker gradient was sedimented in parallel and contained 50 ug each of thyroglobulin (660 kDa), ferritin (440 kDa), catalase (232 kDa), aldolase (158 kDa), and BSA (67 kDa) (Pharmacia). Markers were adjusted to the same volume and glycerol concentration as the sample. Fractions (0.5 ml) were collected from the top of the tubes, and DNA binding activity was measured by the gel shift assay. Markers were assayed by SDS-PAGE and silver staining.

Results

Figure 5A:
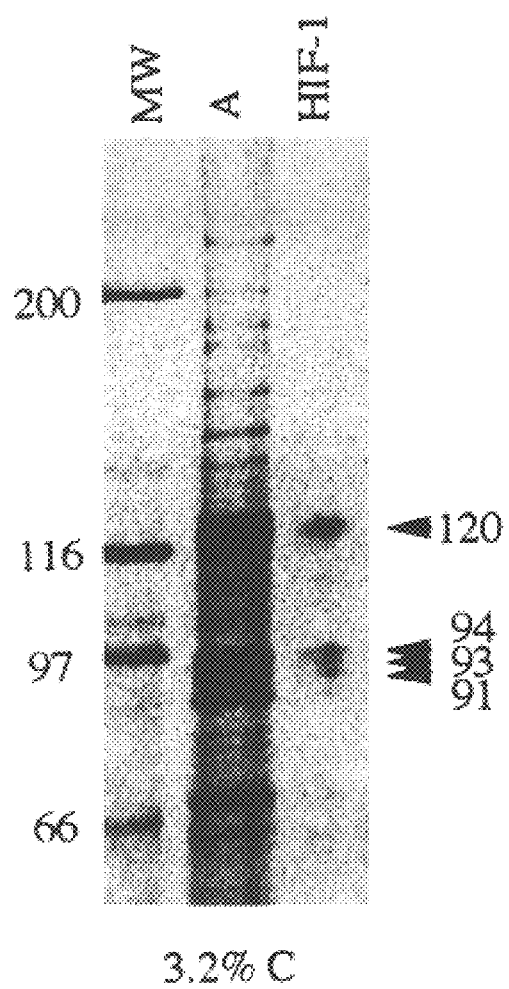
FIG. 5A is an autoradiograph identifying the HIF-1 polypeptides. An aliquot of affinity-purified HIF-1 was resolved on a 6% SDS-polyacrylamide gel with 3.2% cross-linking along with the HIF-1 protein complex isolated by preparative native gel shift assay (HIF-1). MW, molecular mass markers with size (kDa) indicated at left of figure; numbers to the right of figure indicate the apparent molecular weights (kDa) of HIF-1 polypeptides.

In order to identify polypeptides that are part of the HIF-1 DNA binding complex, preparative gel shift assays were performed with affinity-purified HIF-1 and W18 probe. Gel slices containing the HIF-1-DNA complex were isolated, inserted directly into the wells of an SDS-polyacrylamide gel, and analyzed by electrophoresis in parallel with an aliquot of affinity-purified HIF-1 (FIG. 5A). Four polypeptides present in the HIF-1 complex migrated with an apparent molecular weight of 120, 94, 93, and 91 kDa, respectively (FIG. 5A, HIF-1). None of these peptides were detected in gel slices isolated from other regions of the same lane. These four polypeptides migrated at the same positions as the polypeptides that co-purified with HIF-1 DNA binding activity by DNA affinity chromatography (FIG. 5A, lane A). The 120 kDa polypeptide and the 91–94 kDa polypeptides appear to be present in an equimolar ratio, suggesting that the 120 kDa polypeptide forms complexes with any one of the 91-, 93-, and 94 kDa polypeptides.

Figure 5B:
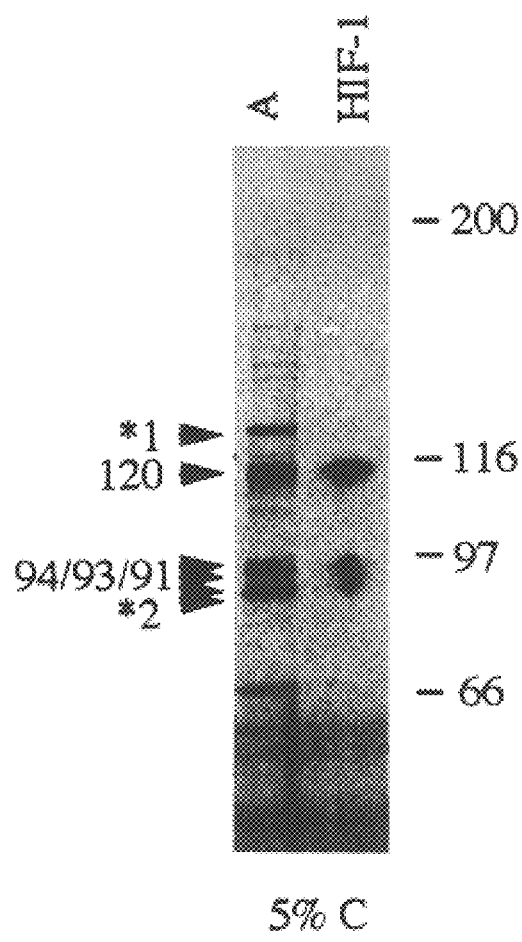
FIG. 5B is an autoradiograph showing the HIF-1 components on a 6% SDS-polyacrylamide gel with 5% cross-linking. An aliquot of affinity-purified HIF-1 was resolved on a 6% SDS-polyacrylamide gel along with the HIF-1 protein complex isolated by preparative native gel shift assay (HIF-1). The 120 kDa polypeptide, 94/93/91 kDa polypeptides, and two contaminant proteins (*1 and *2) are indicated.

On a 6% SDS-polyacrylamide gel with 3.2% cross-linking, the 120 kDa HIF-1 polypeptide migrated very close to a contaminant polypeptide of slightly greater apparent molecular weight (FIG. 5A, lane A), making isolation of the 120 kDa polypeptide difficult. This problem was resolved by separating the HIF-1 polypeptides on a 6% SDS-polyacrylamide gel with 5% cross-linking. The 120 kDa polypeptide migrated much faster on the more highly cross-linked gel relative to the migration of the 116 kDa molecular mass marker, whereas migration of the contaminant band (*1) was unchanged (FIG. 5B, lane A). Under these conditions, however, the 91 kDa polypeptide ran very close to another contaminant band (*2) below it. Two polyacrylamide gel systems with different degrees of cross-linking were therefore required for the isolation of the 91–94 kDa and the 120 kDa HIF-1 polypeptides, respectively.

Figure 5C:
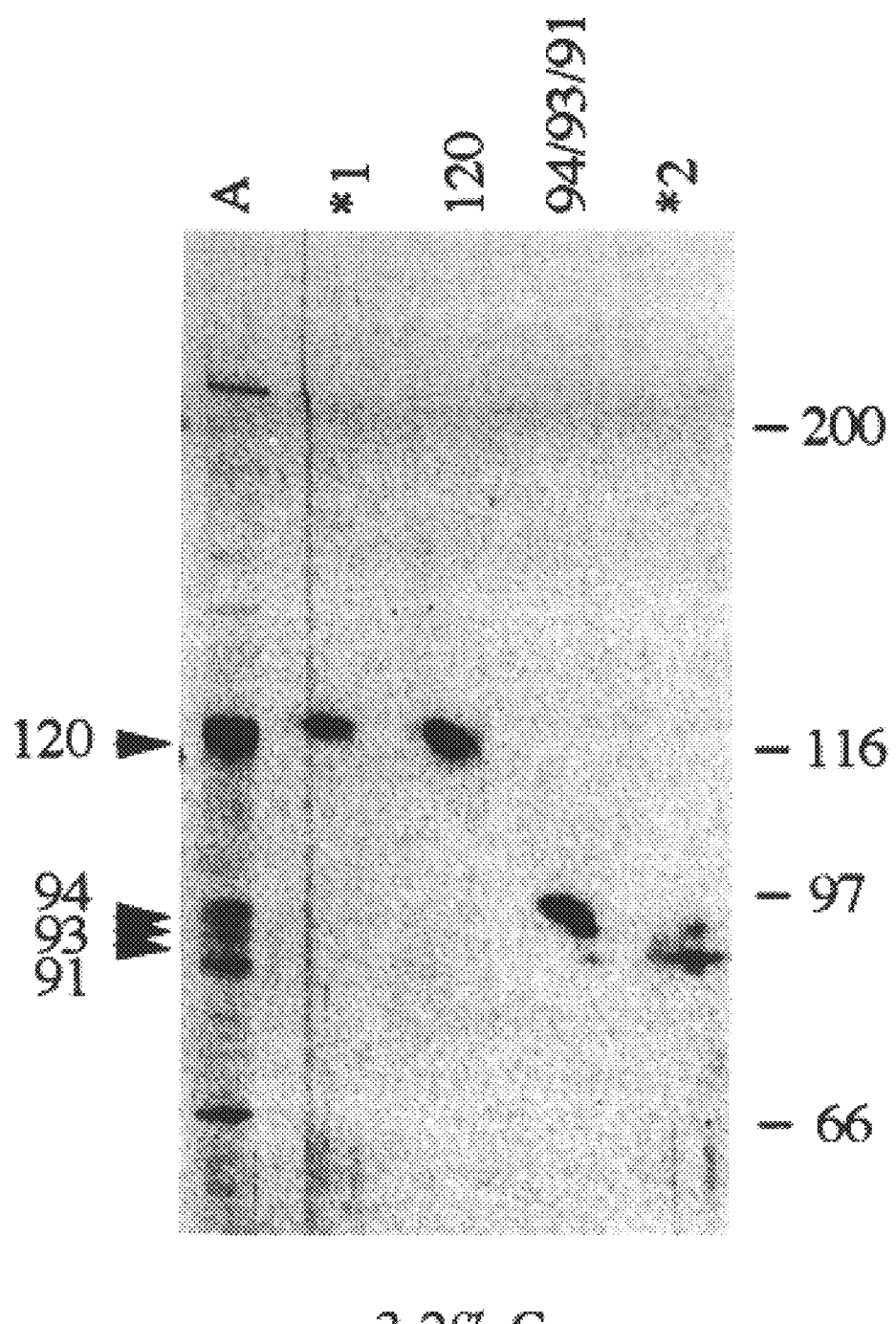
FIG. 5C is an autoradiograph showing the alignment of HIF-1 components identified on two gel systems with different degrees of cross-linking. Gel slices isolated from the 6% SDS-polyacrylamide gel with 5% cross-linking corresponding to 120 kDa HIF-1 polypeptide (12), 94/93/91 kDa HIF-1 polypeptide (94/93/91), and two contaminant proteins (*1 and *2) were resolved on a 6% SDS-polyacrylamide gel with 3.2% cross-linking in parallel with an aliquot (30 ul) of affinity purified HIF-1 (FIG. 5A).

To confirm that the HIF-1 polypeptides identified by the two gel systems were identical, two dimensional denaturing gel electrophoresis was performed. Affinity-purified HIF-1 was first resolved on a 6% SDS-polyacrylamide gel with 5% crosslinking (as in FIG. 5B, lane A). Regions of the gel containing the 120 kDa, 94/93/91-kDa HIF-1 polypeptides, as well as the two contaminant bands, were isolated and analyzed by electro-phoresis on a 6% SDS-polyacrylamide gel with 3.2% cross-linking in parallel with an aliquot of the affinity-purified HIF-1. As shown in FIG. 5C, the isolated HIF-1 and contaminant polypeptides co-migrate with the corresponding bands in the control sample, indicating that the differences in their migration were due to different degrees of cross-linking of the SDS-polyacrylamide gels.

Figure 6:
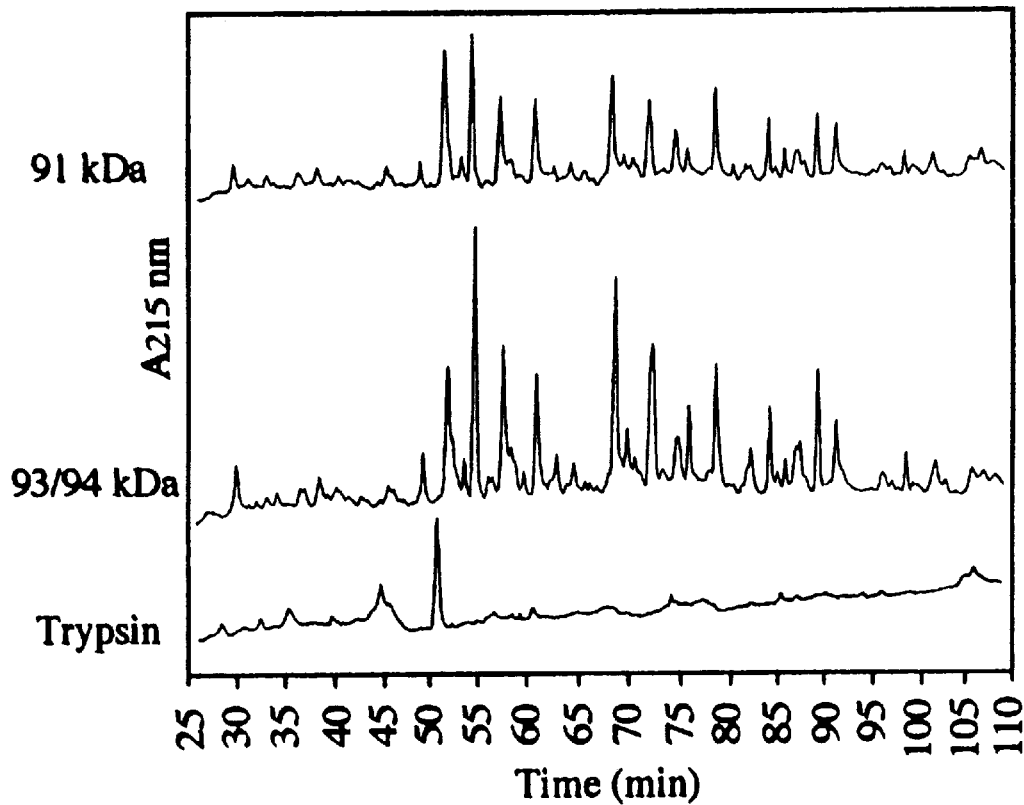
FIG. 6 is a graph of the absorbance profiles at 215 nm of tryptic peptides derived from 91 kDa HIF-1 polypeptide (top), 93/94 kDa polypeptides (middle), and trypsin (bottom).

To determine whether the four polypeptides from the HIF-1 complex represent distinct protein species, tryptic peptide mapping was performed. The 91 kDa band was isolated individually while the 93 and 94 kDa bands were excised together after electrophoretic separation and transfer to a polyvinylidene difluoride membrane. Proteins were digested with trypsin in situ, and the tryptic peptides were separated by reverse phase HPLC (FIG. 6). The elution profiles of tryptic peptides derived from 91 kDa protein and 93/94 kDa proteins were nearly superimposable (FIG. 6), suggesting that they were derived from similar polypeptides. Another aliquot of HIF-1 was resolved on a 6% polyacrylamide gel of 5% crosslinking for isolation of the 120 kDa HIF-1 polypeptide. The tryptic peptide elution profile derived from the 120 kDa polypeptide was distinct from those of the 91–94 kDa polypeptides. These results suggest that HIF-1 is composed of two different subunits, 120 kDa HIF-1α and 91/93/94 kDa HIF-1β.

Figure 7:
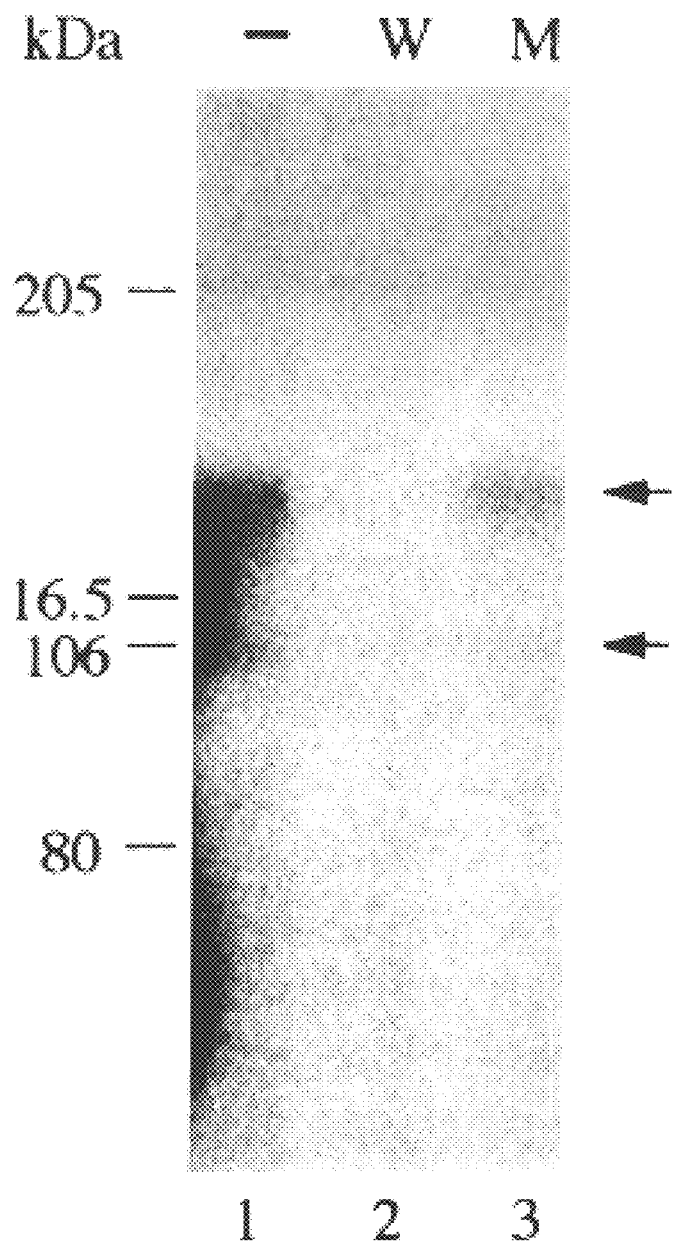
FIG. 7 is an autoradiograph showing UV cross-linking analysis with affinity purified HIF-1 and probe W18 in the absence (lane 1) or presence of 250-fold molar excess of unlabeled W18 (lane 2) or M18 (lane 3) oligonucleotide. The binding reaction mixtures were UV-irradiated and analyzed on a 6% SDS-polyacrylamide gel. Molecular mass standards are indicated at left.

To identify the DNA-binding subunit(s), affinity-purified HIF-1 was incubated with W18 probe. After UV irradiation to cross-link the DNA-binding proteins to nucleotide residues at the binding site, the reaction mixtures were boiled in Laemmli buffer and resolved by SDS-PAGE, and cross-linked proteins were visualized by autoradiography. Two DNA-binding proteins were detected (FIG. 7, lane 1). Their molecular masses were estimated to be approximately 120 and 92 kDa (after the 16 kDa molecular mass contributed by probe DNA was subtracted), similar to those of HIF-1α and HIF-1β. The binding of both proteins to the probe was sequence-specific since it could be competed by unlabeled wild-type W18 (FIG. 7, lane 2) but not mutant M18 (FIG. 7, lane 3) oligonucleotide. These results suggest that both HIF-1α and HIF-1β contact DNA directly. HIF-1α was cross-linked to DNA much more strongly than HIF-1β (FIG. 7, lanes 1 and 3). These data provided further evidence that the four polypeptides purified by DNA affinity chromatography are bona fide components of HIF-1 DNA binding activity.

Figure 8:
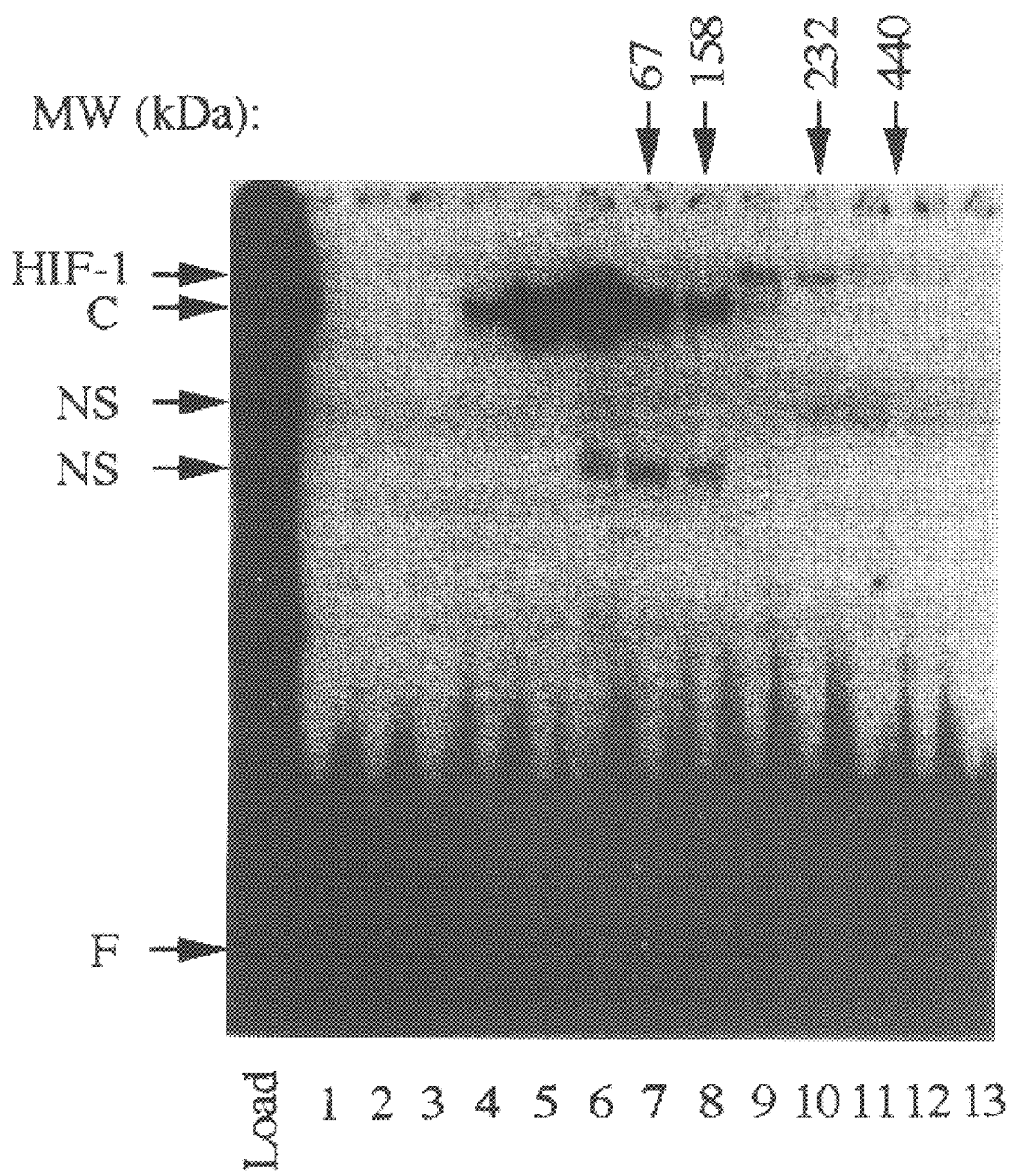
FIG. 8 is an autoradiograph showing the results of glycerol gradient sedimentation analysis. Nuclear extracts prepared from Hep3B cells exposed to 1% $O_2$ for 4 h (Load) was sedimented through a 10–30% linear glycerol gradient. Aliquots (10 ul) from each fraction were analyzed by gel shift assay. Arrows at top indicate the peak migration for ferritin (440 kDa), catalase (232 kDa), aldolase (158 kDa), and BSA (67 kDa).

To estimate the native size of HIF-1, glycerol gradient sedimentation analysis was performed with crude nuclear extract prepared from hypoxic Hep3B cells. HIF-1 and the constitutive DNA binding activity were monitored by gel shift assays. In hypoxic Hep3B nuclear extracts, HIF-1-DNA complexes are present in two forms, whereas in $CoCl_2$-treated HeLa extracts, the faster migrating form predominates. The results, shown in FIG. 8, demonstrate that the two bands of the HIF-1 doublet are separable by sedimentation. The faster migrating form was estimated to have a molecular mass of approximately 200–220 kDa. Longer exposure of the autoradiograph revealed that the slower migrating band co-migrated with ferritin, which has a molecular mass of 440 kDa. Assuming a globular conformation for both protein complexes, these results are consistent with the hypothesis that the faster migrating form represents a heterodimeric complex, consisting of a 120 kDa HIF-1α subunit and a 91–94 kDa HIF-1β subunit, whereas the slower migrating form may represent a heterotetramer. The exact nature and stoichiometry of these HIF-1 complexes, however, remains to be determined. The constitutive DNA binding activity has a molecular mass less than the 67 kDa BSA protein. Since UV cross-linking analysis indicated that the constitutive factor has a DNA-binding subunit of approximately 40–50 kDa, it is most likely that the constitutive factor binds DNA as a monomer. Consistent with the results of glycerol gradient sedimentation analysis, HIF-1 eluted from a Sephacryl S-300 gel filtration column before the constitutive binding activity, and the slower migrating HIF-1 gel shift activity eluted before the faster migrating form. These results suggest that HIF-1 exists predominantly as a heterodimer in solution and to a lesser extent as a higher order complex, and that these complexes contain at least one HIF-1α and one HIF-1β subunit.

EXAMPLE 4

Isolation and Characterization of HIF-1α cDNA Sequences

Protein Microseauence Analysis

Purified HIF-1 subunits were fractionated by SDS-polyacrylamide gel electrophoresis, and the 120 and 94 kDa polypeptides were transferred to polyvinylidene difluoride membranes, individually digested with trypsin in situ and peptides were fractionated by reverse-phase high-pressure liquid chromatography (Wang & Semenza (1995) J. Biol. Chem. 270:1230–1237, herein specifically incorporated by reference). Protein microsequence analysis was performed at the Wistar Protein Microchemistry Laboratory, Philadelphia (Best et al. (1994) supra).

cDNA Library Construction and Screening

Poly (A)+RNA was isolated from Hep3B cells cultured for 16 h at 37° C. in a chamber flushed with 1% $O_2$/5% $CO_2$/balance $N_2$. cDNA was synthesized using oligo(dT) and random hexamer primers and bacteriophage libraries were constructed in λt11 and Uni-ZAP XR (Stratagene, La Jolla, Calif.). cDNA libraries were screened with $^{32}$P-labelled cDNA fragments by plaque hybridization as described (Sambrook et al. (1989) Molecular Cloning: A Laboratory Manual, 2nd Ed.; Cold Spring Harbor Laboratory Press, Plainview, N.Y., herein specifically incorporated by reference).

PCR

Degenerate oligonucleotides primers were designed using codon preference rules (Lathe (1985) J. Mol. Biol. 183:1–12). αF1 (5'-ATCGGATCCATCACIGA(A/G)CT(C/G)ATGGGITATA-3') (SEQ ID NO:7) was based upon the amino terminus of HIF-1α peptide 87-1 and used as a forward primer. Two nested reverse primers, αR1 (5'-ATTAAGCmTGGT(G/C)AGGTGGTCI(G/C)(A/T)GTC-3') (SEQ ID NO:8) and αR2 (5'-ATTAAGCTTGCATGGTAGTA(T/C)TCATAGAT-3') (SEQ ID NO:9), were based upon the carboxy terminus of peptide 91-1. PCR was performed by: denaturation of 108 phage or 10 ng of phage DNA at 95° C. for 10 min; addition of AmpliTaq (Perkin-Elmer) at 80° C.; and amplification for 3 cycles at 95° C., 37° C., and 72° C. (30 sec each) followed by 35 cycles at 95° C., 50° C., and 72° C. (30 sec each). Nested PCR with αF1/αR1 and then αF1/αR2 generated an 86-bp fragment which was cloned into pGEM4 (Promega). For HIF-1β (ARNT), PCR was performed as described above using primers 5'-ATAAAGCTTGT(C/G)TA(C/T)GT(C/G)TCIGA(C/T)TCIG-3' (SEQ ID NO:10) and 5'-ATCGAATTC(C/T)TCI-GACTGIGGCTGGTT-3' (SEQ ID NO:11) which resulted in the predicted 69-bp product. For analysis of the 5' end of HIP-1β (ARNT), Hep3B poly(A)+RNA was reverse-transcribed using reagents from a 5'-RACE kit (Clontech). The cDNA was used as template to amplify nt 54-425 of ARNT cDNA (Hoffman et al. (1991) supra), with 5'-TACGGATCCGCCATGGCGGCGACT-ACTGA-3' (SEQ ID NO:12) (forward primer) and nested reverse primers 5'-AGCCAGGGCACTACAGGTGGGTACC-3' (SEQ ID NO:13) and 5'-GTTCCCCGCAAGGACTTCATGTGAG-3' (SEQ ID NO:14) for 35 cycles at 95° C., 60° C., and 72° C. (30 sec each). PCR products were cloned into pGEM4 for nucleotide sequence analysis.

Results

The purified 120 kDa HIF-1α polypeptide was digested with trypsin, peptides were fractionated by reverse-phase high-pressure liquid chromatography and fractions 87 and 92 were subjected to microsequencing. Each fraction contained two tryptic peptides, for which virtually complete amino acid sequences were obtained: ITELMGYE-PEELLGR (SEQ ID NO:15) (87-1), XIILIPSDLAXR (SEQ ID NO:16) (87-2), SIYEYYHALDSDHLTK (SEQ ID NO:17) (91-1), and SFFLR (SEQ ID NO:18) (91-2). When 87-1 and 91-1 were entered as contiguous sequences, database searches identified similarities to the Drosophila proteins period (PER) and single-minded (SIM), and the mammalian aryl hydrocarbon receptor (AHR) and aryl hydrocarbon receptor nuclear translocator (ARNT) proteins, which all contain sequences of 200–350 amino acids that constitute the PAS (PER-ARNT-AHR-SIM) domain (Hoffman et al. (1991) Science 252:954–958; Citri et al. (1987) Nature 326:42–47; Burbach et al. (1992) Proc. Natl. Acad. Sci. USA 89:8185–8189; Crews et al. (1988) Cell 52:143–151; Nambu et al. (1991) Cell 67:1157–1167). Degenerate oligonucleotides were synthesized based upon the 87-1 and 91-1 sequences and used for PCR with cDNA prepared from hypoxic Hep3B cells. Nucleotide sequence analysis revealed that the cloned PCR product-encoded the predicted amino acids, demonstrating that 87-1 and 91-1 were contiguous peptides.

EXAMPLE 5

Nucleotide Sequence and Database Analysis

Complete unambiguous double stranded nucleotide sequences were obtained by incorporation of fluorescence-labeled dideoxy nucleotides into thermal-cycle sequencing reactions using T3, T7, and custom-synthesized primers. Reactions were performed using Applied Biosystems 394 DNA Synthesizers and 373a Automated DNA Sequencers in the Genetics Core Resources Facility of The Johns Hopkins University. Protein and nucleic acid database searches were performed at the National Center for Biotechnology Information using the programs BLASTP and TBLASTN (Altschul et al. (1990) J. Mol. Biol. 215:403–410). The HIF-1α cDNA nucleotide sequence and deduced amino acid sequence have been submitted to GenBank. The accession number is U22431.

Results

Figure 9:
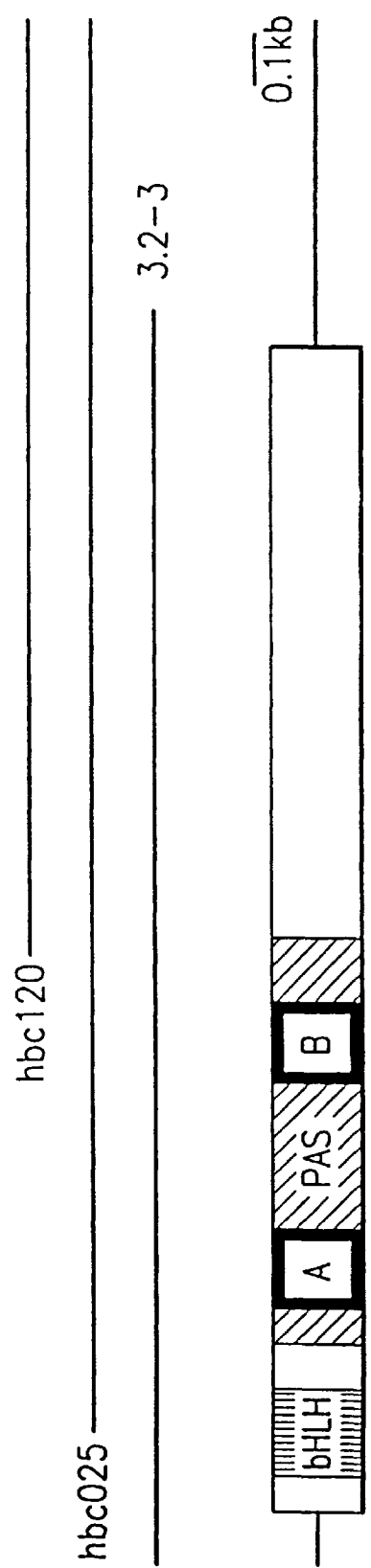
FIG. 9 is a diagram of the cDNA sequence encoding HIF-1α. Bold lines indicate extent of clones hbc120, hbc025, and 3.2–3 relative to the full-length RNA-coding sequence shown below. Box, amino acid coding sequences; thin line, untranslated sequences; bHLH, basic helix-loop-helix domain; A and B, internal homology units within the PAS domain.

Database analysis also identified an expressed-sequence tag (EST) whose derived amino acid sequence showed similarity to bHLH-PAS proteins. We obtained the 3.6-kb cDNA from which the EST was derived, hbc$_{025}$ (Takeda et al. (1993) Hum. Mol. Genet. 2:1793–1798). Complete nucleotide sequence analysis revealed that it encoded all four tryptic peptides. Another EST was identified which shared identity with hbc025 and was encoded by a 2.0-kb cDNA, hbc120 (Takeda et al. (1993) supra). Sequence analysis of hbc120 revealed that it was co-linear with the 3' end of hbc025 (FIG. 9), differing only in the length of the poly (A) tail. The 5' end of hbc025 was used to screen a Hep3B cDNA library, resulting in the isolation of an overlapping 3.4-kb CDNA, 3.2–3, which extended to an initiator codon. The composite cDNA of 3720 bp encoded a 2478-bp open reading frame that included a translation initiation codon, a 28-bp 5'-untranslated region (5'-UTR) that contained an in-frame termination codon, and a 1211-bp 3'-UTR that ended with a canonical polyadenylation signal followed after 12 bp by 43 adenine residues. Compared to the consensus translation-initiation sequence GCC(A/G)CCATGG (SEQ ID NO:19) (Kozak (1987) Nucleic Acids Res. 15:8125–8132), the HIF-1α cDNA sequence is TTCACCATGG (SEQ ID NO:20). The HIF-1α cDNA open reading frame predicted a novel 826 amino acid polypeptide (FIG. 10) with a molecular mass of 93 kDa that contained a bHLH-PAS domain at its amino terminus.

Analysis of two tryptic peptides isolated from the 94 kDa HIF-1α polypeptide (Wang & Semenza (1995) supra) yielded partial amino acid sequences, VVYVSDSVTPVL-NQPQSE (SEQ ID NO:21) and TSQFGVGSFQTPSSF-SSMXLPGAPTASPGAAAY (SEQ ID NO:22). Using degenerate oligonucleotides based upon the second peptide sequence, a PCR product of the predicted size was amplified from Hep3B cDNA. Database searches identified both peptides within the sequence of ARNT, a bHLH-PAS protein previously shown to heterodimerize with AHR to form the functional dioxin receptor (Reyes et al. (1992) Science 256:1193–1195). Two isoforms of ARNT have been identified which differ by the presence or absence of a 15 amino acid sequence encoded by a 45-bp alternative exon (Hoffman et al. (1991) supra). Analysis of Hep3B RNA by reverse transcriptase-PCR revealed the presence of both sequences, as well as additional isoforms. These primary sequence differences may account for the purification of three (91,93, and 94 kDa) HIF-1β polypeptides (Wang & Semenza (1995) supra). The apparent molecular mass of both HIF-1α and HIF-1β on denaturing gels was greater than the mass predicted from the cDNA sequence. For HIF-1α the apparent mass was 120 kDa compared to a calculated mass of 93 kDa; for the HIF-1β subunits, the apparent masses were 91–94 kDa compared to calculated masses of 85 and 87 kDa for the 774 and 789 amino acid isoforms of ARNT, respectively. The HIF-1α and ARNT sequences contain multiple consensus sites for protein phosphorylation and HIF-1 has been shown to require phosphorylation for DNA binding (Wang & Semenza (1993b) supra).

HIF-1α and HIF-1β (ARNT) belong to different classes of bHLH domains, which consist of contiguous DNA binding (b) and dimerization (HLH) motifs. The bHLH domain of HIF-1α is most similar to the other bHLHPAS proteins, SIM and AHR (FIG. 11). HIF-1β (ARNT) has greatest similarity to the bHLH domains found in a series of mammalian (MI, USF, L-MYC) and yeast (CP-1) proteins that bind to 5'-CACGTG-3' (SEQ ID NO:23) (Dang et al. (1992) Proc. Natl. Acad. Sci. USA 89:599–603), a sequence which resembles the HIF-1 [5'-(G/Y)ACGTGC(G/T)-3' (SEQ ID NO:24) (Semenza et al. (1994) supra)] and dioxin receptor [5'-(TIG)NGCGTG(A/C)-(G/C)A-3 ' (SEQ ID NO:25) (Lusska et al. (1993) J. Biol Chem. 268:6575–6580)] binding sites. These transcription factors share bHLH domains of related sequence which occur in different dimerization contexts: MI, L-MYC, and USF are bHLH-leucine zipper proteins, ARNT is a bHLH-PAS protein, and CP-1 contains only a bHLH domain.

Analysis of PAS domains, which have been implicated in both ligand binding and protein dimerization (Huang et al. (1993) Nature 364:259–262; Dolwick et al. (1993) Proc.

Natl. Acad. Sci. USA 90:8566–8570; Reisz-Porszasz et al. (1994) Mol. Cell. Biol. 14:6075–6086), revealed that HIF-1α is most similar to SIM. Our alignment established consensus sequences that include a previously unreported motif, HXXD, present in the A and B repeats of all PAS proteins (FIG. 12). We also found that KinA of *Bacillus subtilis* (Perego et al. (1989) J. Bacteriol. 171:6187–6196) contains a PAS domain at its amino terminus and is thus the first procaryotic member of this protein family, indicating a remarkable degree of evolutionary conservation. KinA, like PER, possesses a PAS but not a bHLH domain and is thus unlikely to bind DNA. *B. subtilis* undergoes sporulation in response to adverse environmental conditions and KinA functions as a sensor that transmits signals via a carboxy-terminal kinase domain (Burbulys et al. (1991) Cell 64, 545–552).

EXAMPLE 6

RNA Blot Hybridization

The expression of HIF-1 RNAs in response to inducers of HIF-1 DNA-binding activity was analyzed as follows.

Total RNA (15 ug) was fractionated by 2.2M formaldehyde/ 1.4% agarose gel electrophoresis, transferred to nitrocellulose membranes and hybridized at 68° C. in Quik-Hyb (Stratagene) to $^{32}$P-labelled HIF-1α or ARNT cDNA. Gels were stained with ethidium bromide and RNA was visualized by ultraviolet illumination before and after transfer to insure equal loading and transfer, respectively, in each lane. Based upon the migration of RNA size markers (BRL-GIBCO) on the same gels, the size of HIF-1α RNA was estimated to be 3.7 t 0.1 kb. Two ARNT RNA species were identified as previously reported (Hoffman et al. (1991) supra).

Results

When Hep3B cells were exposed to 1% $O_2$, HIF-1α and HIF-1β (ARNT) RNA levels peaked at 1–2 h, declined to near basal levels at 8 h, and showed a secondary increase at 16 h of continuous hypoxia (FIG. 13A). In response to 75 uM $CoCl_2$, HIF-1 RNAs peaked at 4 h, declined at 8 h, and increased again at 16 h (FIG. 13B). In cells treated with 130 uM desferrioxamine, a single peak at 1–2 h was seen (FIG. 13C). When cells were incubated at 1% $O_2$ for 4 h and then returned to 20% $O_2$, both HIF-1α and HIF-1β RNA decreased to below basal levels within 5 min, the earliest time point assayed (FIG. 13D). These results demonstrate that, as in the case of HIF-1 DNA-binding activity (Wang & Semenza (1993b) supra), HIF-1 RNA levels are tightly regulated by cellular $O_2$ tension. The marked instability of HIF-1α RNA in posthypoxic cells may involve the 3'-untranslated region (3'-UTR) which contains eight AUUUA sequences (FIG. 13E) that have been identified in RNAs with short half-lives and shown to have a destabilizing effect when introduced into heterologous RNAs (Shaw & Kamen (1986) Cell 46:659–667). Seven of the HIF-1α AUUUA sequences conform to a more stringent consensus for RNA instability elements, 5'-UUAUUUA(U/A)(U/A)-3' (SEQ ID NO:26) (Lagnado et al. (1994) Mol. Cell. Biol. 14:7984–7995).

EXAMPLE 7

Antibody Production

To analyze HIF-1 protein expression, polyclonal antisera was raised against HIF-1α and HIF-1β as follows.

Rabbits were immunized with recombinant proteins in which glutathione-S-transferase (GST) was fused to amino acids 329–531 of HIF-1α or 496–789 of ARNT. To generate antibodies against HIF-1α, a 0.6 kb EcoRI fragment from hbc025 was cloned into pGEX-3X (Pharmacia) and transformed into *E. coli* DH5α cells (GIBCO-BRL). GST/HIF-1α fusion protein was isolated by exposure of bacteria ($OD_{600}$=0.8) to 0.1 MM IPTG at room temperature for 1 h; sonication in 50 mM Tris-HCl (pH 7.4), 1 mnM EDTA, 1 mnM EGTA, 1 mM phenylmethylsulfonyl fluoride; centrifugation at 10,000×g for 10 min; incubation of supernatant with glutathione-agarose (Pharmacia) in the presence of 1% NP-40 for 1 h at 4° C.; and elution with 5 mM reduced glutathione, 50 mM Tris-HCl (pH 8.0), 150 mM NaCl. To generate antibodies against HIF-1β, ARNT nt 1542-2428 were amplified from Hep3B cDNA by PCR with Taq polymerase using forward primer 5'-ATAGGATCCTCAGGTCAGCTGGCACCCAG-3' (SEQ ID NO:27) and reverse primer 5'-CCAAAGCTTCTATTCTGAAAAGGGGGG-3' (SEQ ID NO:28). The product was digested with BamHI and EcoRI, to generate a fragment corresponding to ARNT nt 1542-2387, and cloned into pGEX-2T (Pharmacia). Fusion protein isolation was as described above, except that induction was with 1 mM IPTG for 2 h and binding to glutathione-agarose was in the presence of 1% Triton X-100 rather than NP-40. Fusion proteins were excised from 10% SDS/ polyacrylamide gels and used to immunize New Zealand white rabbits (HRP Inc., Denver Pa.) according to an institutionally-approved protocol. Antibodies raised against HIF-1α were affinity-purified by binding to GST/HIF-1α coupled to CNBr-activated Sepharose 4B (Pharmacia).

Results

Figure 14A:
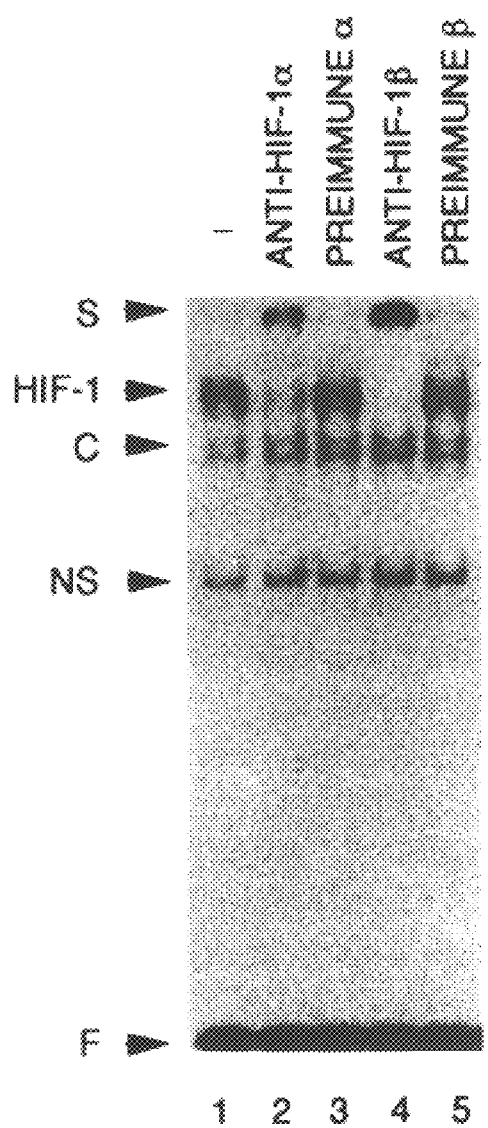
FIG. 14A is an autoradiograph of nuclear extracts from hypoxic Hep3B cells incubated with oligonucleotide probe W18 for 10 min on ice, immune sera was added (lanes 2 and 5) and incubated for 20 min on ice, followed by polyacrylamide gel electrophoresis. Preimmune sera (lanes 3 and 5) and antisera (lanes 2 and 4) were obtained from rabbits before and after immunization, respectively, with GST/HIF-1α (lanes 2 and 3) or GST/HIF-1β (lanes 4 and 5). HIF-1, constitutive (C) and nonspecific (NS) DNA binding activities, free probe (F), and supershifted HIF-1/DNA/antibody complex (S) are indicated.

Antisera was used to demonstrate that the proteins encoded by the cloned HIF-1α cDNA and ARNT are components of HIF-I DNA-binding activity (FIG. 14A). When crude nuclear extracts from hypoxic cells were incubated with probe DNA and either antiserum, the HIF-1/DNA complex seen in the absence of antisera was replaced by a more slowly migrating HIF-1/DNA/antibody complex, whereas addition of preimmune sera had no effect on the HIF-1/DNA complex.

EXAMPLE 8

Immunoblot Analysis 15 ug aliquots of nuclear protein extracts were resolved on 6% SDS/polyacrylamide gels and transferred to nitrocellulose membranes in 20 mM Tris-HCl (pH 8.0), 150 mM glycine, 20% methanol. Membranes were blocked with 5% milk/TBS-T [20 mM Tris-HCl (pH 7.6), 137 mM NaCl, 0.1% Tween-20], incubated with affinity-purified HIF-1α antibodies or HIF-1β antiserum diluted 1:400 or 1:5000, respectively, washed, incubated with horseradish peroxidase anti-immunoglobulin conjugate diluted 1:5000, washed, and developed with ECL reagents (Amersham) and autoradiography. Incubations were for 1 h in 5% milk/TBS-T and washes were for a total of 30 min in TBS-T at room temperature.

Results

Figure 14B:
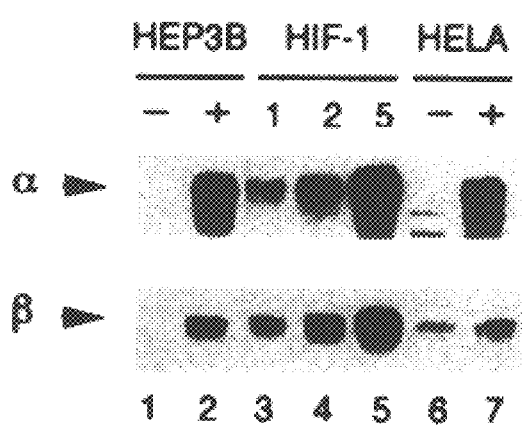
FIG. 14B is an immunoblot showing antisera recognition of HIF-1 subunits present in purified protein preparations and crude protein extracts. Nuclear extracts from Hep3B cells which were untreated (lane 1) or exposed to 1% O₂ for 4 h (lane 2) and from HeLa cells which were untreated (lane 6) or exposed to 75 uM CoCl₂ for 4 h (lane 7) were fractionated on a 6% SDS/polyacrylamide gel in parallel with 1, 2, and 5 ul of affinity-purified HIF-1 from CoCl₂-treated HeLa cells (lanes 3–5). Protein was transferred to a nitrocellulose membrane and incubated with antisera to HIF-1α (top) or HIF-1β (bottom).
Figure 14C:
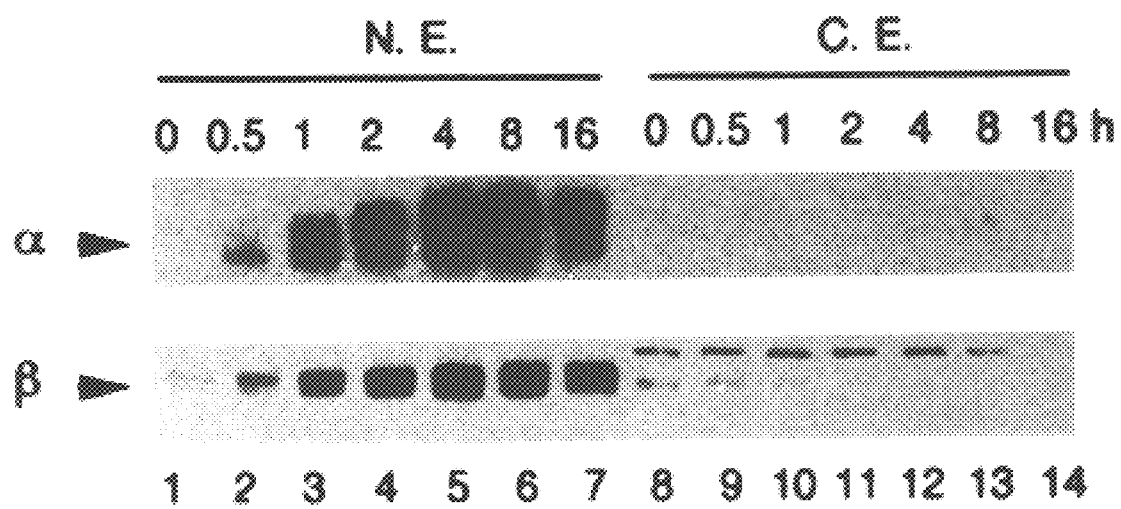
FIG. 14C is an immunoblot showing the induction kinetics of HIF-1α and HIF-1β protein in hypoxic cells. Hep3B cells were exposed to 1% O₂ for 0 to 16 h prior to preparation of nuclear (N.E.) and cytoplasmic (C.E.) extracts, and immunoblot analysis was performed with antisera to HIF-1α (top) or HIF-1β (bottom).
Figure 14D:
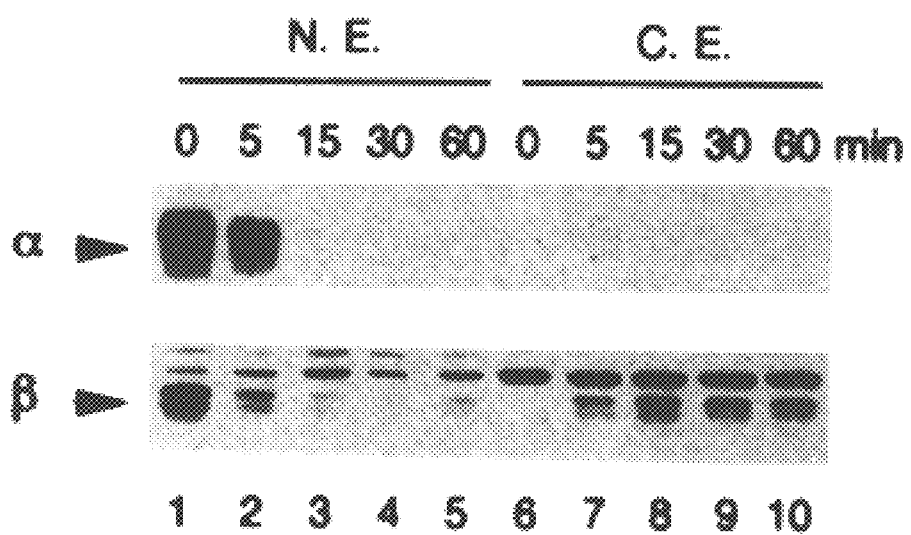
FIG. 14D is an immunoblot showing decay kinetics of HIF-1α and HIF-1β polypeptides in post-hypoxic cells. Hep3B cells were exposed to 1% O₂ for 4 h and returned to 20% O₂ for 0 to 60 min prior to preparation of extracts and immunoblot analysis. Arrowheads distinguish HIF-1 subunits from cross-reacting proteins of unknown identity.

Immunoblot analysis revealed that the antisera detected polypeptides in crude nuclear extracts from hypoxic Hep3B or $CoCl_2$-treated HeLa cells which co-migrated with polypeptides present in purified HIF-1 protein preparations (FIG. 14B). Analysis of nuclear and cytoplasmic extracts prepared from Hep3B cells exposed to 1% $O_2$ (FIG. 14C) revealed that peak levels of HIF-1α and HIF-1β were present in nuclear extracts at 4–8 h of continuous hypoxia, similar to the induction kinetics of HIF-1 DNA-binding activity (Wang & Semenza (1993) J. Biol. Chem. 268:21513–21518). For HIF-1α, the predominant protein species accumulating at later time points migrated to a higher position in the gel than protein present at earlier time points, suggesting that post-translational modification of HIF-1α may occur. For HIF-1β, the 94- and 93 kDa species were resolved from the 91 kDa form but not from each other and no shifts in migration were seen. The post-hypoxic decay of HIF-1 proteins was also remarkably rapid (FIG. 14D), indicating that, as with the RNAs, these proteins are unstable in posthypoxic cells. For both HIF-1α and ARNT, 31% of all amino acids are proline, glutamic acid, serine, or threonine (PEST) residues, which have been implicated in protein instability (Rogers et al. (1986) Science 234:364–368). In HIF-1α, two 20 amino acid sequences (499–518 and 581–600; FIG. 10) each contain 15 PEST residues. For HIF-1β (ARNT), redistribution between nuclear and cytoplasmic compartments also appeared to play a role in both the induction and decay of nuclear protein levels.

Together with our previous studies of HIF-1, the results presented here indicate that HIF-1 is a heterodimeric bHLH-PAS transcription factor consisting of a 120 kDa HIF-1α subunit complexed with a 91–94 kDa HIF-1β (ARNT) isoform. Thus, ARNT encodes a series of common subunits utilized by both HIF-1 and the dioxin receptor, analogous to the heterodimerization of E2A gene products with various bHLH proteins (Murre et al. (1989) Cell 58:537–544). Based upon these results and the similarity of HIF-1α and SIM within the bHLH-PAS domain, ARNT may also heterodimerize with SIM. In $Drosophila$, several SIM-regulated genes are characterized by enhancer elements that include 1–5 copies of the sequence 5'-(G/A)(T/A)ACGTG-3' (SEQ ID NO:29) (Wharton et al. (1994) Development 120:3563–3569). The observation that the HIF-1, dioxin receptor, and SIM binding sites share the sequence 5'-CGTG-3' supports the hypothesis that ARNT is capable of combinatorial association with HIF-1α, AHR, and SIM since this half-site is also recognized by the transcription factors with which ARNT shows greatest similarity in the bHLH domain.

EXAMPLE 9

Transcriptional Regulation of Genes Encoding Glycolytic Enzymes by HIF-1

The involvement of HIF-1 in transcriptional regulation of genes encoding glycolytic enzymes in hypoxic cells was investigated as follows.

RNA Analysis

Total RNA was isolated from Hep3B and HeLa cells (Chomczynski & Sacchi (1987) Anal. Biochem 162:156–159). RNA concentrations were determined by absorbance at 260 nm. Agarose gel electrophoresis, followed by ethidium bromide staining and visualization of 28 and 18 S rRNA under UV illumination, confirmed that aliquots from different preparations contained equal amounts of intact total RNA. Plasmids N-KS- and H-KS+, provided by P. Maire (Institut Cochin de Genetique Moleculaire, Paris), were linearized by digestion with HindIII. Antisense RNA was synthesized by T3 RNA polymerase in the presence of [$\alpha$-$^{32}$P]ATP. 10 ug of total cellular RNA was hybridized to H or N riboprobe ($3 \times 10^5$ cpm) for 3 h at 66° C. and digested with RNases A and $T_1$; protected fragments were analyzed by 8 M urea, 8% polyacrylamide gel electrophoresis (Semenza et al. (1990) Mol. Cell. Biol. 10:930–938). Human phosphoglyc-erate kinase 1 (PGK1) cDNA from plasmid pHPGK-7e (Michelson et al. (1985) Proc. Natl. Acad. Sci. USA 82:6965–6969), obtained from American Type Culture Collection, and rat PKM cDNA from plasmid pM2PK33 (Noguchi et al. (1986) J. Biol. Chem. 261:13807–13812), provided by T. Noguchi (Osaka University Medical SchooL Osaka. Japan), were used as random-labeled probes for blot hybridizations performed in QuikHyb (Stratagene) for 1 h at 68° C., followed by washing in 15 mM sodium chloride, 1.5 mM sodium citrate, 0.1% SDS at 50° C. Densitometric analysis of autoradiograms was performed with an LKM Ultroscan XL laser densitometer using computerized peak integration.

Electrophoretic Mobility Shift Assay (EMSA)

Crude nuclear extract preparations, conditions of probe preparation, binding reactions, and gel analysis were all previously described above. Double-stranded oligonucleotides were synthesized according to the sequences shown in Table 2 except that each oligonucleotide contained at its 5'-end the sequence 5'-GATC-3', which formed a single-stranded 5' overhang when complementary oligonucleotides were annealed. The sense strand sequence of the W18 and M18 oligonucleotides was as given above. HIF-1 was partially purified from 50 liters of $CoCl_2$-treated HeLa cells by crude nuclear extract preparation, DEAE-Sepharose chromatography, MonoQ fast protein liquid chromatography, and DNA affinity chromatography. Incubations with crude nuclear extracts and partially purified HIF-I contained 100 and 1 ng of denatured calf thymus DNA, respectively. Competition experiments were performed with 5 ng of unlabeled W18 or MI8 oligonucleotide.

Tissue Culture

Hep3B and HeLa cells were maintained in culture and treated with 1% $O_2$, $CoCl_2$, DFX, and cycloheximide (CHX) as described above.

Transient Expression Assay

The psvcat reporter plasmid (pCAT Promoter, Promega) contained SV40 early region promoter, bacterial chloramphenicol acetyltransferase (CAT) coding sequences, SV40 splice, and polyadenylation signals. Oligonucleotides were cloned into the BglII and BamHI sites located 5' and 3' to the transcription unit, respectively. Plasmids pNMHcat and pHcat (Concordet et al. (1991) Nucleic Acids Res. 19:4173–4180), containing human aldolase A gene sequences fused directly to CAT coding sequences, were provided by P. Maire. pSVβgal (Promega) contained bacterial lacZ coding sequences driven by the SV40 early region promoter and enhancer. Plasmids were purified by alkaline lysis and two rounds of cesium chloride density gradient centrifugation. Hep3B cells were transfected by electroporation with a Gene Pulser (Bio-Rad) at 260 V and 960 microfarads. Duplicate electroporations were pooled and split onto two 10 cm tissue culture dishes (Corning) containing 8 ml of media. Cells were allowed to recover for 24 h in a 5% $CO_2$ 95% air incubator at 37° C., the media was replaced, and one set of duplicate plates was removed to a modular incubator chamber, which was flushed with 1% $O_2$, 5% $CO_2$, balance $N_2$, sealed, and placed at 37° C. Cells were harvested 72 h after transfection, and extracts were prepared for CAT and β-galactosidase activity.

Results

The human aldolase A gene (hALDA) contains four noncoding exons, N1, N2, M, and H (Maire et al. (1987) J. Mol. Biol. 197:425–438). Transcription is initiated at exons N1 and H in most tissues other than muscle. Ribonuclease protection assays of RNA isolated from cells exposed to 20 or 1% $O_2$ for 16 h revealed 3.0- and 2.9-fold higher levels of ALDA RNA initiated from exon H in Hep3B and HeLa cells exposed to 1% $O_2$, whereas RNA initiated from exon N1 increased only 1.7- and 1.1-fold in hypoxic Hep3B and HeLa cells, respectively, suggesting a promoter-specific response to hypoxia.

We next compared the expression of ALDA and phosphoglycerate kinase 1 (PGK1) RNA in Hep3B cells exposed to 1% $O_2$ for 0–16 h. Maximal induction of both ALDA and PGK1 RNA showed delayed kinetics, suggesting a requirement for protein synthesis during induction, which was confirmed by the demonstration that treatment of Hep3B cells with 100 uM CHX decreased induction of ALDA and PGK1 RNA in hypoxic cells from 6.1- and 8.2-fold to 1.6- and 1.4-fold, respectively.

Treatment of Hep3B cells for 16 h with 75 uM $CoCl_2$ or 130 uM DFX induced both ALDA and PGK1 RNA with ALDA transcripts preferentially initiated from exon H. Analysis of the same RNA samples with a probe for PKM revealed that PKM RNA was also induced by exposure of Hep3B cells to 1% $O_2$, $CoCl_2$, or DFX. ALDA, PGK1, and PKM RNAs were also induced by treatment of HeLa cells with 1% $O_2$, $CoCl_2$, or DFX. PFKL RNA was not expressed at detectable levels in Hep3B or HeLa cells. These RNA analyses demonstrate that agents that induce EPO RNA and HIF-1 activity also induce ALDA, PGK1, and PKM RNA in both EPO-producing Hep3B and nonproducing HeLa cells, with a requirement for de novo protein synthesis, as previously demonstrated for induction of EPO RNA and HIF-1 activity (Semenza & Wang (1992) Mol. Cell. Biol. 12:5447–5454).

Nucleotide sequences of genes encoding glycolytic enzymes present in GenBank were searched for potential HIF-1 binding sites using the query sequence 5'-ACGTGC-3', which contains the 4 guanine residues that contact HIF-1 in the DNA major groove (Wang & Semenza (1993b) supra). Double-stranded oligonucleotides were synthesized corresponding to 5'-flanking sequences (5'-FS) of the human PGK1 (hPGKI), human enolase 1 (hENO1), and mouse LDHA (mLDHA) genes; 5'-untranslated sequences (5'-UT) of hPGK1; and intervening sequences (IVS) of the hALDA and mPFKL genes. These oligonucleotides contained, as potential HIF-1 sites, 5'-TACGTGCT-3' (SEQ ID NO:30), 5'-GACGTGCG-3' (SEQ ID NO:31) (which was also found in hEPO 5'-FS), and 5'-CACGTGCG-3' (SEQ ID NO:32). The first sequence is identical to the previously identified HIF-1 binding site in the EPO enhancer (Semenza & Wang (1992) supra), whereas the latter two sequences differ at the first and last nucleotides. The ability of these oligonucleotides to bind HIF-1 was tested by EMSA.

When incubated with nuclear extract prepared from Hep3B cells exposed to 1% $O_2$ for 4 h, each probe generated a DNA protein complex of similar mobility and intensity to the HIF-1 complex formed with probe W18, corresponding to nucleotides 1–18 of the hEPO 3'-FS. In contrast, none of these probes detected an HIF-1 complex in nuclear extracts from cells maintained at 20% $O_2$, although the EMSA patterns were otherwise similar to those obtained with nuclear extracts from hypoxic cells. The DNA-protein complex migrating below the HIF-1 complex was less intense when hypoxic (compared with non-hypoxic) nuclear extracts were assayed. We have previously shown that this complex contains a constitutively expressed factor that recognizes the same DNA sequence as HIF-1 (Wang & Semenza (1993b) supra). The decreased binding of the constitutive factor may thus result from competition for binding with HIF-1 in hypoxic extracts.

EMSA was also performed with a preparation of HIF-1 from $CoCl_2$-treated HeLa cells that was purified approximately 600-fold by DEAE-cellulose, MonoQ, and DNA affinity chromatography. Each probe bound HIF-1 in a manner that was qualitatively and quantitatively similar to the complex formed with W18. The binding of HIF-1 to these probes was sequence-specific as it could be competed by an excess of unlabeled W18 but not by mutant oligonucleotide M18, containing a 3-nucleotide substitution previously shown to eliminate HIF-1 binding and hypoxia-inducible enhancer function. Similar results were obtained when competition experiments involving W18 and M18 were performed with crude nuclear extract from hypoxic Hep3B cells. These results identify novel HIF-1 binding sites in genes encoding ALDA, ENO1, PFKL, and PGKl as well as in the hEPO 5'-FS. The 8 oligonucleotides that have been shown to specifically bind HIF-1 (Table 2) contain 3 different binding site sequences that are represented by the consensus 5'-(C/G/T)ACGTGC(G/T)-3' (SEQ ID NO:33). Given the biased method of ascertainment, it is possible that HIF-1 may recognize other sequences not represented by this consensus. In addition to the 6 HIF-1 sites from glycolytic genes, the sequence 5'-CACGTGCT-3' (SEQ ID NO:34) was also present in the hENO1 5'-FS at −786 to −793 (Gialongo et al. (1990) Eur. J. Biochem. 190:567–573) but was not tested for HIF-1 binding. Thus, a total of 7 probable HIF-1 sites were identified in 20.7 kb of nucleotide sequence reported to GenBank for these 5 glycolytic genes. In contrast, no sequences matching the consensus HIF-1 site were identified on either DNA strand within a total of 43.5 kb, comprising the nucleotide sequences of 5 randomly chosen genes, AFP, BUP4, CREB, DHFR, and EPOR (Gibbs et al. (1987) Biochemistry 26;1332–1343; Kurihara et al. (1993) Biochem. Biophys. Res. Commun. 192:1049–1056; Meyer et al. (1993) Endocrinology 132:770–780; Mitchell et al. (1986) Mol. Cell. Biol. 6:425–440; Noguchi et al. (1991) Blood 78:2548–2556).

To determine whether these HIF-1 binding sites were of functional importance, transient expression essays were performed using the reporter genes described above. Reporter plasmids were cotransfected into Hep3B cells with pSVβgal, which was included as a control for variation in transfection efficiency. Transfected cells were split among duplicate plates that were cultured in 1 or 20% $O_2$ for 48 h, CAT and β-galactosidase protein synthesized following transcription of reporter and control plasmids, respectively, were quantitated from cellular extracts. The basal reporter psvcat, in which transcription of CAT coding sequences was driven by the SV40 early region promoter, generated similar CAT/β-galactosidase values in cells cultured at 1 and 20% $O_2$. When one (psvcatEPO1) or two (psvcatEPO2) copies of the 33-base pair hEPO 3'-FS enhancer were cloned 3' to the transcription unit, CAT/β-galactosidase expression was induced 4.9- and 17-fold, respectively, in cells cultured at 1% $O_2$, consistent with previously reported results (Semenza & Wang (1992) supra).

Figure 15A:
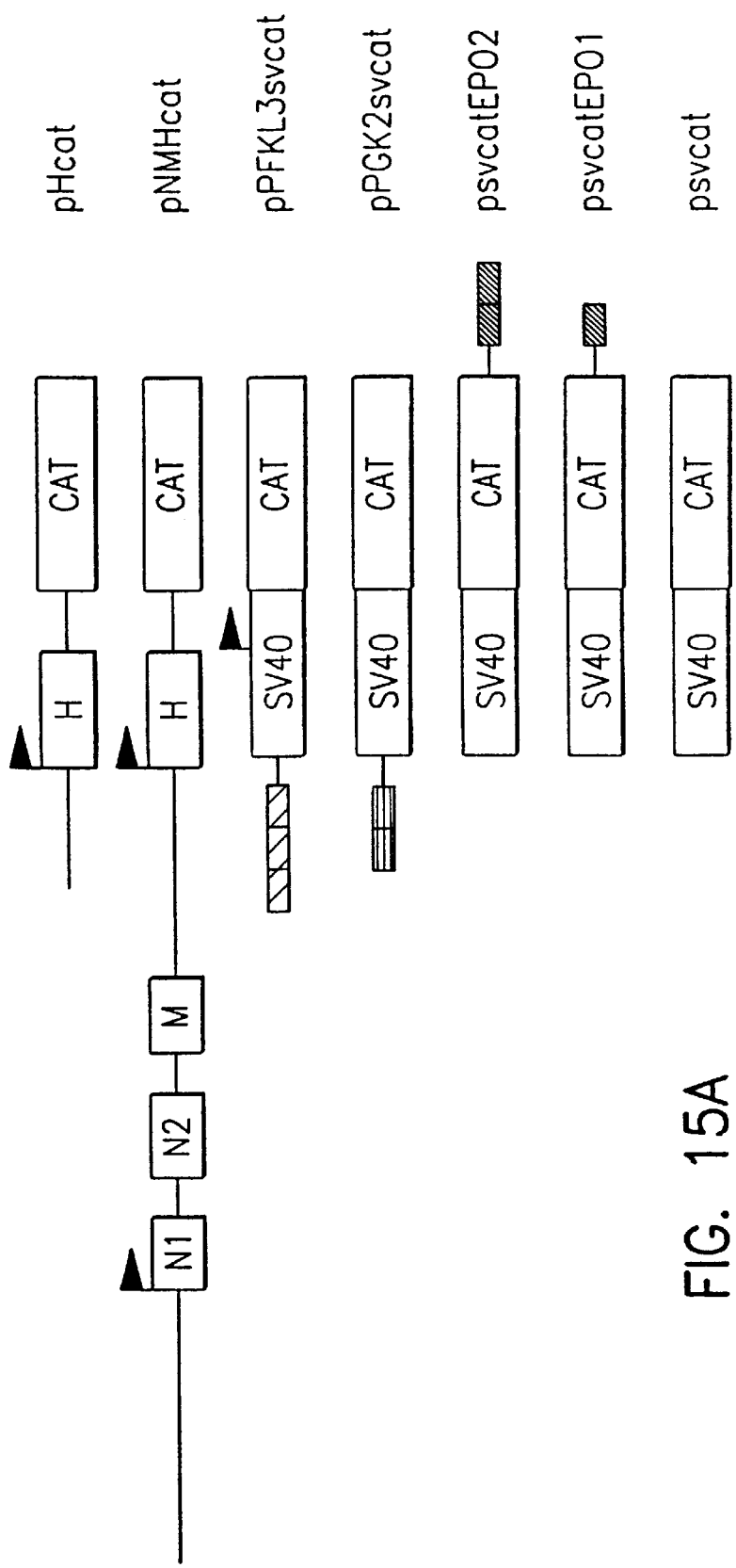
FIG. 15A is an diagram of the structure of reporter gene constructs used for functional analysis of HIF-1 binding sites in human aldolase A (hALDA), human phosphoglycerate kinase 1 (hPGK1), and mouse phosphofructokinase L (mPFKL) genes. Arrow, transcription initiation site; box, hEPO 3'-FS (cross-hatched), hPGK1 5'-FS (stippled), or mPFKL IVS-1 (striped) oligonucleotide (sequences are as shown in Table 3). DNA fragments from the 5'-end of the hALDA gene in pNMHcat and pHcat are 3.5 and 0.76 kb, respectively, and are colinear at the 3'-end where they are directly fused to CAT coding sequences.
Figure 15B:
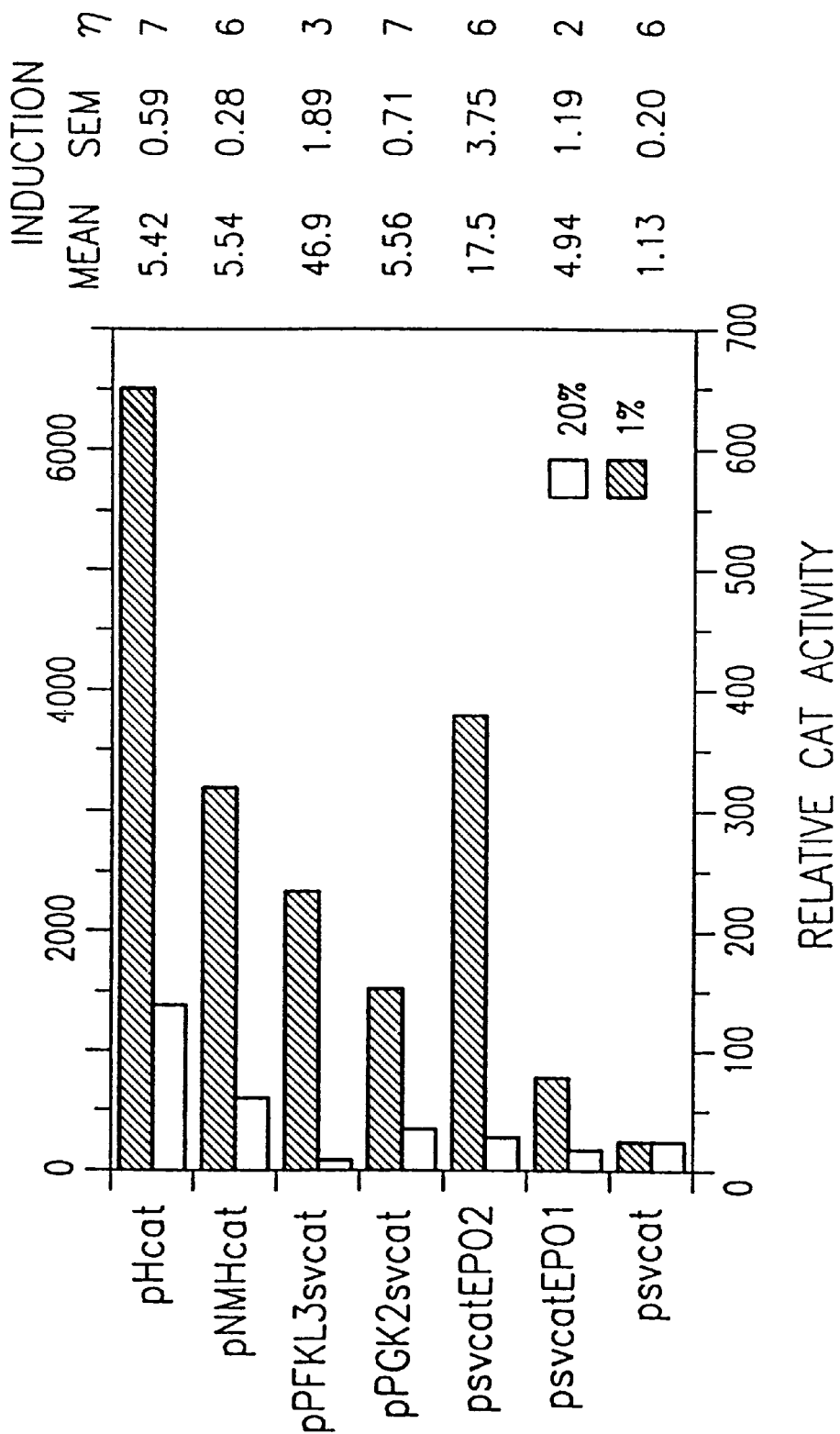
FIG. 15B is a bar graph showing CAT/β-galactosidase expression (relative CAT activity) in transfected cells exposed to 20% O₂ (open bar) or 1% O₂ (closed bar). Data are plotted using lower scale for all results except those for pHcat, which are plotted according to the upper scale. Induction, representing the relative CAT activity at 1% O₂/20% O₂, was calculated for each experiment; mean and standard error of mean (SEM) were determined for results from n independent experiments.

HIF-1 binding site sequences from glycolytic genes were analyzed in the same assay. The mPFKL IVS-1 and hPFK1 5'-FS oligonucleotides were chosen, as they represented sequences identical to or divergent from the HIF-1 site in the hEPO 3'-FS and were located 3' or 5' to the transcription initiation site, respectively. Two copies of the 24-base pair hPGK1 5'-FS oligonucleotide were cloned 5' to the psvcat transcription unit (FIG. 15A), analogous to its location in hPGK1. Expression of pPGK2svcat was induced 5.6-fold in hypoxic cells (FIG. 15B). Three copies of the 26-base pair mPFK1 IVS-1 oligonucleotide were also cloned 5' to the psvcat transcription unit, and pPFKL3svcat mediated a 47-fold induction in hypoxic cells (FIG. 15B).

We also performed experiments with hALDA gene sequences to analyze native promoter function and to correlate sequence requirements for induction in the transfection assay with endogenous RNA expression data. The plasmid pNMHcat (Concordet et al. (1991) supra), in which 3.5 kb from the 5'-end of hALDA (Maire et al. (1987) supra) was fused to CAT coding sequences (FIG. 15A), mediated a 5.5-fold induction in hypoxic cells (FIG. 15B). The plasmid pHcat contained 0.76 kb of hALDA sequences that are colinear with the 3'-end of pNMHcat, starting within IVS-4 and extending 5' to exon H (FIG. 15A). Deletion of exons N1, N2, and M and their flanking sequences resulted in 20-fold increased levels of CAT expression but had no significant effect on relative expression in 1% $O_2$, as pHcat was induced 5.4-fold in hypoxic Hep3B cells (FIG. 15B). These results are consistent with the observation of (i) specific induction of hALDA transcripts initiated from exon H and (ii) the presence of a HIF-1 binding site at the 5' end of IVS-4 contained within both pNMHcat and pHcat. Thus, sequences containing HIF-1 sites from the mPFKL, hPGK1, and hALDA genes mediated hypoxia-inducible transcription in conjunction with either a native or heterologous promoter.

EXAMPLE 10

Construction of a Dominant-negative Variant of HIF-1α

A HIF-1α variant was constructed to investigate functional inactivation of HIF-1.

The starting construct was the HIF-1α cDNA 3.2–3 cloned into the plasmid pBluescript SK-. This plasmid was digested with the restriction endonucleases NcoI and BglII to delete sequences encoding amino acids 2–28. A double-stranded oligonucleotide was inserted that contained NcoI and BglII ends to allow recirculation of the plasmid in the presence of T4 DNA ligase. The resulting construct encodes amino acids 1–3, followed by three amino acids not present in the corresponding position in wild-type HIF-1α (isoleucine, alanine, and glycine), followed by amino acids 28–826 of HIF-1α. This construction (pBluescript/HIF-1α3.2T7ΔNB) allows the in vitro transcription (using T7 RNA polymerase) and translation of the variant form of HIF-1α (HIF-1αΔNB) (SEQ ID NO:34).

To create a dominant negative form of HIF-1α for expression in mammalian tissue culture cells, a Kpn I-Not I fragment encoding the variant CDNA was excised from the pBluescript vector and cloned into the mammalian expression vector pCEP4. The plasmid was digested with AflII and BamHI, treated with Klenow form of DNA polymerase to generate blunt ends, and recircularized with T4 DNA ligase. The resulting plasmid (pCEP4/HIF-1αΔNBΔAB) (SEQ ID NO:3) encodes amino acids 1–3, followed by three amino acids not present at the corresponding position in wild-type HIF-1α (isoleucine, alanine, and glycine), followed by amino acids 28–391 of HIF-1α, followed by three amino acids not present at the corresponding position in wild-type HIF-1α (isoleucine, glutamine, and threonine). Amino acids 392–826 were deleted to increase the stability of the variant protein (HIF-1αΔNBΔAB) expressed in cells (FIG. 16).

Results

Hep3B cells were transiently transfected with 25 ug of the reporter gene psvcatEPO2 which contains two copies of the 33-bp enhancer sequence from the human erythropoietin gene as described above. This plasmid expressed a 9-fold higher level of CAT protein when cells were cultured at 1% $O_2$ relative to 20% $O_2$. When the cells were transfected with psvcatEPO2 and pCEP4/HIF-1αΔNBΔAB, there was dose-dependent inhibition of CAT expression at 1% $O_2$. Table 3 shows the relative induction (expression at 1% $O_2$ divided by expression at 20% $O_2$) as a function of the amount of pCEP4/HIF-1αΔNBΔAB (ug) transfected into the cells. Results are the mean of three experiments.

Expression of variant HIF-1α interfered with the activation of reporter gene expression by endogenous HIF-1 produced by hypoxic cells. The residual activation seen with 40 ug variant transfection may represent cells which took up psvcatEPO2 but not pCEP4/HIF-1αΔNBΔAB. The results show that the dominant-negative variant can interfere with HIF-1 function in vivo.

The variant protein was used in a electrophoretic mobility shift assay of binding to a double-stranded oligonucleotide probe containing the HIF-1 binding site from the EPO enhancer. pBluescript/HIF-1α3.2T7ΔNB was used as a template for in vitro transcription and translation. As increasing amounts of pBluescript/HIF-1α3.2T7ΔNB were added to reactions containing a constant amount of templates for wild-type HIF-1α and HIF-1β, there was a dose-dependent inhibition of DNA-binding such that when pBluescript/HIF-1α3.2T7ΔNB was present in a 16-fold excess over the wild-type template pBluescript/HIF-1α3.2T7, HIF-1 DNA-binding was eliminated.

These in vitro and in vivo experiments demonstrate that deletion of the basic domain of HIF-1α results in a protein that can block HIF-1 activity by inhibiting DNA binding.

TABLE 1

BIOCHEMICAL PURIFICATION OF HIF-1

| Purification Step | Volume (ml) | Protein (mg) | HIF-1 Activity | Specific Activity | Yield (%) | Purification |
|---|---|---|---|---|---|---|
| HeLa nuclear Extract | 435 | 3,040 | 608,000 | 0.2 U/ug | 100 | 1 |
| DEAE-Sepharose | 240 | 550 | 440,000 | 0.8 U/mg | 72 | 4 |
| W18 DNA affinity 1 | 25 | 2.5 | 400,000 | 160 | 66 | 800 |
| M18 DNA column | 40 | 1.4 | 226,000 | 190 | 44 | 950 |
| W18 DNA affinity 2 | 9 | 0.06 | 135,000 | 2,250 | 22 | 11,250 |

TABLE 2

OLIGONUCLEOTIDE SEQUENCES FROM EPO AND GLYCOLYTIC ENZYME GENES.

| SEQUENCE | LOCATION | COORDINATES |
|---|---|---|
| gccc TACGTGCT gtctcacacagcctgtctga | hEPQ 3'-FS | +3065/+3097 |
| ccgggtagctggcg TACGTGCT gcag | mPFKL IVS-1 | +336/+361 |
| ggggctgctgca GACGTGCG tgtg | hEPO 5'-FS | -155/-178 |
| gtga GACGTGCG gcttccgtttg | hPGK1 5'-FS | -172/-194 |
| ctgcc GACGTGCG ctccggag | hPGK1 5'-UT | +31 /+11 |
| gtgggagcccagcg GACGTGCG ggaa | mLDHA 5'-FS | -75/-50 |
| ggc CADGTGCG ccgcctgcgcctgcg | hENO1 5'-FS | -585/-610 |
| ctt CACGTGCG gggaccagggaccgt | hALDA IVS-4 | +125/+150 |

TABLE 3

RELATIVE INDUCTION OF REPORTER GENE IN THE PRESENCE OF HIF-1α VARIANT

| ug Variant | Relative Hypoxic Induction |
|---|---|
| 0 | 9.09 |
| 5 | 6.06 |
| 10 | 4.10 |
| 20 | 2.81 |
| 40 | 2.31 |

What is claimed is:

1. A purified antibody that binds to HIF-1 or to the HIF-1α polypeptide or immunoreactive fragments thereof.

2. The antibody of claim 1, wherein the antibody is polyclonal.

3. The antibody of claim 1, wherein the antibody is monoclonal.

* * * * *

SEQUENCE LISTING (1) GENERAL INFORMATION:

(iii) NUMBER OF SEQUENCES: 64

(2) INFORMATION FOR SEQ ID NO:1:

(i) SEQUENCE CHARACTERISTICS:
      (A) LENGTH: 3736 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO:1:

```
GTGAAGACAT CGCGGGGACC GATTCACC ATG GAG GGC GCC GGC GGC GCG AAC          52
                               Met Glu Gly Ala Gly Gly Ala Asn
                                1               5

GAC AAG AAA AAG ATA AGT TCT GAA CGT CGA AAA GAA AAG TCT CGA GAT         100
Asp Lys Lys Lys Ile Ser Ser Glu Arg Arg Lys Glu Lys Ser Arg Asp
     10              15                  20

GCA GCC AGA TCT CGG CGA AGT AAA GAA TCT GAA GTT TTT TAT GAG CTT        148
Ala Ala Arg Ser Arg Arg Ser Lys Glu Ser Glu Val Phe Tyr Glu Leu
 25              30                  35                  40

GCT CAT CAG TTG CCA CTT CCA CAT AAT GTG AGT TCG CAT CTT GAT AAG        196
Ala His Gln Leu Pro Leu Pro His Asn Val Ser Ser His Leu Asp Lys
```

```
                    45                    50                    55
GCC TCT GTG ATG AGG CTT ACC ATC AGC TAT TTG CGT GTG AGG AAA CTT    244
Ala Ser Val Met Arg Leu Thr Ile Ser Tyr Leu Arg Val Arg Lys Leu
             60                  65                  70

CTG GAT GCT GGT GAT TTG GAT ATT GAA GAT GAC ATG AAA GCA CAG ATG    292
Leu Asp Ala Gly Asp Leu Asp Ile Glu Asp Asp Met Lys Ala Gln Met
         75                  80                  85

AAT TGC TTT TAT TTG AAA GCC TTG GAT GGT TTT GTT ATG GTT CTC ACA    340
Asn Cys Phe Tyr Leu Lys Ala Leu Asp Gly Phe Val Met Val Leu Thr
     90                  95                 100

GAT GAT GGT GAC ATG ATT TAC ATT TCT GAT AAT GTG AAC AAA TAC ATG    388
Asp Asp Gly Asp Met Ile Tyr Ile Ser Asp Asn Val Asn Lys Tyr Met
105                 110                 115                 120

GGA TTA ACT CAG TTT GAA CTA ACT GGA CAC AGT GTG TTT GAT TTT ACT    436
Gly Leu Thr Gln Phe Glu Leu Thr Gly His Ser Val Phe Asp Phe Thr
                125                 130                 135

CAT CCA TGT GAC CAT GAG GAA ATG AGA GAA ATG CTT ACA CAC AGA AAT    484
His Pro Cys Asp His Glu Glu Met Arg Glu Met Leu Thr His Arg Asn
            140                 145                 150

GGC CTT GTG AAA AAG GGT AAA GAA CAA AAC ACA CAG CGA AGC TTT TTT    532
Gly Leu Val Lys Lys Gly Lys Glu Gln Asn Thr Gln Arg Ser Phe Phe
        155                 160                 165

CTC AGA ATG AAG TGT ACC CTA ACT AGC CGA GGA AGA ACT ATG AAC ATA    580
Leu Arg Met Lys Cys Thr Leu Thr Ser Arg Gly Arg Thr Met Asn Ile
    170                 175                 180

AAG TCT GCA ACA TGG AAG GTA TTG CAC TGC ACA GGC CAC ATT CAC GTA    628
Lys Ser Ala Thr Trp Lys Val Leu His Cys Thr Gly His Ile His Val
185                 190                 195                 200

TAT GAT ACC AAC AGT AAC CAA CCT CAG TGT GGG TAT AAG AAA CCA CCT    676
Tyr Asp Thr Asn Ser Asn Gln Pro Gln Cys Gly Tyr Lys Lys Pro Pro
                205                 210                 215

ATG ACC TGC TTG GTG CTG ATT TGT GAA CCC ATT CCT CAC CCA TCA AAT    724
Met Thr Cys Leu Val Leu Ile Cys Glu Pro Ile Pro His Pro Ser Asn
            220                 225                 230

ATT GAA ATT CCT TTA GAT AGC AAG ACT TTC CTC AGT CGA CAC AGC CTG    772
Ile Glu Ile Pro Leu Asp Ser Lys Thr Phe Leu Ser Arg His Ser Leu
        235                 240                 245

GAT ATG AAA TTT TCT TAT TGT GAT GAA AGA ATT ACC GAA TTG ATG GGA    820
Asp Met Lys Phe Ser Tyr Cys Asp Glu Arg Ile Thr Glu Leu Met Gly
    250                 255                 260

TAT GAG CCA GAA GAA CTT TTA GGC CGC TCA ATT TAT GAA TAT TAT CAT    868
Tyr Glu Pro Glu Glu Leu Leu Gly Arg Ser Ile Tyr Glu Tyr Tyr His
265                 270                 275                 280

GCT TTG GAC TCT GAT CAT CTG ACC AAA ACT CAT CAT GAT ATG TTT ACT    916
Ala Leu Asp Ser Asp His Leu Thr Lys Thr His His Asp Met Phe Thr
                285                 290                 295

AAA GGA CAA GTC ACC ACA GGA CAG TAC AGG ATG CTT GCC AAA AGA GGT    964
Lys Gly Gln Val Thr Thr Gly Gln Tyr Arg Met Leu Ala Lys Arg Gly
            300                 305                 310

GGA TAT GTC TGG GTT GAA ACT CAA GCA ACT GTC ATA TAT AAC ACC AAG   1012
Gly Tyr Val Trp Val Glu Thr Gln Ala Thr Val Ile Tyr Asn Thr Lys
        315                 320                 325

AAT TCT CAA CCA CAG TGC ATT GTA TGT GTG AAT TAC GTT GTG AGT GGT   1060
Asn Ser Gln Pro Gln Cys Ile Val Cys Val Asn Tyr Val Val Ser Gly
    330                 335                 340

ATT ATT CAG CAC GAC TTG ATT TTC TCC CTT CAA CAA ACA GAA TGT GTC   1108
Ile Ile Gln His Asp Leu Ile Phe Ser Leu Gln Gln Thr Glu Cys Val
345                 350                 355                 360

CTT AAA CCG GTT GAA TCT TCA GAT ATG AAA ATG ACT CAG CTA TTC ACC   1156
```

```
                                                          -continued

Leu Lys Pro Val Glu Ser Ser Asp Met Lys Met Thr Gln Leu Phe Thr
            365                 370                 375

AAA GTT GAA TCA GAA GAT ACA AGT AGC CTC TTT GAC AAA CTT AAG AAG         1204
Lys Val Glu Ser Glu Asp Thr Ser Ser Leu Phe Asp Lys Leu Lys Lys
            380                 385                 390

GAA CCT GAT GCT TTA ACT TTG CTG GCC CCA GCC GCT GGA GAC ACA ATC         1252
Glu Pro Asp Ala Leu Thr Leu Leu Ala Pro Ala Ala Gly Asp Thr Ile
            395                 400                 405

ATA TCT TTA GAT TTT GGC AGC AAC GAC ACA GAA ACT GAT GAC CAG CAA         1300
Ile Ser Leu Asp Phe Gly Ser Asn Asp Thr Glu Thr Asp Asp Gln Gln
            410                 415                 420

CTT GAG GAA GTA CCA TTA TAT AAT GAT GTA ATG CTC CCC TCA CCC AAC         1348
Leu Glu Glu Val Pro Leu Tyr Asn Asp Val Met Leu Pro Ser Pro Asn
425                 430                 435                 440

GAA AAA TTA CAG AAT ATA AAT TTG GCA ATG TCT CCA TTA CCC ACC GCT         1396
Glu Lys Leu Gln Asn Ile Asn Leu Ala Met Ser Pro Leu Pro Thr Ala
                445                 450                 455

GAA ACG CCA AAG CCA CTT CGA AGT AGT GCT GAC CCT GCA CTC AAT CAA         1444
Glu Thr Pro Lys Pro Leu Arg Ser Ser Ala Asp Pro Ala Leu Asn Gln
            460                 465                 470

GAA GTT GCA TTA AAA TTA GAA CCA AAT CCA GAG TCA CTG GAA CTT TCT         1492
Glu Val Ala Leu Lys Leu Glu Pro Asn Pro Glu Ser Leu Glu Leu Ser
            475                 480                 485

TTT ACC ATG CCC CAG ATT CAG GAT CAG ACA CCT AGT CCT TCC GAT GGA         1540
Phe Thr Met Pro Gln Ile Gln Asp Gln Thr Pro Ser Pro Ser Asp Gly
            490                 495                 500

AGC ACT AGA CAA AGT TCA CCT GAG CCT AAT AGT CCC AGT GAA TAT TGT         1588
Ser Thr Arg Gln Ser Ser Pro Glu Pro Asn Ser Pro Ser Glu Tyr Cys
505                 510                 515                 520

TTT TAT GTG GAT AGT GAT ATG GTC AAT GAA TTC AAG TTG GAA TTG GTA         1636
Phe Tyr Val Asp Ser Asp Met Val Asn Glu Phe Lys Leu Glu Leu Val
                525                 530                 535

GAA AAA CTT TTT GCT GAA GAC ACA GAA GCA AAG AAC CCA TTT TCT ACT         1684
Glu Lys Leu Phe Ala Glu Asp Thr Glu Ala Lys Asn Pro Phe Ser Thr
            540                 545                 550

CAG GAC ACA GAT TTA GAC TTG GAG ATG TTA GCT CCC TAT ATC CCA ATG         1732
Gln Asp Thr Asp Leu Asp Leu Glu Met Leu Ala Pro Tyr Ile Pro Met
            555                 560                 565

GAT GAT GAC TTC CAG TTA CGT TCC TTC GAT CAG TTG TCA CCA TTA GAA         1780
Asp Asp Asp Phe Gln Leu Arg Ser Phe Asp Gln Leu Ser Pro Leu Glu
            570                 575                 580

AGC AGT TCC GCA AGC CCT GAA AGC GCA AGT CCT CAA AGC ACA GTT ACA         1828
Ser Ser Ser Ala Ser Pro Glu Ser Ala Ser Pro Gln Ser Thr Val Thr
585                 590                 595                 600

GTA TTC CAG CAG ACT CAA ATA CAA GAA CCT ACT GCT AAT GCC ACC ACT         1876
Val Phe Gln Gln Thr Gln Ile Gln Glu Pro Thr Ala Asn Ala Thr Thr
                605                 610                 615

ACC ACT GCC ACC ACT GAT GAA TTA AAA ACA GTG ACA AAA GAC CGT ATG         1924
Thr Thr Ala Thr Thr Asp Glu Leu Lys Thr Val Thr Lys Asp Arg Met
            620                 625                 630

GAA GAC ATT AAA ATA TTG ATT GCA TCT CCA TCT CCT ACC CAC ATA CAT         1972
Glu Asp Ile Lys Ile Leu Ile Ala Ser Pro Ser Pro Thr His Ile His
            635                 640                 645

AAA GAA ACT ACT AGT GCC ACA TCA TCA CCA TAT AGA GAT ACT CAA AGT         2020
Lys Glu Thr Thr Ser Ala Thr Ser Ser Pro Tyr Arg Asp Thr Gln Ser
650                 655                 660

CGG ACA GCC TCA CCA AAC AGA GCA GGA AAA GGA GTC ATA GAA CAG ACA         2068
Arg Thr Ala Ser Pro Asn Arg Ala Gly Lys Gly Val Ile Glu Gln Thr
665                 670                 675                 680
```

```
GAA AAA TCT CAT CCA AGA AGC CCT AAC GTG TTA TCT GTC GCT TTG AGT        2116
Glu Lys Ser His Pro Arg Ser Pro Asn Val Leu Ser Val Ala Leu Ser
            685                 690                 695

CAA AGA ACT ACA GTT CCT GAG GAA GAA CTA AAT CCA AAG ATA CTA GCT        2164
Gln Arg Thr Thr Val Pro Glu Glu Glu Leu Asn Pro Lys Ile Leu Ala
                700                 705                 710

TTG CAG AAT GCT CAG AGA AAG CGA AAA ATG GAA CAT GAT GGT TCA CTT        2212
Leu Gln Asn Ala Gln Arg Lys Arg Lys Met Glu His Asp Gly Ser Leu
            715                 720                 725

TTT CAA GCA GTA GGA ATT GGA ACA TTA TTA CAG CAG CCA GAC GAT CAT        2260
Phe Gln Ala Val Gly Ile Gly Thr Leu Leu Gln Gln Pro Asp Asp His
        730                 735                 740

GCA GCT ACT ACA TCA CTT TCT TGG AAA CGT GTA AAA GGA TGC AAA TCT        2308
Ala Ala Thr Thr Ser Leu Ser Trp Lys Arg Val Lys Gly Cys Lys Ser
745                 750                 755                 760

AGT GAA CAG AAT GGA ATG GAG CAA AAG ACA ATT ATT TTA ATA CCC TCT        2356
Ser Glu Gln Asn Gly Met Glu Gln Lys Thr Ile Ile Leu Ile Pro Ser
                765                 770                 775

GAT TTA GCA TGT AGA CTG CTG GGG CAA TCA ATG GAT GAA AGT GGA TTA        2404
Asp Leu Ala Cys Arg Leu Leu Gly Gln Ser Met Asp Glu Ser Gly Leu
            780                 785                 790

CCA CAG CTG ACC AGT TAT GAT TGT GAA GTT AAT GCT CCT ATA CAA GGC        2452
Pro Gln Leu Thr Ser Tyr Asp Cys Glu Val Asn Ala Pro Ile Gln Gly
        795                 800                 805

AGC AGA AAC CTA CTG CAG GGT GAA GAA TTA CTC AGA GCT TTG GAT CAA        2500
Ser Arg Asn Leu Leu Gln Gly Glu Glu Leu Leu Arg Ala Leu Asp Gln
            810                 815                 820

GTT AAC T GAGCTTTTTC TTAATTTCAT TCCTTTTTTT GGACACTGGT GGCTCACTAC      2557
Val Asn
825

CTAAAGCAGT CTATTTATAT TTTCTACATC TAATTTTAGA AGCCTGGCTA CAATACTGCA     2617

CAAACTTGGT TAGTTCAATT TTTGATCCCC TTTCTACTTA ATTTACATTA ATGCTCTTTT     2677

TTAGTATGTT CTTTAATGCT GGATCACAGA CAGCTCATTT TCTCAGTTTT TTGGTATTTA     2737

AACCATTGCA TTGCAGTAGC ATCATTAATT AAAAAATGCA CCTTTTTATT TATTTATTTT     2797

TGGCTAGGGA GTTATCCCT TTTTCGAATT ATTTTTAAGA AGATGCCAAT ATAATTTTTG      2857

TAAGAAGGCA GTAACCTTTC ATCATGATCA TAGGCAGTTG AAAAATTTTT ACACCTTTTT     2917

TTTCACAAAT TTTACATAAA TAATAATGCT TTGCCAGCAG TACGTGGTAG CCACAATTGC     2977

ACAATATATT TTCTTAAAAA ATACCAGCAG TTACTCATGG AATATATTCT GCGTTTATAA     3037

AACTAGTTTT TAAGAAGAAA TTTTTTTTGG CCTATGAAAT TGTTAAACAA CTGGAACATG     3097

ACATTGTTAA TCATATAATA ATGATTCTTA AATGCTGTAT GGTTTATTAT TTAAATGGGT     3157

AAAGCCATTT ACATAATATA GAAAGATATG CATATATCTA GAAGGTATGT GGCATTTATT     3217

TGGATAAAAT TCTCAATTCA GAGAAATCAA ATCTGATGTT TCTATAGTCA CTTTGCCAGC     3277

TCAAAAGAAA ACAATACCCT ATGTAGTTGT GGAAGTTTAT GCTAATATTG TGTAACTGAT     3337

ATTAAACCTA AATGTTCTGC CTACCCTGTT GGTATAAAGA TATTTTGAGC AGACTGTAAA     3397

CAAGAAAAAA AAAAAATCAT GCATTCTTAG CAAAATTGCC TAGTATGTTA ATTTGCTCAA     3457

AATACAATGT TTGATTTTAT GCACTTTGTC GCTATTAACA TCCTTTTTTT CATGTAGATT     3517

TCAATAATTG AGTAATTTTA GAAGCATTAT TTTAGGAATA TATAGTTGTC AAAAACAGTA    3577

AATATCTTGT TTTTTCTATG TACATTGTAC AAATTTTTCA TTCCTTTTGC TCTTTGTGGT    3637

TGGATCTAAC ACTAACTGTA TTGTTTTGTT ACATCAAATA AACATCTTCT GTGGAAAAAA    3697

AAAAAAAAAA AAAAAAAAAA AAAAAAAAAA AAAAAAAA                             3736
```

(2) INFORMATION FOR SEQ ID NO:2:

(i) SEQUENCE CHARACTERISTICS:
        (A) LENGTH: 826 amino acids
        (B) TYPE: amino acid
        (D) TOPOLOGY: linear (ii) MOLECULE TYPE: protein (xi) SEQUENCE DESCRIPTION: SEQ ID NO:2:

```
Met Glu Gly Ala Gly Gly Ala Asn Asp Lys Lys Ile Ser Ser Glu
 1               5                  10                  15

Arg Arg Lys Glu Lys Ser Arg Asp Ala Ala Arg Ser Arg Arg Ser Lys
             20                  25                  30

Glu Ser Glu Val Phe Tyr Glu Leu Ala His Gln Leu Pro Leu Pro His
         35                  40                  45

Asn Val Ser Ser His Leu Asp Lys Ala Ser Val Met Arg Leu Thr Ile
     50                  55                  60

Ser Tyr Leu Arg Val Arg Lys Leu Leu Asp Ala Gly Asp Leu Asp Ile
 65                  70                  75                  80

Glu Asp Asp Met Lys Ala Gln Met Asn Cys Phe Tyr Leu Lys Ala Leu
                 85                  90                  95

Asp Gly Phe Val Met Val Leu Thr Asp Asp Gly Asp Met Ile Tyr Ile
                100                 105                 110

Ser Asp Asn Val Asn Lys Tyr Met Gly Leu Thr Gln Phe Glu Leu Thr
             115                 120                 125

Gly His Ser Val Phe Asp Phe Thr His Pro Cys Asp His Glu Glu Met
         130                 135                 140

Arg Glu Met Leu Thr His Arg Asn Gly Leu Val Lys Lys Gly Lys Glu
145                 150                 155                 160

Gln Asn Thr Gln Arg Ser Phe Phe Leu Arg Met Lys Cys Thr Leu Thr
                 165                 170                 175

Ser Arg Gly Arg Thr Met Asn Ile Lys Ser Ala Thr Trp Lys Val Leu
                 180                 185                 190

His Cys Thr Gly His Ile His Val Tyr Asp Thr Asn Ser Asn Gln Pro
             195                 200                 205

Gln Cys Gly Tyr Lys Lys Pro Pro Met Thr Cys Leu Val Leu Ile Cys
         210                 215                 220

Glu Pro Ile Pro His Pro Ser Asn Ile Glu Ile Pro Leu Asp Ser Lys
225                 230                 235                 240

Thr Phe Leu Ser Arg His Ser Leu Asp Met Lys Phe Ser Tyr Cys Asp
                 245                 250                 255

Glu Arg Ile Thr Glu Leu Met Gly Tyr Glu Pro Glu Glu Leu Leu Gly
                 260                 265                 270

Arg Ser Ile Tyr Glu Tyr Tyr His Ala Leu Asp Ser Asp His Leu Thr
             275                 280                 285

Lys Thr His His Asp Met Phe Thr Lys Gly Gln Val Thr Thr Gly Gln
         290                 295                 300

Tyr Arg Met Leu Ala Lys Arg Gly Gly Tyr Val Trp Val Glu Thr Gln
305                 310                 315                 320

Ala Thr Val Ile Tyr Asn Thr Lys Asn Ser Gln Pro Gln Cys Ile Val
                 325                 330                 335

Cys Val Asn Tyr Val Val Ser Gly Ile Ile Gln His Asp Leu Ile Phe
             340                 345                 350
```

```
Ser Leu Gln Gln Thr Glu Cys Val Leu Lys Pro Val Glu Ser Ser Asp
        355                 360                 365
Met Lys Met Thr Gln Leu Phe Thr Lys Val Glu Ser Glu Asp Thr Ser
    370                 375                 380
Ser Leu Phe Asp Lys Leu Lys Lys Glu Pro Asp Ala Leu Thr Leu Leu
385                 390                 395                 400
Ala Pro Ala Ala Gly Asp Thr Ile Ile Ser Leu Asp Phe Gly Ser Asn
                405                 410                 415
Asp Thr Glu Thr Asp Asp Gln Gln Leu Glu Glu Val Pro Leu Tyr Asn
            420                 425                 430
Asp Val Met Leu Pro Ser Pro Asn Glu Lys Leu Gln Asn Ile Asn Leu
        435                 440                 445
Ala Met Ser Pro Leu Pro Thr Ala Glu Thr Pro Lys Pro Leu Arg Ser
    450                 455                 460
Ser Ala Asp Pro Ala Leu Asn Gln Glu Val Ala Leu Lys Leu Glu Pro
465                 470                 475                 480
Asn Pro Glu Ser Leu Glu Leu Ser Phe Thr Met Pro Gln Ile Gln Asp
                485                 490                 495
Gln Thr Pro Ser Pro Ser Asp Gly Ser Thr Arg Gln Ser Ser Pro Glu
            500                 505                 510
Pro Asn Ser Pro Ser Glu Tyr Cys Phe Tyr Val Asp Ser Asp Met Val
        515                 520                 525
Asn Glu Phe Lys Leu Glu Leu Val Glu Lys Leu Phe Ala Glu Asp Thr
    530                 535                 540
Glu Ala Lys Asn Pro Phe Ser Thr Gln Asp Thr Asp Leu Asp Leu Glu
545                 550                 555                 560
Met Leu Ala Pro Tyr Ile Pro Met Asp Asp Asp Phe Gln Leu Arg Ser
                565                 570                 575
Phe Asp Gln Leu Ser Pro Leu Glu Ser Ser Ser Ala Ser Pro Glu Ser
            580                 585                 590
Ala Ser Pro Gln Ser Thr Val Thr Val Phe Gln Gln Thr Gln Ile Gln
        595                 600                 605
Glu Pro Thr Ala Asn Ala Thr Thr Thr Thr Ala Thr Thr Asp Glu Leu
    610                 615                 620
Lys Thr Val Thr Lys Asp Arg Met Glu Asp Ile Lys Ile Leu Ile Ala
625                 630                 635                 640
Ser Pro Ser Pro Thr His Ile His Lys Glu Thr Thr Ser Ala Thr Ser
                645                 650                 655
Ser Pro Tyr Arg Asp Thr Gln Ser Arg Thr Ala Ser Pro Asn Arg Ala
            660                 665                 670
Gly Lys Gly Val Ile Glu Gln Thr Glu Lys Ser His Pro Arg Ser Pro
        675                 680                 685
Asn Val Leu Ser Val Ala Leu Ser Gln Arg Thr Thr Val Pro Glu Glu
    690                 695                 700
Glu Leu Asn Pro Lys Ile Leu Ala Leu Gln Asn Ala Gln Arg Lys Arg
705                 710                 715                 720
Lys Met Glu His Asp Gly Ser Leu Phe Gln Ala Val Gly Ile Gly Thr
                725                 730                 735
Leu Leu Gln Gln Pro Asp Asp His Ala Ala Thr Thr Ser Leu Ser Trp
            740                 745                 750
Lys Arg Val Lys Gly Cys Lys Ser Ser Glu Gln Asn Gly Met Glu Gln
        755                 760                 765
Lys Thr Ile Ile Leu Ile Pro Ser Asp Leu Ala Cys Arg Leu Leu Gly
```

-continued

```
                770                 775                 780

Gln Ser Met Asp Glu Ser Gly Leu Pro Gln Leu Thr Ser Tyr Asp Cys
785                 790                 795                 800

Glu Val Asn Ala Pro Ile Gln Gly Ser Arg Asn Leu Leu Gln Gly Glu
                805                 810                 815

Glu Leu Leu Arg Ala Leu Asp Gln Val Asn
                820                 825

(2) INFORMATION FOR SEQ ID NO:3:

(i) SEQUENCE CHARACTERISTICS:
        (A) LENGTH: 373 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:3:

Met Glu Gly Ile Ala Gly Ser Arg Arg Ser Lys Glu Ser Glu Val Phe
1                   5                  10                  15

Tyr Glu Leu Ala His Gln Leu Pro Leu Pro His Asn Val Ser Ser His
                20                  25                  30

Leu Asp Lys Ala Ser Val Met Arg Leu Thr Ile Ser Tyr Leu Arg Val
            35                  40                  45

Arg Lys Leu Leu Asp Ala Gly Asp Leu Asp Ile Glu Asp Asp Met Lys
50                  55                  60

Ala Gln Met Asn Cys Phe Tyr Leu Lys Ala Leu Asp Gly Phe Val Met
65                  70                  75                  80

Val Leu Thr Asp Asp Gly Asp Met Ile Tyr Ile Ser Asp Asn Val Asn
                85                  90                  95

Lys Tyr Met Gly Leu Thr Gln Phe Glu Leu Thr Gly His Ser Val Phe
                100                 105                 110

Asp Phe Thr His Pro Cys Asp His Glu Glu Met Arg Glu Met Leu Thr
            115                 120                 125

His Arg Asn Gly Leu Val Lys Lys Gly Lys Glu Gln Asn Thr Gln Arg
130                 135                 140

Ser Phe Phe Leu Arg Met Lys Cys Thr Leu Thr Ser Arg Gly Arg Thr
145                 150                 155                 160

Met Asn Ile Lys Ser Ala Thr Trp Lys Val Leu His Cys Thr Gly His
                165                 170                 175

Ile His Val Tyr Asp Thr Asn Ser Asn Gln Pro Gln Cys Gly Tyr Lys
                180                 185                 190

Lys Pro Pro Met Thr Cys Leu Val Leu Ile Cys Glu Pro Ile Pro His
            195                 200                 205

Pro Ser Asn Ile Glu Ile Pro Leu Asp Ser Lys Thr Phe Leu Ser Arg
210                 215                 220

His Ser Leu Asp Met Lys Phe Ser Tyr Cys Asp Glu Arg Ile Thr Glu
225                 230                 235                 240

Leu Met Gly Tyr Glu Pro Glu Glu Leu Leu Gly Arg Ser Ile Tyr Glu
                245                 250                 255

Tyr Tyr His Ala Leu Asp Ser Asp His Leu Thr Lys Thr His His Asp
                260                 265                 270

Met Phe Thr Lys Gly Gln Val Thr Thr Gly Gln Tyr Arg Met Leu Ala
            275                 280                 285

Lys Arg Gly Gly Tyr Val Trp Val Glu Thr Gln Ala Thr Val Ile Tyr
```

```
              290                 295                 300
Asn Thr Lys Asn Ser Gln Pro Gln Cys Ile Val Cys Val Asn Tyr Val
305                 310                 315                 320

Val Ser Gly Ile Ile Gln His Asp Leu Ile Phe Ser Leu Gln Gln Thr
                325                 330                 335

Glu Cys Val Leu Lys Pro Val Glu Ser Ser Asp Met Lys Met Thr Gln
                340                 345                 350

Leu Phe Thr Lys Val Glu Ser Glu Asp Thr Ser Ser Leu Phe Asp Lys
            355                 360                 365

Leu Lys Ile Gln Thr
        370

(2) INFORMATION FOR SEQ ID NO:4:

(i) SEQUENCE CHARACTERISTICS:
        (A) LENGTH: 805 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:4:

Met Glu Gly Ile Ala Gly Ser Arg Arg Ser Lys Glu Ser Glu Val Phe
1               5                   10                  15

Tyr Glu Leu Ala His Gln Leu Pro Leu Pro His Asn Val Ser Ser His
                20                  25                  30

Leu Asp Lys Ala Ser Val Met Arg Leu Thr Ile Ser Tyr Leu Arg Val
            35                  40                  45

Arg Lys Leu Leu Asp Ala Gly Asp Leu Asp Ile Glu Asp Asp Met Lys
50                  55                  60

Ala Gln Met Asn Cys Phe Tyr Leu Lys Ala Leu Asp Gly Phe Val Met
65                  70                  75                  80

Val Leu Thr Asp Asp Gly Asp Met Ile Tyr Ile Ser Asp Asn Val Asn
                85                  90                  95

Lys Tyr Met Gly Leu Thr Gln Phe Glu Leu Thr Gly His Ser Val Phe
                100                 105                 110

Asp Phe Thr His Pro Cys Asp His Glu Glu Met Arg Glu Met Leu Thr
            115                 120                 125

His Arg Asn Gly Leu Val Lys Lys Gly Lys Glu Gln Asn Thr Gln Arg
        130                 135                 140

Ser Phe Phe Leu Arg Met Lys Cys Thr Leu Thr Ser Arg Gly Arg Thr
145                 150                 155                 160

Met Asn Ile Lys Ser Ala Thr Trp Lys Val Leu His Cys Thr Gly His
                165                 170                 175

Ile His Val Tyr Asp Thr Asn Ser Asn Gln Pro Gln Cys Gly Tyr Lys
                180                 185                 190

Lys Pro Pro Met Thr Cys Leu Val Leu Ile Cys Glu Pro Ile Pro His
            195                 200                 205

Pro Ser Asn Ile Glu Ile Pro Leu Asp Ser Lys Thr Phe Leu Ser Arg
210                 215                 220

His Ser Leu Asp Met Lys Phe Ser Tyr Cys Asp Glu Arg Ile Thr Glu
225                 230                 235                 240

Leu Met Gly Tyr Glu Pro Glu Glu Leu Leu Gly Arg Ser Ile Tyr Glu
                245                 250                 255

Tyr Tyr His Ala Leu Asp Ser Asp His Leu Thr Lys Thr His His Asp
```

```
                260                 265                 270
Met Phe Thr Lys Gly Gln Val Thr Gly Gln Tyr Arg Met Leu Ala
                275                 280                 285
Lys Arg Gly Gly Tyr Val Trp Val Glu Thr Gln Ala Thr Val Ile Tyr
290                 295                 300
Asn Thr Lys Asn Ser Gln Pro Gln Cys Ile Val Cys Val Asn Tyr Val
305                 310                 315                 320
Val Ser Gly Ile Ile Gln His Asp Leu Ile Phe Ser Leu Gln Gln Thr
                325                 330                 335
Glu Cys Val Leu Lys Pro Val Glu Ser Ser Asp Met Lys Met Thr Gln
                340                 345                 350
Leu Phe Thr Lys Val Glu Ser Glu Asp Thr Ser Ser Leu Phe Asp Lys
                355                 360                 365
Leu Lys Lys Glu Pro Asp Ala Leu Thr Leu Leu Ala Pro Ala Ala Gly
370                 375                 380
Asp Thr Ile Ile Ser Leu Asp Phe Gly Ser Asn Asp Thr Glu Thr Asp
385                 390                 395                 400
Asp Gln Gln Leu Glu Glu Val Pro Leu Tyr Asn Asp Val Met Leu Pro
                405                 410                 415
Ser Pro Asn Glu Lys Leu Gln Asn Ile Asn Leu Ala Met Ser Pro Leu
                420                 425                 430
Pro Thr Ala Glu Thr Pro Lys Pro Leu Arg Ser Ser Ala Asp Pro Ala
                435                 440                 445
Leu Asn Gln Glu Val Ala Leu Lys Leu Glu Pro Asn Pro Glu Ser Leu
450                 455                 460
Glu Leu Ser Phe Thr Met Pro Gln Ile Gln Asp Gln Thr Pro Ser Pro
465                 470                 475                 480
Ser Asp Gly Ser Thr Arg Gln Ser Ser Pro Glu Pro Asn Ser Pro Ser
                485                 490                 495
Glu Tyr Cys Phe Tyr Val Asp Ser Asp Met Val Asn Glu Phe Lys Leu
                500                 505                 510
Glu Leu Val Glu Lys Leu Phe Ala Glu Asp Thr Glu Ala Lys Asn Pro
                515                 520                 525
Phe Ser Thr Gln Asp Thr Asp Leu Asp Leu Glu Met Leu Ala Pro Tyr
530                 535                 540
Ile Pro Met Asp Asp Asp Phe Gln Leu Arg Ser Phe Asp Gln Leu Ser
545                 550                 555                 560
Pro Leu Glu Ser Ser Ser Ala Ser Pro Glu Ser Ala Ser Pro Gln Ser
                565                 570                 575
Thr Val Thr Val Phe Gln Gln Thr Gln Ile Gln Glu Pro Thr Ala Asn
                580                 585                 590
Ala Thr Thr Thr Thr Ala Thr Thr Asp Glu Leu Lys Thr Val Thr Lys
                595                 600                 605
Asp Arg Met Glu Asp Ile Lys Ile Leu Ile Ala Ser Pro Ser Pro Thr
                610                 615                 620
His Ile His Lys Glu Thr Thr Ser Ala Thr Ser Ser Pro Tyr Arg Asp
625                 630                 635                 640
Thr Gln Ser Arg Thr Ala Ser Pro Asn Arg Ala Gly Lys Gly Val Ile
                645                 650                 655
Glu Gln Thr Glu Lys Ser His Pro Arg Ser Pro Asn Val Leu Ser Val
                660                 665                 670
Ala Leu Ser Gln Arg Thr Thr Val Pro Glu Glu Glu Leu Asn Pro Lys
                675                 680                 685
```

```
Ile Leu Ala Leu Gln Asn Ala Gln Arg Lys Arg Lys Met Glu His Asp
    690                 695                 700
Gly Ser Leu Phe Gln Ala Val Gly Ile Gly Thr Leu Leu Gln Gln Pro
705                 710                 715                 720
Asp Asp His Ala Ala Thr Thr Ser Leu Ser Trp Lys Arg Val Lys Gly
                725                 730                 735
Cys Lys Ser Ser Glu Gln Asn Gly Met Glu Gln Lys Thr Ile Ile Leu
                740                 745                 750
Ile Pro Ser Asp Leu Ala Cys Arg Leu Leu Gly Gln Ser Met Asp Glu
            755                 760                 765
Ser Gly Leu Pro Gln Leu Thr Ser Tyr Asp Cys Glu Val Asn Ala Pro
    770                 775                 780
Ile Gln Gly Ser Arg Asn Leu Leu Gln Gly Glu Glu Leu Leu Arg Ala
785                 790                 795                 800
Leu Asp Gln Val Asn
            805
```

(2) INFORMATION FOR SEQ ID NO:5:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:5:

GATCGCCCTA CGTGCTGTCT CA                                             22

(2) INFORMATION FOR SEQ ID NO:6:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:6:

GATCGCCCTA AAAGCTGTCT CA                                             22

(2) INFORMATION FOR SEQ ID NO:7:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: N at positions 15 and 27 is inosine.

(xi) SEQUENCE DESCRIPTION: SEQ ID NO:7:

ATCGGATCCA TCACNGARCT SATGGGNTAT A                                 31

(2) INFORMATION FOR SEQ ID NO:8:

(i) SEQUENCE CHARACTERISTICS:
        (A) LENGTH: 27 base pairs
        (B) TYPE: nucleic acid (C) STRANDEDNESS: single
        (D) TOPOLOGY: linear (ii) MOLECULE TYPE: DNA (ix) FEATURE:
        (D) OTHER INFORMATION: N is inosine.

(xi) SEQUENCE DESCRIPTION: SEQ ID NO:8:

ATTAAGCMTG GTSAGGTGGT CNSWGTC                                        27

(2) INFORMATION FOR SEQ ID NO:9:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:9:

ATTAAGCTTG CATGGTAGTA YTCATAGAT                                      29

(2) INFORMATION FOR SEQ ID NO:10:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: N is inosine.

(xi) SEQUENCE DESCRIPTION: SEQ ID NO:10:

ATAAAGCTTG TSTAYGTSTC NGAYTCGG                                       28

(2) INFORMATION FOR SEQ ID NO:11:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: N is inosine.

(xi) SEQUENCE DESCRIPTION: SEQ ID NO:11:

ATCGAATTCY TCNGACTGNG GCTGGTT                                        27

(2) INFORMATION FOR SEQ ID NO:12:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:12:

TACGGATCCG CCATGGCGGC GACTACTGA                                      29

(2) INFORMATION FOR SEQ ID NO:13:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:13:

AGCCAGGGCA CTACAGGTGG GTACC                    25

(2) INFORMATION FOR SEQ ID NO:14:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:14:

GTTCCCCGCA AGGACTTCAT GTGAG                    25

(2) INFORMATION FOR SEQ ID NO:15:

(i) SEQUENCE CHARACTERISTICS:
        (A) LENGTH: 15 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:15:

Ile Thr Glu Leu Met Gly Tyr Glu Pro Glu Glu Leu Leu Gly Arg
1               5                   10                  15

(2) INFORMATION FOR SEQ ID NO:16:

(i) SEQUENCE CHARACTERISTICS:
        (A) LENGTH: 12 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:16:

Xaa Ile Ile Leu Ile Pro Ser Asp Leu Ala Xaa Arg
1               5                   10

(2) INFORMATION FOR SEQ ID NO:17:

(i) SEQUENCE CHARACTERISTICS:
        (A) LENGTH: 16 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:17:

Ser Ile Tyr Glu Tyr Tyr His Ala Leu Asp Ser Asp His Leu Thr Lys
1               5                   10                  15

(2) INFORMATION FOR SEQ ID NO:18:

(i) SEQUENCE CHARACTERISTICS:
            (A) LENGTH: 5 amino acids
            (B) TYPE: amino acid
            (C) STRANDEDNESS: Not Relevant
            (D) TOPOLOGY: linear (ii) MOLECULE TYPE: protein (xi) SEQUENCE DESCRIPTION: SEQ ID NO:18:

Ser Phe Phe Leu Arg
1               5

(2) INFORMATION FOR SEQ ID NO:19:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:19:

GCCRCCATGG                                                                          10

(2) INFORMATION FOR SEQ ID NO:20:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:20:

TTCACCATGG                                                                          10

(2) INFORMATION FOR SEQ ID NO:21:

(i) SEQUENCE CHARACTERISTICS:
            (A) LENGTH: 18 amino acids
            (B) TYPE: amino acid
            (C) STRANDEDNESS: Not Relevant
            (D) TOPOLOGY: linear (ii) MOLECULE TYPE: protein (xi) SEQUENCE DESCRIPTION: SEQ ID NO:21:

Val Val Tyr Val Ser Asp Ser Val Thr Pro Val Leu Asn Gln Pro Gln
1               5                   10                  15
Ser Glu (2) INFORMATION FOR SEQ ID NO:22:

(i) SEQUENCE CHARACTERISTICS:
            (A) LENGTH: 33 amino acids
            (B) TYPE: amino acid
            (C) STRANDEDNESS: Not Relevant
            (D) TOPOLOGY: linear (ii) MOLECULE TYPE: protein (xi) SEQUENCE DESCRIPTION: SEQ ID NO:22:

Thr Ser Gln Phe Gly Val Gly Ser Phe Gln Thr Pro Ser Ser Phe Ser
1               5                   10                  15
Ser Met Xaa Leu Pro Gly Ala Pro Thr Ala Ser Pro Gly Ala Ala Ala

```
                 20                  25                  30
Tyr (2) INFORMATION FOR SEQ ID NO:23:

(i) SEQUENCE CHARACTERISTICS:
        (A) LENGTH: 6 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:23:

CACGTG                                                                6

(2) INFORMATION FOR SEQ ID NO:24:

(i) SEQUENCE CHARACTERISTICS:
        (A) LENGTH: 7 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:24:

BACGTGC                                                               7

(2) INFORMATION FOR SEQ ID NO:25:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: N is inosine.

(xi) SEQUENCE DESCRIPTION: SEQ ID NO:25:

TNGNGCGTGM SA                                                        12

(2) INFORMATION FOR SEQ ID NO:26:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:26:

UUAUUUAWW                                                             9

(2) INFORMATION FOR SEQ ID NO:27:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:27:
```

ATAGGATCCT CAGGTCAGCT GGCACCCAG                                             29

(2) INFORMATION FOR SEQ ID NO:28:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:28:

CCAAAGCTTC TATTCTGAAA AGGGGGG                                               27

(2) INFORMATION FOR SEQ ID NO:29:

(i) SEQUENCE CHARACTERISTICS:
        (A) LENGTH: 7 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:29:

RWACGTG                                                                      7

(2) INFORMATION FOR SEQ ID NO:30:

(i) SEQUENCE CHARACTERISTICS:
        (A) LENGTH: 8 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:30:

TACGTGCT                                                                     8

(2) INFORMATION FOR SEQ ID NO:31:

(i) SEQUENCE CHARACTERISTICS:
        (A) LENGTH: 8 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:31:

GACGTGCG                                                                     8

(2) INFORMATION FOR SEQ ID NO:32:

(i) SEQUENCE CHARACTERISTICS:
        (A) LENGTH: 8 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:32:

CACGTGCG                                                                     8

(2) INFORMATION FOR SEQ ID NO:33:

(i) SEQUENCE CHARACTERISTICS:
        (A) LENGTH: 8 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:33:

BACGTGCK        8

(2) INFORMATION FOR SEQ ID NO:34:

(i) SEQUENCE CHARACTERISTICS:
        (A) LENGTH: 8 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:34:

CACGTGCT        8

(2) INFORMATION FOR SEQ ID NO:35:

(i) SEQUENCE CHARACTERISTICS:
        (A) LENGTH: 30 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:35:

Met Glu Gly Ile Ala Gly Ala Asn Asp Lys Lys Lys Ile Ser Ser Glu
1             5                  10               15

Arg Arg Lys Glu Lys Ser Arg Asp Ala Ala Arg Ser Arg Arg
          20                 25               30

(2) INFORMATION FOR SEQ ID NO:36:

(i) SEQUENCE CHARACTERISTICS:
        (A) LENGTH: 54 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:36:

Arg Arg Lys Glu Lys Ser Arg Asp Ala Ala Arg Ser Arg Arg Ser Lys
1             5                  10               15

Glu Ser Glu Val Phe Tyr Glu Leu Ala His Gln Leu Pro Leu Pro His
          20                 25               30

Asn Val Ser Ser His Leu Asp Lys Ala Ser Val Met Arg Leu Thr Ile
          35                 40               45

Ser Tyr Leu Arg Val Arg
    50

(2) INFORMATION FOR SEQ ID NO:37:

(i) SEQUENCE CHARACTERISTICS:
        (A) LENGTH: 53 amino acids
        (B) TYPE: amino acid (C) STRANDEDNESS: Not Relevant
            (D) TOPOLOGY: linear (ii) MOLECULE TYPE: protein (xi) SEQUENCE DESCRIPTION: SEQ ID NO:37:

Ala Arg Glu Asn His Ser Glu Ile Glu Arg Arg Arg Asn Lys Met
1               5                   10                  15

Thr Ala Tyr Ile Thr Glu Leu Ser Asp Met Val Pro Thr Cys Ser Ala
            20                  25                  30

Leu Ala Arg Lys Pro Asp Lys Leu Thr Ile Leu Arg Met Ala Val Ser
        35                  40                  45

His Met Lys Ser Leu
    50

(2) INFORMATION FOR SEQ ID NO:38:

(i) SEQUENCE CHARACTERISTICS:
        (A) LENGTH: 53 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:38:

Met Lys Glu Lys Ser Lys Asn Ala Ala Arg Thr Arg Arg Glu Lys Glu
1               5                   10                  15

Asn Thr Glu Phe Cys Glu Leu Ala Lys Leu Leu Pro Leu Pro Ala Ala
            20                  25                  30

Ile Thr Ser Gln Leu Asp Lys Ala Ser Val Ile Arg Leu Thr Thr Ser
        35                  40                  45

Tyr Leu Lys Met Arg
    50

(2) INFORMATION FOR SEQ ID NO:39:

(i) SEQUENCE CHARACTERISTICS:
        (A) LENGTH: 53 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:39:

Ala Glu Gly Ile Lys Ser Asn Pro Ser Lys Arg His Arg Asp Arg Leu
1               5                   10                  15

Asn Thr Glu Leu Asp Arg Leu Ala Ser Leu Leu Pro Phe Pro Gln Asp
            20                  25                  30

Val Ile Asn Lys Leu Asp Lys Leu Ser Val Leu Arg Leu Ser Val Thr
        35                  40                  45

Tyr Leu Arg Ala Lys
    50

(2) INFORMATION FOR SEQ ID NO:40:

(i) SEQUENCE CHARACTERISTICS:
        (A) LENGTH: 22 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:40:

Lys Ser Arg Arg Arg Lys Glu Leu Ala Leu Pro Pro Leu Asp Lys Ser
1               5                   10                  15

Val Arg Leu Ser Tyr Leu
            20

(2) INFORMATION FOR SEQ ID NO:41:

(i) SEQUENCE CHARACTERISTICS:
        (A) LENGTH: 53 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:41:

Ala Arg Glu Asn His Ser Glu Ile Glu Arg Arg Arg Asn Lys Met
1               5                   10                  15

Thr Ala Tyr Ile Thr Glu Leu Ser Asp Met Val Pro Thr Cys Ser Ala
            20                  25                  30

Leu Ala Arg Lys Pro Asp Lys Leu Thr Ile Leu Arg Met Ala Val Ser
        35                  40                  45

His Met Lys Ser Leu
    50

(2) INFORMATION FOR SEQ ID NO:42:

(i) SEQUENCE CHARACTERISTICS:
        (A) LENGTH: 53 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:42:

Lys Lys Asp Asn His Asn Leu Ile Ile Arg Arg Arg Phe Asn Ile
1               5                   10                  15

Asn Asp Arg Ile Lys Glu Leu Gly Thr Leu Ile Pro Lys Ser Asn Asp
            20                  25                  30

Pro Asp Met Arg Trp Asn Lys Gly Thr Ile Leu Lys Ala Ser Val Asp
        35                  40                  45

Tyr Ile Arg Lys Leu
    50

(2) INFORMATION FOR SEQ ID NO:43:

(i) SEQUENCE CHARACTERISTICS:
        (A) LENGTH: 55 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:43:

Arg Arg Ala Gln His Asn Glu Val Glu Arg Arg Arg Asp Lys Ile
1               5                   10                  15

Asn Asn Trp Ile Val Gln Leu Ser Lys Ile Ile Pro Asp Cys Ser Met
            20                  25                  30

Glu Ser Thr Lys Ser Gly Gln Ser Lys Gly Gly Ile Leu Ser Lys Ala

```
                    35                  40                  45
Cys Asp Tyr Ile Gln Glu Leu
     50                  55
```

(2) INFORMATION FOR SEQ ID NO:44:

(i) SEQUENCE CHARACTERISTICS:
        (A) LENGTH: 52 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:44:

```
Lys Arg Lys Asn His Asn Phe Leu Glu Arg Lys Arg Arg Asn Asp Leu
 1               5                  10                  15
Arg Ser Arg Phe Leu Ala Leu Arg Asp Gln Val Pro Thr Leu Ala Ser
             20                  25                  30
Cys Ser Lys Ala Pro Lys Val Val Ile Leu Ser Lys Ala Leu Glu Tyr
             35                  40                  45
Leu Gln Ala Leu
     50
```

(2) INFORMATION FOR SEQ ID NO:45:

(i) SEQUENCE CHARACTERISTICS:
        (A) LENGTH: 48 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:45:

```
Arg Lys Asp Ser His Lys Glu Val Glu Arg Arg Arg Arg Glu Asn Ile
 1               5                  10                  15
Asn Thr Ala Ile Asn Val Leu Ser Asp Leu Leu Pro Val Arg Glu Ser
             20                  25                  30
Ser Lys Ala Ala Ile Leu Ala Arg Ala Ala Glu Tyr Ile Gln Lys Leu
             35                  40                  45
```

(2) INFORMATION FOR SEQ ID NO:46:

(i) SEQUENCE CHARACTERISTICS:
        (A) LENGTH: 21 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:46:

```
His Asn Glu Glu Arg Arg Arg Arg Leu Ser Asp Pro Lys Lys Ile Leu
 1               5                  10                  15
Ala Tyr Ile Gln Leu
         20
```

(2) INFORMATION FOR SEQ ID NO:47:

(i) SEQUENCE CHARACTERISTICS:
        (A) LENGTH: 102 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:47:

```
Asp Gly Asp Met Ile Tyr Ile Ser Asp Asn Val Asn Lys Tyr Met Gly
 1               5                  10                  15
Leu Thr Gln Phe Glu Leu Thr Gly His Ser Val Phe Asp Phe Thr His
                20                  25                  30
Pro Cys Asp His Glu Glu Met Arg Glu Met Leu Thr His Arg Asn Gly
            35                  40                  45
Leu Val Lys Asp Met Lys Phe Ser Tyr Cys Asp Glu Arg Ile Thr Glu
 50                  55                  60
Leu Met Gly Tyr Glu Pro Glu Glu Leu Leu Gly Arg Ser Ile Tyr Glu
 65                  70                  75                  80
Tyr Tyr His Ala Leu Asp Ser Asp His Leu Thr Lys Thr His His Asp
                85                  90                  95
Met Phe Thr Lys Gly Gln
            100
```

(2) INFORMATION FOR SEQ ID NO:48:

(i) SEQUENCE CHARACTERISTICS:
        (A) LENGTH: 104 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:48:

```
Thr Gly Arg Val Val Tyr Val Ser Asp Ser Val Thr Pro Val Leu Asn
 1               5                  10                  15
Gln Pro Gln Ser Glu Trp Phe Gly Ser Thr Leu Tyr Asp Gln Val His
                20                  25                  30
Pro Asp Asp Val Asp Lys Leu Arg Glu Gln Leu Ser Thr Ser Glu Asn
            35                  40                  45
Ala Leu Thr Glu Gly Ile Phe Thr Phe Val Asp His Arg Cys Val Ala
 50                  55                  60
Thr Val Gly Tyr Gln Pro Gln Glu Leu Leu Gly Lys Asn Ile Val Glu
 65                  70                  75                  80
Phe Asp Cys His Pro Glu Asp Gln Gln Leu Leu Arg Asp Ser Phe Gln
                85                  90                  95
Gln Val Val Lys Leu Lys Gly Gln
            100
```

(2) INFORMATION FOR SEQ ID NO:49:

(i) SEQUENCE CHARACTERISTICS:
        (A) LENGTH: 105 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:49:

```
Asp Ala Leu Val Phe Tyr Ala Ser Ser Thr Ile Gln Asp Tyr Leu Gly
 1               5                  10                  15
Phe Gln Gln Ser Asp Val Ile His Gln Ser Val Tyr Glu Leu Ile His
                20                  25                  30
```

```
Thr Glu Asp Arg Ala Glu Phe Gln Arg Gln Leu His Trp Ala Leu Asn
            35                  40                  45

Pro Ser Gln Cys Thr Asp Phe Thr Pro Ile Gly Cys Asp Ala Lys Gly
 50                  55                  60

Arg Ile Val Leu Gly Tyr Thr Glu Ala Glu Leu Cys Thr Arg Gly Ser
 65                  70                  75                  80

Gly Tyr Gln Phe Ile His Ala Ala Asp Met Leu Tyr Cys Ala Glu Ser
                 85                  90                  95

His Ile Arg Met Ile Lys Thr Gly Glu
            100                 105
```

(2) INFORMATION FOR SEQ ID NO:50:

(i) SEQUENCE CHARACTERISTICS:
        (A) LENGTH: 102 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:50:

```
Asp Gly Lys Ile Met Tyr Ile Ser Glu Thr Ala Ser Val His Leu Gly
 1                   5                  10                  15

Leu Ser Gln Val Glu Leu Thr Gly Asn Ser Ile Phe Glu Tyr Ile His
                 20                  25                  30

Asn Tyr Asp Gln Asp Glu Met Asn Ala Ile Leu Ser Leu His Pro His
            35                  40                  45

Ile Asn Gln Asp Met Lys Leu Ile Phe Phe Asp Ala Arg Val Ser Gln
 50                  55                  60

Leu Thr Gly Tyr Glu Pro Gln Asp Leu Ile Glu Lys Thr Leu Tyr Gln
 65                  70                  75                  80

Tyr Ile His Ala Ala Asp Ile Met Ala Met Arg Cys Ser His Gln Ile
                 85                  90                  95

Leu Leu Tyr Lys Gly Gln
            100
```

(2) INFORMATION FOR SEQ ID NO:51:

(i) SEQUENCE CHARACTERISTICS:
        (A) LENGTH: 102 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:51:

```
Asp Gly Ile Val Leu Tyr Thr Thr Pro Ser Ile Thr Asp Val Leu Gly
 1                   5                  10                  15

Tyr Pro Arg Asp Met Trp Leu Gly Arg Ser Phe Ile Asp Phe Val His
                 20                  25                  30

Leu Lys Asp Arg Ala Thr Phe Ala Ser Gln Ile Thr Thr Gly Ile Pro
            35                  40                  45

Ile Ala Glu Thr Gly Ile Ile Ser His Val Asp Ser Ala Ala Val Ser
 50                  55                  60

Ala Leu Gly Tyr Leu Pro Gln Asp Leu Ile Gly Arg Ser Ile Met Asp
 65                  70                  75                  80

Phe Tyr His His Glu Asp Leu Ser Val Met Lys Glu Thr Tyr Glu Thr
                 85                  90                  95
```

```
Val Met Lys Lys Gly Gln
            100
```

(2) INFORMATION FOR SEQ ID NO:52:

(i) SEQUENCE CHARACTERISTICS:
        (A) LENGTH: 103 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:52:

```
Asn Gly Arg Ile Ile Tyr Ile Ser Ala Asn Ser Lys Leu His Leu Gly
1               5                   10                  15

Tyr Leu Gln Gly Glu Met Ile Gly Ser Phe Leu Lys Thr Phe Leu His
            20                  25                  30

Glu Glu Asp Gln Phe Leu Val Glu Ser Tyr Phe Tyr Asn Glu His His
        35                  40                  45

Leu Met Pro Cys Thr Trp Val Phe Met Asn Glu Ser Gly Ile Ser Leu
    50                  55                  60

Phe Glu Ala Ala Thr Tyr Glu Asp Leu Ile Gly Lys Asn Ile Tyr Asp
65                  70                  75                  80

Gln Leu His Pro Cys Asp His Glu Asp Val Lys Glu Arg Ile Gln Asn
            85                  90                  95

Ile Ala Glu Gln Lys Thr Glu
            100
```

(2) INFORMATION FOR SEQ ID NO:53:

(i) SEQUENCE CHARACTERISTICS:
        (A) LENGTH: 26 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:53:

```
Asp Gly Tyr Ser Leu Gly Gln Glu Gly Ser His Asp Leu Asp Gly Tyr
1               5                   10                  15

Pro Leu Gly Ile Tyr His Asp Lys Gly Gln
            20                  25
```

(2) INFORMATION FOR SEQ ID NO:54:

(i) SEQUENCE CHARACTERISTICS:
        (A) LENGTH: 46 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:54:

```
Met Glu Gly Ala Gly Gly Ala Asn Asp Lys Lys Lys Ile Ser Ser Glu
1               5                   10                  15

Arg Arg Lys Glu Lys Ser Arg Asp Ala Ala Arg Ser Arg Arg Leu Lys
            20                  25                  30

Lys Glu Pro Asp Ala Leu Thr Arg Ala Leu Asp Gln Val Asn
            35                  40                  45
```

(2) INFORMATION FOR SEQ ID NO:55:

(i) SEQUENCE CHARACTERISTICS:
        (A) LENGTH: 25 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:55:

```
Met Glu Gly Ile Ala Gly Ser Arg Arg Leu Lys Lys Glu Pro Asp Ala
 1               5                  10                  15
Leu Thr Arg Ala Leu Asp Gln Val Asn
            20                  25
```

(2) INFORMATION FOR SEQ ID NO:56:

(i) SEQUENCE CHARACTERISTICS:
        (A) LENGTH: 14 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:56:

```
Met Glu Gly Ile Ala Gly Ser Arg Arg Leu Lys Ile Gln Thr
 1               5                  10
```

(2) INFORMATION FOR SEQ ID NO:57:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO:57:

GCCCTACGTG CTGTCTCACA CAGCCTGTCT GA                                  32

(2) INFORMATION FOR SEQ ID NO:58:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:58:

CCGGGTAGCT GGCGTACGTG CTGCAG                                        26

(2) INFORMATION FOR SEQ ID NO:59:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:59:

GGGGCTGCTG CAGACGTGCG TGTG                                            24

(2) INFORMATION FOR SEQ ID NO:60:

(i) SEQUENCE CHARACTERISTICS:
        (A) LENGTH: 23 base pairs

```
        (B) TYPE: nucleic acid
        (C) STRANDEDNESS: single
        (D) TOPOLOGY: linear (xi) SEQUENCE DESCRIPTION: SEQ ID NO:60:

GTGAGACGTG CGGCTTCCGT TTG                                             23

(2) INFORMATION FOR SEQ ID NO:61:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:61:

CTGCCGACGT GCGCTCCGGA G                                               21

(2) INFORMATION FOR SEQ ID NO:62:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:62:

GTGGGAGCCC AGCGGACGTG CGGGAA                                          26

(2) INFORMATION FOR SEQ ID NO:63:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:63:

GGCCACGTGC GCCGCCTGCG CCTGCG                                          26

(2) INFORMATION FOR SEQ ID NO:64:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:64:

CTTCACGTGC GGGGACCAGG GACCGT                                          26
```